(12) United States Patent
Cawello et al.

(10) Patent No.: US 10,149,818 B2
(45) Date of Patent: Dec. 11, 2018

(54) DAILY FORMULATION OF LACOSAMIDE

(75) Inventors: Willi Cawello, Monheim (DE); Martin Alexander Schubert, Braunschweig (DE)

(73) Assignee: UCB PHARMA GMBH, Monheim (DE)

( * ) Notice: Subject to any disclaimer, the term of this patent is extended or adjusted under 35 U.S.C. 154(b) by 40 days.

(21) Appl. No.: 13/990,861

(22) PCT Filed: Dec. 1, 2011

(86) PCT No.: PCT/EP2011/006027
§ 371 (c)(1),
(2), (4) Date: May 31, 2013

(87) PCT Pub. No.: WO2012/072256
PCT Pub. Date: Jun. 7, 2012

(65) Prior Publication Data
US 2013/0251803 A1    Sep. 26, 2013

Related U.S. Application Data

(60) Provisional application No. 61/485,361, filed on May 12, 2011, provisional application No. 61/485,354, (Continued)

(30) Foreign Application Priority Data

Dec. 2, 2010   (EP) ..................................... 10193559
Dec. 2, 2010   (EP) ..................................... 10193561

(51) Int. Cl.
*A61K 9/16* (2006.01)
*A61K 9/20* (2006.01)
(Continued)

(52) U.S. Cl.
CPC .......... *A61K 9/0002* (2013.01); *A61K 9/1635* (2013.01); *A61K 9/1652* (2013.01); (Continued)

(58) Field of Classification Search
CPC ........ A61K 9/20; A61K 9/205; A61K 9/2059; A61K 9/2022; A61K 9/2031; (Continued)

(56) References Cited

U.S. PATENT DOCUMENTS 5,585,358 A   12/1996   Bialer et al. ..................... 514/19
6,133,261 A   10/2000   Harris .......................... 514/231.2
(Continued)

FOREIGN PATENT DOCUMENTS

EP    0888289    6/2001    ........... C07C 237/22
EP    1243262    9/2002    ........... A61K 31/165
(Continued)

OTHER PUBLICATIONS

Hiremath et al. Controlled Release Hydrophilic Matrix Tablet Formulations of Isoniazid: Design and In Vitro Studies. AAPS PharmSciTech, vol. 9, No. 4, Dec. 2008. pp. 1171-1178.*
(Continued)

*Primary Examiner* — Lakshmi S Channavajjala
(74) *Attorney, Agent, or Firm* — Harness, Dickey and Pierce, P.L.C.

(57) ABSTRACT

A modified release formulation of lacosamide suitable for once-daily administration.

28 Claims, 10 Drawing Sheets

Figure 1:
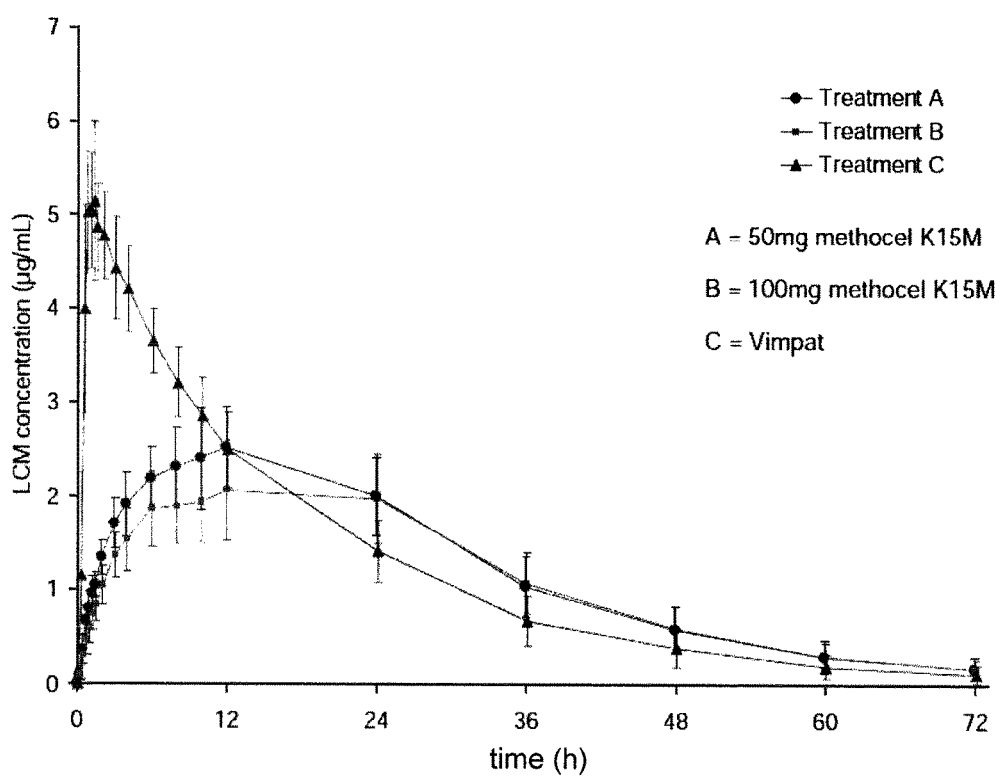

Related U.S. Application Data filed on May 12, 2011, provisional application No. 61/444,439, filed on Feb. 18, 2011, provisional application No. 61/444,447, filed on Feb. 18, 2011, provisional application No. 61/419,153, filed on Dec. 2, 2010, provisional application No. 61/419,158, filed on Dec. 2, 2010.

(51) Int. Cl.
*A61K 9/00* (2006.01)
*A61K 31/165* (2006.01)

(52) U.S. Cl.
CPC ............ *A61K 9/205* (2013.01); *A61K 9/2027* (2013.01); *A61K 9/2031* (2013.01); *A61K 9/2054* (2013.01); *A61K 9/2059* (2013.01); *A61K 31/165* (2013.01)

(58) Field of Classification Search
CPC .. A61K 9/2068; A61K 9/2054; A61K 31/165; A61K 2300/00
See application file for complete search history.

(56) References Cited

U.S. PATENT DOCUMENTS

| | | | |
|---|---|---|---|
| 6,803,481 B2 | 10/2004 | Selve | 560/157 |
| 7,416,864 B2 | 8/2008 | Stoehr | 435/106 |
| 7,427,601 B2 | 9/2008 | Stoehr | 514/19 |
| 7,687,553 B2 | 3/2010 | Beyreuther et al. | 523/115 |
| 7,718,161 B2 | 5/2010 | Stoehr | 424/1.69 |
| 7,794,987 B2 | 9/2010 | Stoehr | 435/106 |
| 7,820,857 B2 | 10/2010 | Stoehr et al. | 562/553 |
| 7,858,122 B2 | 12/2010 | Kshirsagar et al. | |
| 7,875,652 B2 | 1/2011 | Selve | 514/616 |
| 7,884,134 B2 | 2/2011 | Riedner et al. | 514/616 |
| 8,008,351 B2 | 8/2011 | Scheller et al. | 514/616 |
| 8,053,476 B2 | 11/2011 | Selve | 514/616 |
| 8,338,641 B2 | 12/2012 | Stoehr et al. | 514/616 |
| 2002/0052418 A1 | 5/2002 | Shirvan et al. | 514/626 |
| 2004/0204495 A1 | 10/2004 | Shirvan et al. | 514/616 |
| 2005/0085423 A1 | 4/2005 | Selve | 514/17 |
| 2005/0277596 A1 | 12/2005 | Stohr | 514/19 |
| 2006/0009384 A1 | 1/2006 | Rudd et al. | 514/12 |
| 2006/0100157 A1 | 5/2006 | Rauschkolb-Loffler et al. | 514/18 |
| 2006/0252749 A1 | 11/2006 | Stohr | 514/220 |
| 2007/0042969 A1 | 2/2007 | Rauschkolb-Loffler et al. | 514/19 |
| 2007/0043120 A1 | 2/2007 | Beyreuther et al. | 514/616 |
| 2007/0048372 A1 | 3/2007 | Beyreuther et al. | 424/464 |
| 2007/0197657 A1 | 8/2007 | Beyreuther et al. | 514/616 |
| 2008/0280835 A1 | 11/2008 | Beyreuther et al. | 514/19 |
| 2009/0018197 A1 | 1/2009 | Rudd et al. | 514/563 |
| 2009/0241205 A1 | 9/2009 | Beyreuther et al. | 800/9 |
| 2010/0029543 A1 | 2/2010 | Beyreuther et al. | 514/2 |
| 2010/0099770 A1 | 4/2010 | Selve | 514/616 |
| 2010/0240576 A1 | 9/2010 | Stoehr | 514/2 |
| 2010/0256179 A1 | 10/2010 | Stöhr et al. | 514/289 |
| 2010/0260716 A1 | 10/2010 | Stöhr et al. | 424/85.6 |
| 2010/0273714 A1 | 10/2010 | Stoehr | 514/17.7 |
| 2010/0324144 A1 | 12/2010 | Heers et al. | 514/616 |
| 2011/0021482 A1 | 1/2011 | Kohn et al. | 514/183 |
| 2011/0027359 A1 | 2/2011 | Goffin et al. | |
| 2011/0082211 A1 | 4/2011 | Selve | 514/616 |
| 2011/0130350 A1 | 6/2011 | Riedner et al. | 514/21.91 |
| 2012/0219631 A1 | 8/2012 | Kulkarni et al. | |
| 2012/0225119 A1* | 9/2012 | Beyreuther et al. | 424/456 |
| 2012/0238614 A1 | 9/2012 | Stöhr | 514/424 |
| 2013/0251813 A1 | 9/2013 | Cawello et al. | |
| 2014/0066515 A1 | 3/2014 | Heers et al. | |
| 2014/0088168 A1 | 3/2014 | Stoehr | |
| 2014/0128377 A1 | 5/2014 | Stoehr | |
| 2014/0128378 A1 | 5/2014 | Stoehr | |
| 2015/0104507 A1 | 4/2015 | Cawello et al. | |
| 2015/0202184 A1 | 7/2015 | Stohr | |

FOREIGN PATENT DOCUMENTS

| | | | |
|---|---|---|---|
| EP | 1243263 | 9/2002 | ........... A61K 31/165 |
| EP | 1541138 | 6/2005 | ........... A61K 31/165 |
| EP | 1754476 | 2/2007 | ........... A61K 31/165 |
| EP | 1920780 | 5/2008 | ............. A61K 38/04 |
| EP | 1925314 | 5/2008 | ............. A61K 38/04 |
| EP | 2035029 | 3/2009 | ............. A61K 31/55 |
| EP | 2037965 | 3/2009 | ............. A61K 31/19 |
| JP | 2008-528571 A | 7/2008 | |
| JP | 2009-542748 A | 12/2009 | |
| WO | WO 1997/033861 | 9/1997 | ........... C07C 237/22 |
| WO | WO 2005/053667 | 6/2005 | ........... A61K 31/165 |
| WO | WO 2005/092313 | 10/2005 | ........... A61K 31/165 |
| WO | WO 2005/099740 | 10/2005 | ............. A61K 38/05 |
| WO | WO 2005/110390 | 11/2005 | ........... A61K 31/165 |
| WO | WO 2005/120476 | 12/2005 | ............. A61K 31/00 |
| WO | WO 2005/120539 | 12/2005 | ............. A61K 38/00 |
| WO | WO 2006/000397 | 1/2006 | ............. A61K 38/03 |
| WO | WO 2006/021412 | 3/2006 | ........... A61K 31/165 |
| WO | WO 2006/079547 | 8/2006 | ........... A61K 31/165 |
| WO | WO-2007/0120485 A2 | 10/2007 | |
| WO | WO 2007/144196 | 12/2007 | ............. A61K 38/04 |
| WO | WO 2008/000513 | 1/2008 | ............. A61K 45/06 |
| WO | WO 2008/086492 | 7/2008 | ............... A61K 9/20 |
| WO | WO 2010/060624 | 6/2010 | ............... A61K 9/20 |
| WO | WO-2010/0060624 A2 | 6/2010 | |
| WO | WO2010060624 A2 * | 6/2010 | |
| WO | WO 2010/148300 | 12/2010 | ............. A01N 37/20 |
| WO | WO 2011/055385 | 5/2011 | ............... A61K 9/20 |
| WO | WO-2011/101863 A2 | 8/2011 | |

OTHER PUBLICATIONS

International Preliminary Report on Patentability dated Dec. 17, 2013 issued in PCT Patent Application No. PCT/EP2011/006027.
International Preliminary Report on Patentability dated Jun. 4, 2013 issued in PCT Patent Application No. PCT/EP2011/006026.
International Search Report and Written Opinion dated Nov. 14, 2012 issued in PCT Patent Application No. PCT/EP2011/006027.
Bialer et al. (2001) "Progress report on new antiepileptic drugs: a summary of the Fifth Eilat Conference (E1LAT V)" *Epilepsy Res.*, 43:11-58.
Bialer et al. (2002) "Progress report on new antiepileptic drugs: a summary of the Sixth Eilat Conference (EILAT VI)" *Epilepsy Res.*, 51:31-71.
Fisher, et al. (2003) "Trigeminal Neuralgia: current treatments and future developments" *Expert Opin. Emerging Drugs*, 8(1):123-143.
Hovinga (2002) "Novel anticonvulsant medications in development" *Expert Opin. Investig. Drugs*, 11(10) 1387-1406.
Löscher, W., et al. (2010), "Prevention or modification of epileptogenesis after brain insults: experimental approaches and translational research", *Pharmacological Reviews*, 62(4): 668-700.
Anonymous: "Vimpat (lacosamide) Tablets and Injection", Internet Citation, Oct. 28, 2008.
Invitation to Pay Additional Fees with Partial International Search Report dated Nov. 21, 2012 issued in PCT Application No. PCT/EP2011/006027.
International Search Report for PCT/EP2011/006026 published May 2, 2013.
USP 36 (the Physical Tests <711> Dissolution 1), Nov. 12, 2012, pp. 1-7 [online] , [retrieved on Apr. 17, 2014]. <URL: <https://mc.usp.org/sites/default/files/documents/GeneralChapterPDFs/c711%2OUSP36.pdf>.
Office Action dated Apr. 22, 2014 issued in U.S. Appl. No. 13/990,863.
Office Action dated Nov. 18, 2015 issued in U.S. Appl. No. 14/519,338.
Panayiotopoulos, C.P. (2010), *A Clinical Guide to Epileptic Syndromes and their Treatment*, p. 184.
US Food and Drug Administration (2008), "Vimpat (lacosamide) Tablets and Injection", *Approved Labeling Text—NDA* 22-253 and 22-254: 1-29, retrieved from <URL: http://web.archive.org/web/20090824053048/http://www.accessdata.fda.gov/drugsatfda_docs/label/2008/022253lbl.pdf>Dec. 14, 2015.

(56) References Cited

OTHER PUBLICATIONS

Harwood, R.(2005), "Hypromellose" *Handbook of Pharmaceutical Excipients*, 5: 346-349.
Office Action dated Sep. 21, 2016 issued in U.S. Appl. No. 14/519,338.
Office Action dated Apr. 28, 2016 issued in U.S. Appl. No. 14/519,338.
Proslov® HD90([retrieved from on-line website: http://www.americanpharmaceuticalreview.com/25260-Excipients/5821419-PROSLOV-SMCC-HD-90], last visit Sep. 16, 2016).
Kumar, P., et al., "Lacosamide: a New Antiepileptic Drug," Delhi Psychiatry Journal, 13(2): 356-366, (2010).

* cited by examiner

Figure 7

PK-PD results of the change of seizure frequency (N=3055 samples)

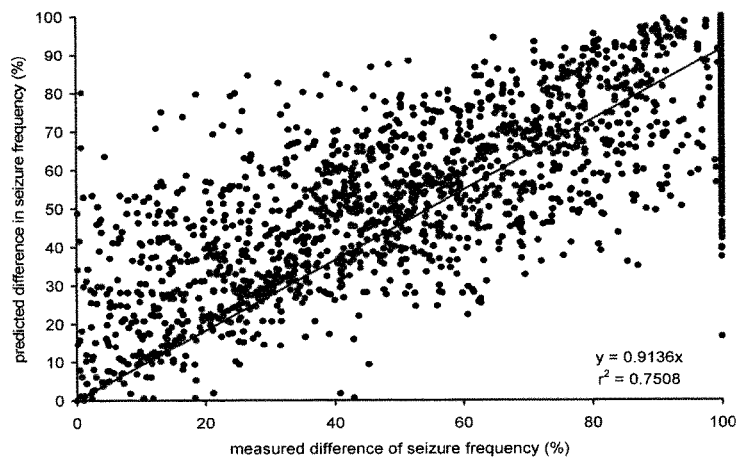

Figure 8

Achievable decrease of the daily number of seizures (%) in relation to daily lacosamide dose (based on results of $E_{max}$ model)[a]

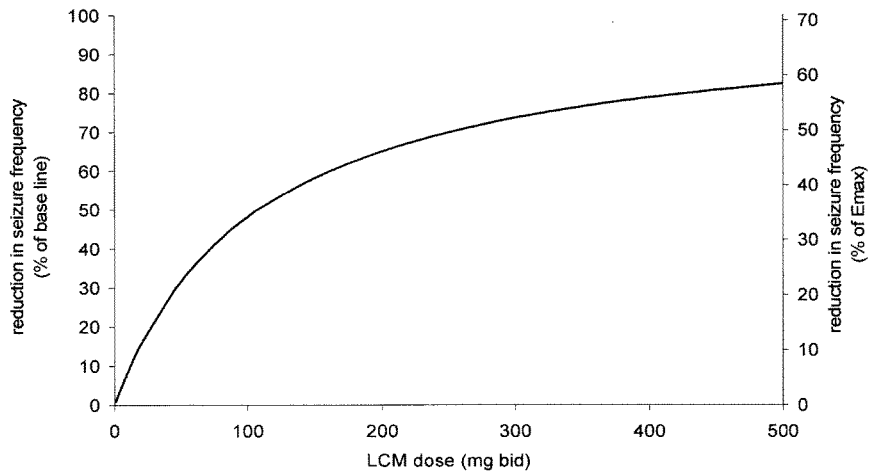

[a] calculated based on the results of the $E_{max}$ model according to equation given under 2.5.5.2; E(AUC)=Decrease of daily number of seizures in % of base line and in % of $E_{max}$ as function of AUC
Data source: $E_{max}$ model with AUC50=35.9µg/mL*h and $E_{max}$ =71%

DAILY FORMULATION OF LACOSAMIDE

CROSS-REFERENCE TO RELATED APPLICATIONS

This application is a national stage application under 35 U.S.C. § 371 of PCT International Application No. PCT/EP2011/006027 which has an International filing date of 1 Dec. 2011, and which claims the benefit under 35 U.S.C. § 119 to the following: EP Application No. 10193561.7 filed 2 Dec. 2010; EP Application No. 10193559.1 filed 2 Dec. 2010; U.S. Application No. 61/419,153 filed 2 Dec. 2010; U.S. Application No. 61/419,158 filed 2 Dec. 2010; U.S. Application No. 61/444,439 filed 18 Feb. 2011; U.S. Application No. 61/444,447 filed 18 Feb. 2011; U.S. Application No. 61/485,361 filed 12 May 2011; and U.S. Application No. 61/485,354 filed 12 May 2011. The contents of each application recited above are incorporated herein by reference in their entirety.

FIELD OF THE INVENTION

The present invention relates to modified release (MR) lacosamide formulations suitable for once daily administration, and to methods of making and using such formulations.

BACKGROUND

Lacosamide is an anticonvulsive which has been approved in several countries for the adjunctive treatment of partial-onset seizures in adults. Lacosamide is thought to work by selective enhancement of sodium channel slow inactivation and demonstrated efficacy and good tolerability in clinical trials. Lacosamide is available in the form of immediate release tablets, oral solutions and intravenous injection solutions. Tablets are approved as 50 to 200 mg dosage units for twice daily administration, and after such administration result in maximum dosage-normalized lacosamide steady state plasma levels (Cmax, ss, norm) of about 40-43 ng/ml/mg in a population of an average distribution volume of 50 liters. Tmax is usually reached within 1.4-1.5 hours after administration. Lacosamide has a solubility in water of about 27 g/L, and is rapidly and completely absorbed by the animal body substantially following a first order kinetic. Lacosamide has an elimination half-life of about 13 to 14 hours, making it an ideal candidate for a twice daily immediate release formulation. No modified release formulations of lacosamide are known so far.

State of the art lacosamide formulations are immediate release formulations. Such formulations are commercialized as "Vimpat®" tablets, having a tablet core consisting of 200 mg lacosamide as the active agent, 40 mg crospovidone as a disintegration agent, 56 mg microcrystalline cellulose type 102, 50 mg hydroxypropylcellulose (low substituted), 4 mg hydroxypropylcellulose, 125.2 mg silicified microcrystalline cellulose as fillers and binders, and 4.8 mg magnesium stearate as a lubricant. The tablets have a non-functional coating. This tablet releases 98% of the active agent within 15 minutes after contact with an aqueous medium.

SUMMARY OF THE INVENTION

The subject of the present invention is a controlled release formulation of lacosamide for oral administration, the composition comprising lacosamide and an agent for retarding the release of the lacosamide, wherein (a) an amount of about 8.5 wt-% to about 50 wt-% of lacosamide relative to the total lacosamide content of the formulation is released within 1 h, (b) an amount of about 15 wt-% to about 72 wt-% of lacosamide relative to the total lacosamide content of the formulation is released within 2 h, and/or (c) an amount of about 28 wt-% to about 95 wt-% of lacosamide relative to the total lacosamide content of the formulation is released within 4 h.

The formulations of the present invention are most preferably suitable for once daily administration.

The present invention also relates to methods of making and using such controlled release lacosmide formulations.

DESCRIPTIONS OF THE FIGURES

FIG. 1: Lacosamide pharmacokinetics in a phase I study after administration of a single oral dose of 200 mg lacosamide. Treatment A: modified release formulation of Example 19. Treatment B: modified release formulation of Example 20. Treatment C: immediate release Formulation Vimpat® (Example 6).

FIG. 2. A: Model calculation: absorption over time profiles for a first order absorption. B: Comparison of in-vitro dissolution profiles and calculated in-vivo absorption profiles C: Comparison of in-vitro dissolution profiles and calculated in-vivo absorption profiles (Sotax sinkers; 0.1N HCl)

Figure 3A:
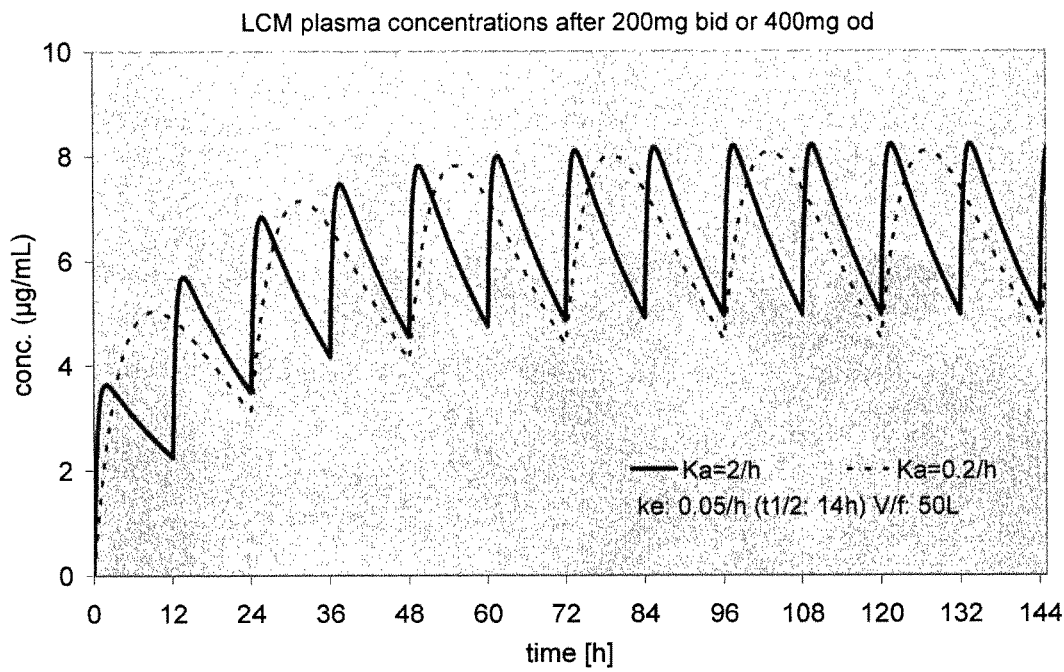
Figure 3B:
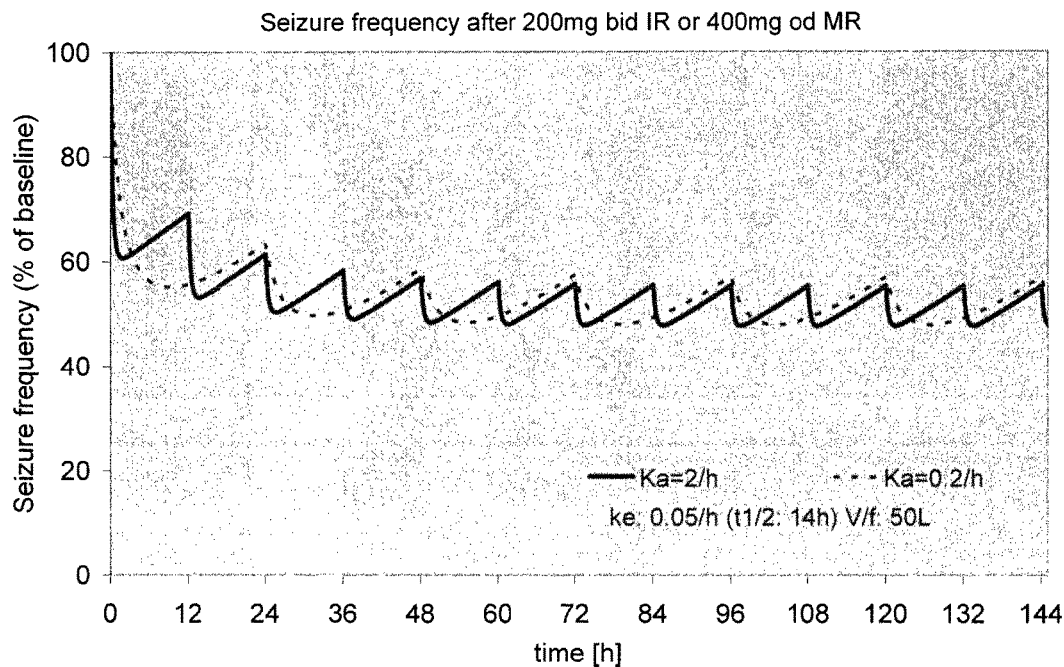
Figure 3C:
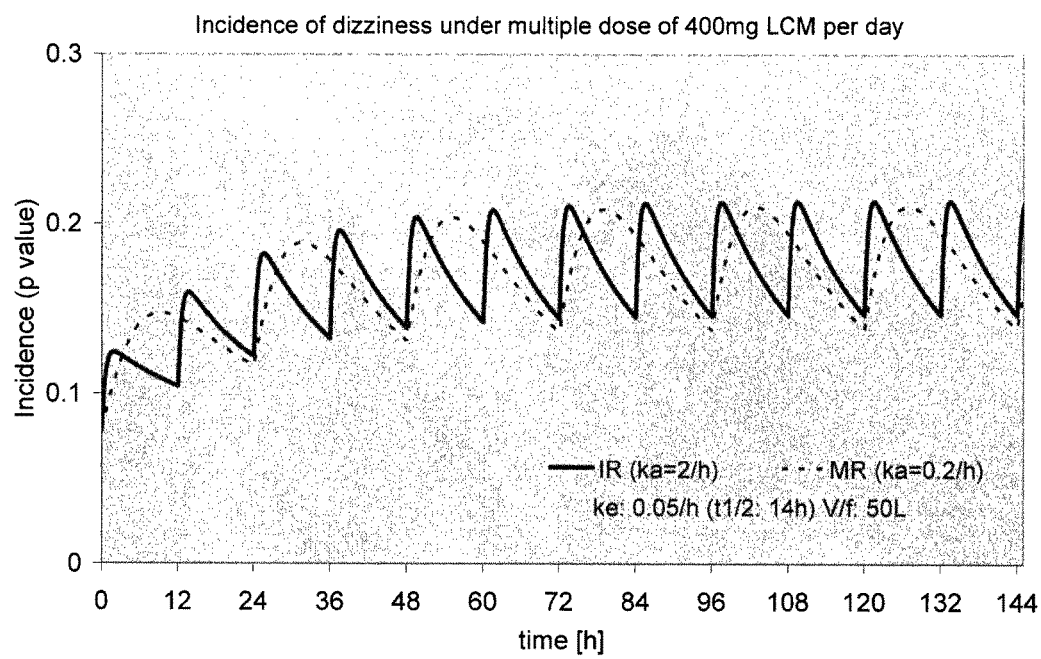

FIG. 3: Model calculation of profile of lacosamide pharmacokinetics (A), predicted therapeutic effect in terms of reduction of seizure frequency (B), and predicted adverse event(s) (incidence of dizziness) (C) as a function of time after multiple doses of a MR formulation (400 mg/day, administration once a day, constant dosing interval 24 h, with rate constant ka of 0.2/h) compared to a solid IR formulation (400 mg/day, administration 200 mg bid, constant dosing interval 12 h, ka of 2/h).

Figure 4A:
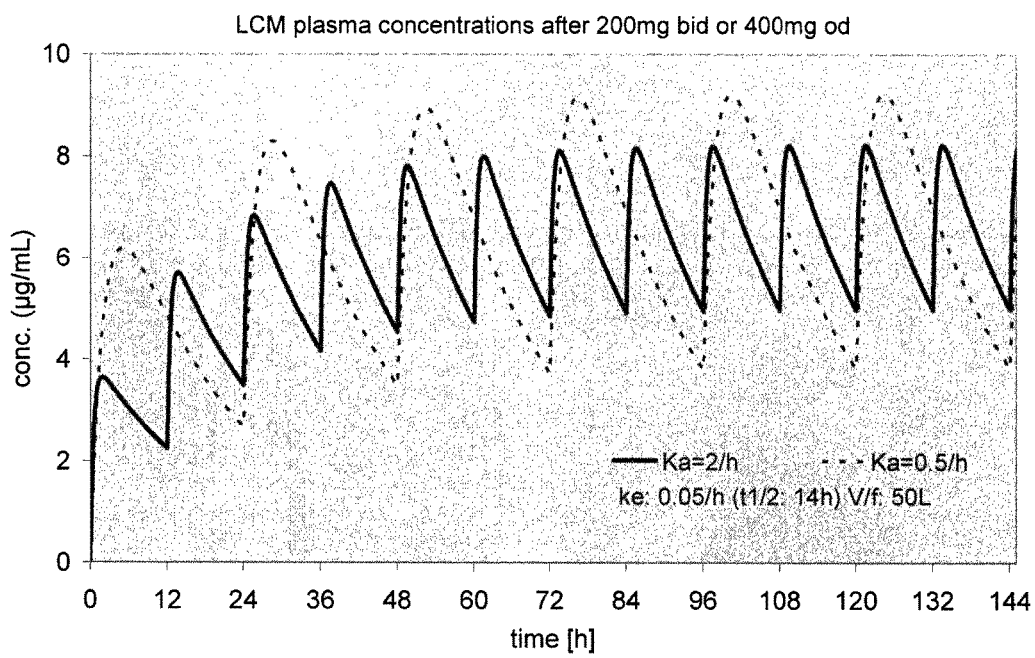

FIG. 4: Model calculation of profile of lacosamide pharmacokinetics (A), therapeutic effect in terms of reduction of seizure frequency (B), and adverse event(s) (incidence of dizziness) (c) as a function of time after multiple doses of a MR formulation (400 mg/day, administration once a day, constant dosing interval 24 h, rate constant ka of 0.5/h) compared to a solid IR formulation (400 mg/day, administration 200 mg bid, constant dosing interval 12 h, ka of 2/h).

Figure 5A:
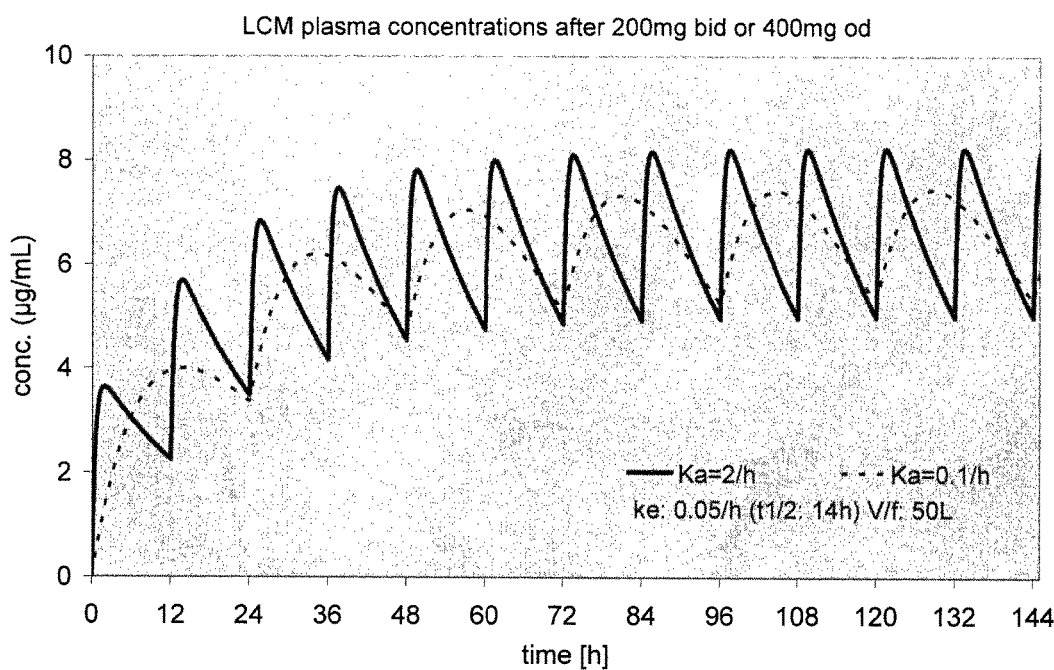
Figure 5B:
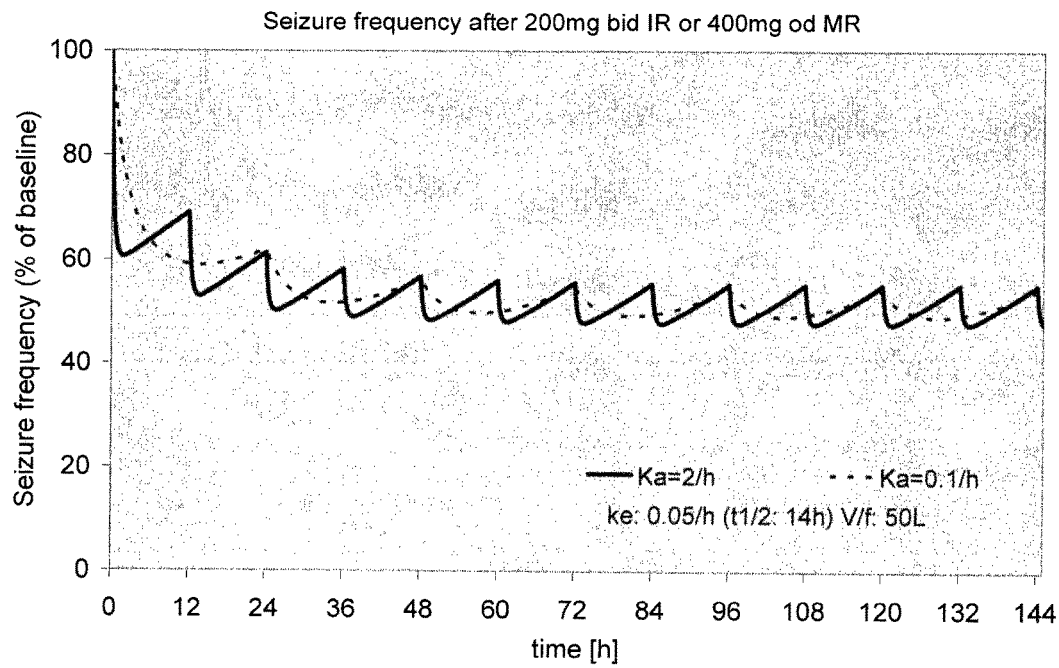

FIG. 5: Model calculation of profile of lacosamide pharmacokinetics (A), therapeutic effect in terms of reduction of seizure frequency (B), and adverse event(s) (incidence of dizziness) (c) as a function of time after multiple doses of a MR formulation (400 mg/day, administration once a day, constant dosing interval 24 h, rate constant ka of 0.1/h) compared to a solid IR formulation (400 mg/day, administration 200 mg bid, constant dosing interval 12 h, ka of 2/h).

Figure 6:
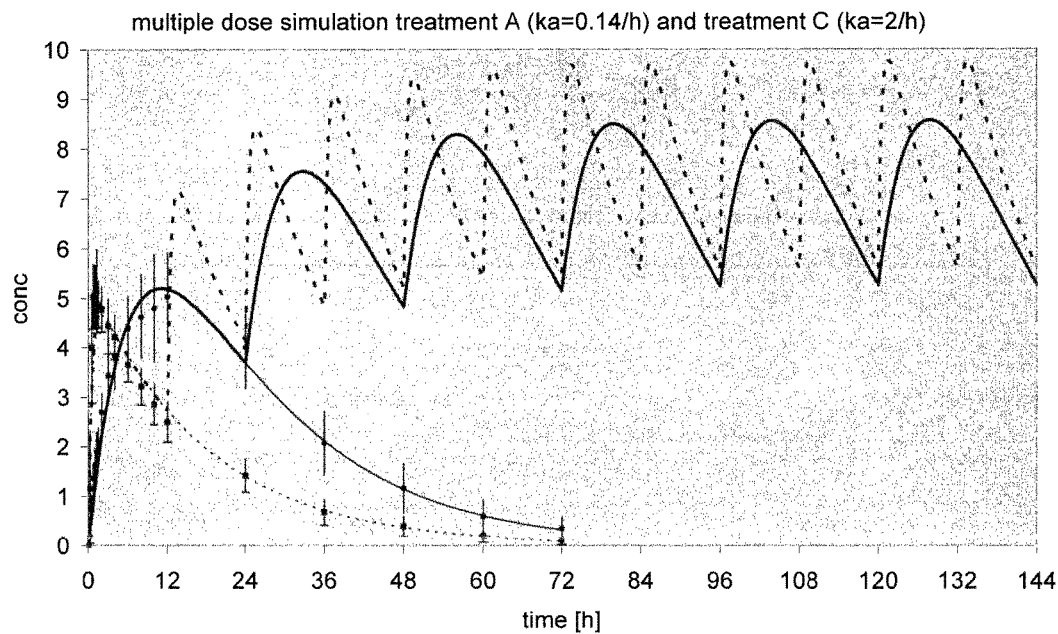

FIG. 6: Model calculation of profile of lacosamide pharmacokinetics as a function of time after multiple doses of 400 mg lacosamide once a day with rate constant ka=0.14/h for MR formulation of Example 19 (treatment A, ka=0.14/h) and Example 6 (treatment C, ka=2/h), as determined in the phase I trial of Example 2.

FIG. 7: PK-PD correlation (predicted vs. measured values) for the change of seizure frequency (N=3055 samples).

FIG. 8: Achievable decrease of the daily number of seizures (%) in relation to daily lacosamide dose (based on results of Emax model)

DETAILED DESCRIPTION OF THE INVENTION

Treatment of epilepsy with lacosamide is generally well tolerated up to daily doses of about 400-600 mg/day. The most frequent side effects are dizziness, headache, diplopia and nausea, in decreasing order.

Despite the good overall anticonvulsive efficacy and tolerability of lacosamide, the side effects of lacosamide sometimes limit the dose to be administrated. In patients with severe and/or pharmacoresistant seizures, a further increase of the lacosamide dose to be administered would be desirable. For example, a once daily administration of lacosamide would require higher single doses to be given and hence would increase the risk of side effects unless the side effect profile of the once daily formulation is improved.

There is thus a need for lacosamide formulations having an improved (i.e. decreased) side effect/efficacy ratio and benefit/risk ratio, and a need for methods of using such formulations, such formulations and methods thereby offering the option for treatment regimens with increased doses of lacosamide. These improved formulations containing increased doses of lacosamide could be administered once daily, and would offer an additional advantage for patients compared to the presently available immediate release formulations for twice daily use.

The twice daily administration of prior art oral immediate release (IR) lacosamide formulations results in a rapid increase of lacosamide plasma concentration by absorption from the intestine, followed by a decline caused by excretion and/or metabolic degradation. Upon repeated administration of an oral immediate release formulation (at a constant dosing interval of, for instance, about 12 h), steady-state plasma concentrations "fluctuate" around a constant mean concentration, having a maximum steady state plasma concentration of lacosamide (Cmax, ss, "peak"), and a minimum state plasma concentration of lacosamide (Cmin, ss, "trough"), which can be characterized by the peak to trough fluctuation (PTF).

We have found that the side effect profile can be improved, by an oral modified release (MR) formulation of lacosamide, and methods of use thereof, wherein the clinical efficacy in the treatment of epilepsy can be maintained. "Improvement" means e.g. a decreased incidence of side effects of lacosamide.

We have surprisingly found that the incidence of side effects of lacosamide directly correlates with the maximum steady state plasma concentration of lacosamide Cmax (Example 1), while the efficacy of lacosamide in treating epilepsy is predominantly associated with the steady state AUC,ss (area under the curve), i.e., with the total amount of lacosamide absorbed after repeated administration (Example 54).

Figure 5C:
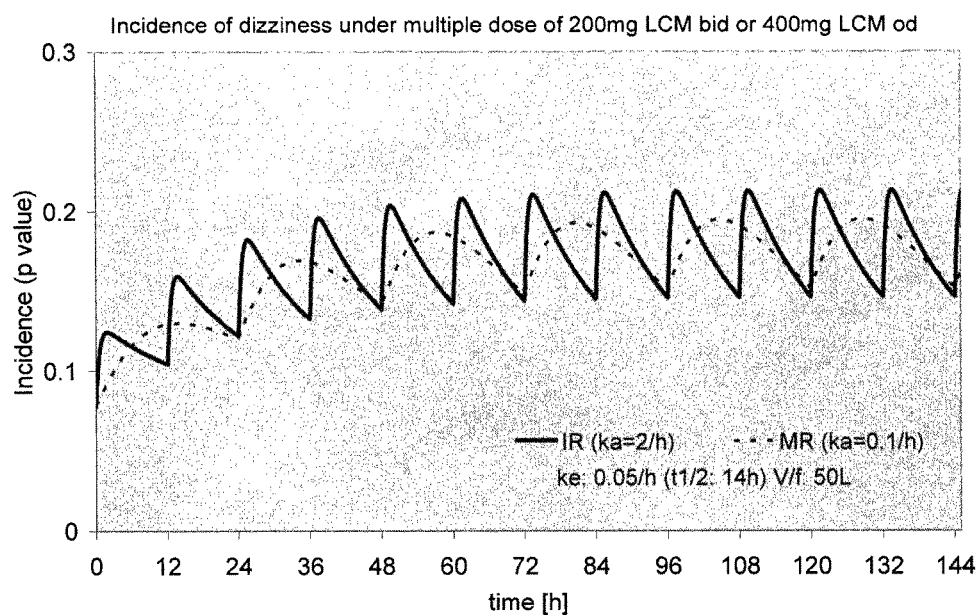

We have discovered that a solid oral MR lacosamide formulation showing the same AUC as the immediate release tablet formulation but having decreased Cmax (and a decreased PTF) and delayed time Tmax of reaching the Cmax would provide essentially the same clinical efficacy of lacosamide but an improved side effect profile (decreased incidence of side effects) after twice a day administration compared to the immediate release formulation. In addition, such a modified release formulation and method of use would offer the opportunity to increase the daily dosage of lacosamide while maintaining the incidence of side effects of an IR formulation with a lower drug load (FIG. 5C). Moreover such a modified release formulation allows for a once daily administration of lacosamide.

In a phase I trial (Example 2, FIG. 1), we have determined the pharmacokinetics of lacosamide for MR formulations and a comparative lacosamide immediate release IR formulation.

Based upon the finding that side effects are related to Cmax (Example 1), whereas efficacy is primarily related to AUC (Example 54), and based on the results of the phase I trial (Example 2), we have performed a model calculation (model simulation) for determination of pharmacokinetic parameters Cmax, Cmin, AUC, PTF and Tmax for repeated administration of a solid oral lacosamide formulation (Examples 3 and 4). By the model simulation, we determined a lacosamide absorption profile and thereby pharmacokinetic release profiles of solid lacosamide MR formulations leading to a reduced Cmax (and a reduced PTF) and delayed time Tmax of reaching the Cmax, compared with a comparative solid lacosamide IR formulation. For example, an optimum release profile of a lacosamide MR formulation resulting in (i) a minimized peak-to-trough fluctuation of plasma concentration, and
(ii) a predetermined AUC has been determined.

In the next step, we calculated the incidence of adverse effects (side effects), such as dizziness, of such optimized absorption profile, based on the correlation between the incidence of adverse effects and maximum plasma concentration (peak plasma concentration) of lacosamide found after the analysis of previous clinical studies. We discovered that a release profile having reduced peak-to-trough fluctuations of lacosamide plasma concentration results in a reduced incidence of adverse effects, compared with side effects of prior art lacosamide formulations (Example 3).

Hence, the present invention provides a modified release formulation of lacosamide for oral administration and method of use thereof with a decreased maximum plasma concentration Cmax,ss, a decreased peak-trough fluctuation (PTF), an increased Cmin,ss and a delayed Tmax,ss while essentially maintaining the overall exposure of the patient to lacosamide, expressed by the AUC,ss, of the formulation, compared with a comparative lacosamide IR formulation.

By the reduced PTF (reduced Cmax), the solid lacosamide MR formulation for oral administration, leading to an in-vivo lacosamide absorption profile and having a release profile determined by the simulation of the present invention, provides an improved side effect profile (in particular reduced incidence of dizziness), compared with an IR formulation. The fact that the release profile provides a similar exposure indicates that the clinical efficacy is similar to that of an IR formulation.

In this patent application, wherever three alternative dissolution criteria are stated, the formulation of the invention meets at least one, more preferably at least two, and most preferably all three of the stated dissolution criteria.

By the model simulations of Examples 3 and 4, we surprisingly found that, for example, for a lacosamide formulation showing release of lacosamide from said formulation in an amount which leads to an in vivo absorption of lacosamide in (a) an amount of about 8.5 wt-% to about 50 wt-% of lacosamide relative to the total lacosamide content of the formulation within 1 h,
(b) an amount of about 15 wt-% to about 70 wt-% of lacosamide relative to the total lacosamide content of the formulation within 2 h, and/or
(c) an amount of about 28 wt-% to about 90 wt-% of lacosamide relative to the total lacosamide content of the formulation within 4 h, a steady-state peak-to-trough fluctuation (PTF, ss) can be observed after once a day administration at a dosing interval of 24 h that is in the same range as the PTF, ss which is obtained after the immediate release lacosamide formulation given twice a day at a dosing interval of 12 hours. Hence, the MR formulation allows for a once daily administration and a greater convenience while providing the same efficacy without increasing side effects.

Convenient lacosamide once-daily formulations are those which after administration to the human body release lacosamide in amounts leading to an in vivo absorption rate constant of absorption ($k_a$) of between about 0.1/h to about 0.5/h, or less. Respective relative lacosamide absorption rates can be taken from table 4. For example, such a preferred modified release formulation would release lacosamide in amounts which provides in vivo absorption rates after one hour of administration of between about 9.5% and about 39.2% and after two hours between about 18.1 and about 63.3% of lacosamide relative to the total amount of lacosamide administered. One embodiment of the present invention is thus a lacosamide formulation which after administration to the human body leads to an in vivo absorption rate which meets at least four, preferably five, six, seven, eight and preferably all of the following absorption rates relative to the total amount of lacosamide administered (Table A):

TABLE A (a) within one hour about 9.5 to about 39%
(b) within two hours about 18 to about 63%
(c) within 3 hours about 26 to about 78%
(d) within 4 hours about 33 to about 87%
(e) within 6 hours about 45 to about 95%
(f) within 8 hours about 55 to about 98%
(g) within 10 hours about 63 to about 99%
(h) within 12 hours about 70 to about 99.8%
(i) within 18 hours >83.5%

More preferred are those lacosamide once daily formulations which release lacosamide in amounts leading to an in vivo absorption in humans with a rate constant of absorption ($k_a$) of between about 0.1/h to about 0.3/h. Respective absorption rates over time are summarized in table 4 herein. One embodiment of the present invention is a lacosamide formulation which after administration to the human body provides an in vivo absorption rate which meets at least four, preferably five, six, seven, eight and preferably all of the following absorption rates relative to the total amount of lacosamide administered (Table B):

TABLE B (a) within one hour about 9.5 to about 26%
(b) within two hours about 18 to about 45%
(c) within 3 hours about 26 to about 59%
(d) within 4 hours about 33 to about 70%
(e) within 6 hours about 45 to about 83.5%
(f) within 8 hours about 55 to about 91%
(g) within 10 hours about 63 to about 95%
(h) within 12 hours about 70 to about 97%
(i) within 18 hours about 83.5 to about 99.5%

Even more preferred are those lacosamide once daily formulations which release lacosamide in amounts leading to an in vivo absorption in humans with a rate constant of absorption ($k_a$) of between about 0.1/h to about 0.2/h. Respective absorption rates over time are summarized in table 4 herein. One embodiment of the present invention is thus a lacosamide formulation which after administration to the human body leads to an in vivo absorption rate which meets at least four, preferably five, six, seven, eight and preferably all of the following absorption rates relative to the total amount of lacosamide administered (table C):

TABLE C (a) within one hour about 9.5 to about 18%
(b) within two hours about 18 to about 33%
(c) within 3 hours about 26 to about 45%
(d) within 4 hours about 33 to about 55%
(e) within 6 hours about 45 to about 70%
(f) within 8 hours about 55 to about 80%
(g) within 10 hours about 63 to about 86.5%
(h) within 12 hours about 70 to about 91%
(i) within 18 hours about 83.5 to about 97%

Such a formulation provides an in vivo peak to trough fluctuation after once a day administration of about the same size as the lacosamide immediate release formulation given twice daily (table 5).

We also found surprisingly that the in vivo absorption of lacosamide shows a direct and very close correlation to the in vitro dissolution profile of a laosamide formulation when measured according to USP (edition 24) method <711>, dissolution apparatus 2, in 900 mL of 0.1N HCl at 50 rpm such that the rate constant of absorption $k_a$ is about identical to the rate constant of dissolution $k_{diss}$ for a lacosamide formulation when measured at the above conditions at 50 rpm. This is due to the fact that lacosamide is being absorbed by the human body very rapidly and completely, such that the rate constant of absorption $k_a$ is substantially dependent only from the release of lacosamide from the galenic formulation, which can be measured under defined in-vitro dissolution conditions described herein.

Accordingly, one embodiment of the present invention relates to lacosamide modified release formulations which show a rate constant of dissolution $k_{diss}$ of between about 0.1/h to about 0.5/h, preferably of between about 0.1/h and about 0.3/h, and more preferably of between about 0.1/h and about 0.2/h, and even more preferably between about 0.1/h and about 0.15/h when measured according to USP (edition 24) method <711>, dissolution apparatus 2, in 900 mL of 0.1N HCl at 50 rpm. In one aspect, the modified lacosamide formulations of the present inventions releases lacosamide in amounts reflecting about the absorption rates given in tables A, B and C herein, when measured in-vitro according to USP (edition 24) method <711>, dissolution apparatus 2, in 900 mL of 0.1N HCl at 50 rpm.

We also found that the in vivo absorption of lacosamide correlates to the in vitro dissolution profile of a laosamide formulation when measured according to USP (edition 24) method <711>, dissolution apparatus 2, in 900 mL of 0.1N HCl at 75 rpm as further disclosed herein. Accordingly, one embodiment of the present invention relates to lacosamide modified release formulations which show a rate constant of dissolution $k_{diss}$ of between about 0.1/h to about 0.5/h, preferably of between about 0.1/h and about 0.3/h, and even more preferably of between about 0.1/h and about 0.2/h when measured according to USP (edition 24) method <711>, dissolution apparatus 2, in 900 mL of 0.1N HCl at 75 rpm.

It is well known to a person skilled in the art that depending on the applied formulation technology and the recipients used, a modified release formulation may also show an increased initial release ("burst") of lacosamide, for example of about 5 to 25%, of the total amount of lacosamide in the formulation. Such formulations with an initial burst of lacosamide within the first hour are encompassed by the present invention so long as the dissolution rates at the time points (e.g. at 2, 4 or 8 hours etc) are within the ranges further disclosed and claimed herein. An initial burst effect may be caused, for example, by lacosamide being attached to the surface of the formulation during the manufacturing of the formulation. A controlled burst may be achieved, for example, by applying an immediate release outer coating to a modified release formulation, wherein said immediate release coating comprises a predefined amount of lacosamide to be released as burst. Preferably the initial burst of lacosamide compared to the preferred dissolution profiles as disclosed herein are below 30%, preferably below 20%, more preferably below 10% and even more preferably below 5% of the total lacosamide content of the formulation. Most preferred are those lacosamide formulations which show an in-vitro release rate of lacosamide which fully meet the in-vitro dissolution profiles described herein.

We surprisingly found that, for example, a lacosamide formulation showing an in-vitro release of lacosamide of
(a) an amount of about 8.5 wt-% to about 50 wt-% of lacosamide relative to the total lacosamide content of the formulation within 1 h,
(b) an amount of about 15 wt-% to about 70 wt-% of lacosamide relative to the total lacosamide content of the formulation within 2 h, and/or
(c) an amount of about 28 wt-% to about 90 wt-% of lacosamide relative to the total lacosamide content of the formulation within 4 h,
when the in-vitro release of lacosamide is preferably measured according to USP (edition 24) method <711>, dissolution apparatus 2, in 900 mL of 0.1N HCl at 50 rpm, or at 75 rpm, preferably at 75 rpm, shows the desired in vivo absorption profile as described in tables A and 4 of this specification such that a steady-state peak-to-trough fluctuation (PTF, ss) of between about 8.5 and 32% can be observed when lacosamide is administered twice a day at a dosing interval of 12 h, compared to a PTF, ss of the immediate release lacosamide formulation of between about 45 and 50%.

Accordingly, one aspect of the present invention relates to a solid pharmaceutical composition for the once daily oral administration of lacosamide which provides a dose-normalized steady state maximum concentration of lacosamide $C_{max,ss,norm}$ of between about 0.016 and about 0.023, or between about 0.018 and about 0.023, preferably between about 0.016 and about 0.0215, or between about 0.018 and 0.0215 µg lacosamide/ml plasma/mg lacosamide administered per dose in patients with an average distribution volume of 50 L (tables 5 and 7).

By way of example, for a once daily delivery of 400 mg per dose typical Cmax, steady state plasma concentrations reached after administering the modified release formulations of the present invention are between about 6.4 and 9.2 µg/ml plasma, preferably between about 7.2 and 9.2 µg/ml plasma, or between 6.4 and 8.6 µg/ml plasma, more preferably between about 7.2 and about 8.6 µg/ml plasma in patients with an average distribution volume of 50 L. For a once daily delivery of 600 mg per dose typical Cmax, ss plasma concentrations reached after administering the modified release formulations of the present invention would be between about 9.6 and 13.8 µg/ml plasma, preferably between about 10.8 and 13.8 µg/ml plasma, or between about 9.6 and 12.9 µg/ml plasma, more preferably between about 10.8 and 12.9 µg/ml plasma in patients with an average distribution volume of 50 L.

Another aspect of the present disclosure relates to a solid pharmaceutical composition for the once daily oral administration of lacosamide that provides a time point $T_{max,ss}$ for reaching the maximum plasma concentration of lacosamide after drug administration in steady state of between 4 and 10 hours, preferably between about 5 and 9 hours, more preferably between about 6.5 and 9 hours, or between about 6.8 and 8.6 hours (tables 5 and 7). By comparison, immediate release lacosamide formulations given twice daily result in a Tmax,ss of about 1.5 hours.

Another aspect of the present disclosure relates to a solid pharmaceutical composition for the once a day oral administration of lacosamide that provides a dose-normalized AUC in the steady state (AUC, ss, norm) of between about 0.36 and 0.42 µg/ml plasma/mg lacosamide administered per dose, preferably of about 0.400 µg/ml plasma/mg lacosamide per dose in patients with an average distribution volume of 50 L (tables 5 and 7).

Another aspect of the present disclosure relates to a solid pharmaceutical composition for the once daily oral administration of lacosamide that delivers lacosamide to the animal body such that the peak-trough fluctuation (PTF) is below 82%, preferably below 70%, more preferably below 55%, and even more preferably below 45%. In fact, based on the present disclosure, example formulations have been provided that yield a PTF of between about 45 and 54%, as can be predicted from initial clinical trials.

Another aspect of the present invention relates to a solid pharmaceutical composition for the oral administration of lacosamide resulting in dose normalized minimum steady state plasma levels $C_{min,ss,norm}$ of between 0.0095 and 0.015, and preferably between 0.01 and 0.014 µg lacosamide/ml plasma/mg lacosamide per dosage unit in patients with an average distribution volume of 50 liters.

One aspect of the present invention relates to a solid pharmaceutical composition for the once daily oral administration of lacosamide which provides
(a) a dose-normalized steady state maximum concentration of lacosamide $C_{max,ss,norm}$ of between about 0.016 and about 0.023, or between about 0.018 and about 0.023, preferably between about 0.016 and about 0.0215, or between about 0.018 and 0.0215 µg lacosamide/ml plasma/mg lacosamide administered per dose in patients with an average distribution volume of 50 L,
(b) a dose-normalized steady state minimum plasma concentration $C_{min,ss,norm}$ of between 0.0095 and 0.015, and preferably between 0.01 and 0.014 µg lacosamide/ml plasma/mg lacosamide per dosage unit in patients with an average distribution volume of 50 liters, and
(c) a time point Tmax, ss for reaching the maximum plasma concentration of lacosamide after drug administration in steady state of between 4 and 10 hours, preferably between about 5 and 9 hours, more preferably between about 6.5 and 9 hours, or between about 6.8 and 8.6 hours.

Another aspect of the present invention relates to a method for the prevention, alleviation, and/or treatment of a disease of the central nervous system comprising administration twice daily of a lacosamide formulation showing release of
(a) an amount of about 8.5 wt-% to about 50 wt-%, of lacosamide relative to the total lacosamide content of the formulation within 1 h,
(b) an amount of about 15 wt-% to about 72 wt-% of lacosamide relative to the total lacosamide content of the formulation within 2 h, and/or
(c) an amount of about 28 wt-% to about 95 wt-% of lacosamide relative to the total lacosamide content of the formulation within 4 h,
when the in-vitro release of lacosamide is preferably measured according to USP (edition 24) method <711>, dissolution apparatus 2, in 900 mL of 0.1N HCl at 75 rpm. a steady-state peak-to-trough fluctuation (PTF, ss) of between about 8.5 and 32% can be observed when lacosamide is administered twice a day at a dosing interval of 12 h, compared to a PTF, ss of the immediate release lacosamide formulation of between about 45 and 50%.

Another aspect of the present invention relates to such a method for the prevention, alleviation, and/or treatment of a disease of the central nervous system wherein the disease is selected from pain, epilepsy, disorders associated with epileptic seizures, essential tremor, bipolar disorder, schizophrenia, obsessive compulsive disorders, dyskinesia, or hyperexcitability disorders.

Another aspect of the present invention relates to such a method for the prevention and/or treatment of epilepsy or conditions associated with epileptic seizures.

Another aspect of the present invention relates to such a method for the prevention, alleviation, and/or treatment of a disease of the central nervous system wherein the incidence of side effects is reduced compared to an immediate release formulation comprising the same amount of lacosamide and releasing more than 80% of lacosamide within 30 minutes when measured according to USP (edition 24), method <711>, dissolution apparatus 2, in 900 mL of 0.1N HCl at 75 rpm.

Another aspect of the present invention relates to such a method for the prevention, alleviation, and/or treatment of a disease of the central nervous system wherein the seizure frequency is reduced compared to the seizure frequency achieved by the administration of an immediate release formulation comprising the same amount of lacosamide, and releasing more than 80% of lacosamide within 30 minutes when measured according to USP (edition 24), method <711>, dissolution apparatus 2, in 900 mL of 0.1N HCl at 75 rpm.

Another aspect of the present invention relates to such a method for the prevention, alleviation, and/or treatment of a disease of the central nervous system wherein the formulation is administered twice daily at a dosing interval tau of about 12 h.

Definitions:

$k_a$ is the rate constant of absorption which can be used to describe a first order absorption of a drug by the differential equation $dC(t)/dt = -k_a C(t)$ for an absorption, wherein C(t)=lacosamide concentration at time t after administration, $K_{diss}$ is the rate constant of dissolution which can be used to describe the dissolution of a drug from a formulation following a first order kinetic by the differential equation $dD(t) = k_{diss}*D(t)$; D(t) is the amount lacosamide dissolved (% of the total amount); t is the time (h) after start of the dissolution experiment. The dissolved amount D(t) of a lacosamide modified release formulation can be described as the sum of a burst effect (if present) and the modified release of lacosamide according to the formula $D(t) = burst+(100-burst)*(1-exp(-k_{diss}*t))$ with burst being the initially (within <1 hour) dissolved amount in % of the total lacosamide amount in the formulation.

"Cmax" is the maximum concentration of lacosamide reached in the plasma.

"Cmax,ss" is the maximum concentration of lacosamide reached in the plasma in the steady state.

"Cmax,ss,norm" is Cmax,ss normalized by dividing Cmax, ss by the lacosamide amount contained in a single dosing unit. For example, Cmax,ss, norm for a twice daily 200 mg formulation will be determined by dividing Cmax,ss by 200 mg.

"Cmin" is the minimum concentration of lacosamide reached in the plasma.

"Cmin.ss" is the minimum concentration of lacosamide reached in the plasma in the steady state.

"Cmin,ss,norm" is the minimum steady state plasma concentration of lacosamide Cmin,ss, measured after repeated administration of lacosamide, normalized by dividing Cmin,ss by a single dosing unit. For example, Cmax,ss,norm for a twice daily 200 mg formulation will be determined by dividing Cmin, ss by 200 mg.

"Tmax" (or "tmax") is the period of time between the administration of a given dose of lacosamide and the point in time when Cmax is reached.

"Tmax,ss" (or "tmax,ss") refers to the period of time between the administration of a given dose of lacosamide and the point in time when Cmax, ss is reached.

"AUC,tau" is the Area Under the concentration time Curve within a dose interval tau.

"AUC,tau,ss" is the Area Under the concentration time Curve within a dose interval tau under steady state conditions.

"AUC,tau,ss,norm" refers to the Area Under the Curve in steady state conditions, and normalized by the dosing unit administered. It reflects the total amount of lacosamide administered, and will be determined by AUC,tau,ss, norm=AUC,tau,ss/dose.

"PTF" is the peak to trough fluctuation and indicates the fluctuations of the concentration of lacosamide in plasma. It will be determined by applying the following formula: PTF=(Cmax,ss-Cmin,ss)/AUC,tau,setau, with tau being the applicable dosing interval in hours.

"Steady state" means an equilibrium after repeated administration of a medicinal agent in which the amount of active principle (active agent) delivered corresponds to the amount eliminated in a dosing interval, resulting, for instance, in a constant plasma concentration. In the oral formulations of the present invention, "steady state" of repeated doses includes fluctuations between a maximum value (e.g. Cmax,ss) and a minimum value (e.g. Cmin,ss), wherein the maximum value and the minimum value (such as, Cmax,ss and Cmin,ss) are essentially constant over several dosing intervals. "Steady state" can, for instance, be reached by administration of the oral formulation comprising a predetermined amount of active agent at a constant dosing interval.

The term "average distribution volume" or "average distribution volume of 50 liters" in connection with pharmacokinetic values like Cmax, Cmin, or AUC reflects that pharmacokinetic parameters determined for a given formulation in a different distribution volume (e.g., in other patient populations) can be normalized to the "average distribution volume" or "average distribution volume of 50 liters" by multiplying with the respective distribution volume and dividing by the average distribution volume.

The term "about" as used in this specification means that a given value can deviate up to ±10% of the stated value.

"USP (edition 24) method <711>" refers to an in-vitro dissolution test for a pharmaceutical composition as described in method 711 of the US Pharmacopeia, Edition 24, which is incorporated herein by reference.

The term "derivative" of a particular excipient class as used for example in "cellulose derivative" or vinyl acetate "derivative" includes esters, ethers and amides of suitable functional groups, as applicable, and as known to those skilled in the art.

The term "animal" as used herein refers in particular to mammals. "Animal" as used herein includes human beings.

The term "lacosamide" refers to (R)-2-Acetamido-N-benzyl-3-methoxypropionamide. Lacosamide may have an enantiomeric purity of at least 90% of the (R) enantiomer, preferably at least 95%, at least 97%, at least 98% or even at least 99% of the (R) enantiomer. The term "lacosamide" includes amorphous forms, crystals, co-crystals, and polymorphs of lacosamide.

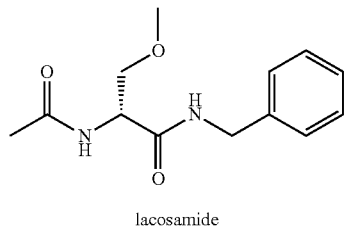 [SMILES: COC[C@@H](NC(C)=O)C(=O)NCc1ccccc1]

lacosamide

The term "co-crystal" of lacosamide refers to co-crystals formed from lacosamide with a second compound, wherein the lacosamide co-crystals differ in the crystal structure and associated properties from "mono"-crystals formed solely by lacosamide and/or by said second compound or acid alone. The second compound included in the co-crystal may or may not have pharmacological activity. Examples of co-crystals are those formed from lacosamide and trimesic acid or lacosamide and fumaric acid.

As used herein, the term "powder" includes a dry, finely divided chemical, for instance a dry, finely divided active ingredient. The term powder includes compositions. The powder may be an intimate mixture of at least one active ingredient and at least one excipient. A powder may be formulated for internal or external use. Powder particles may have a mean diameter from about 1 µm to about 500 µm. Also included is a powder as defined in United States Pharmacopeia (USP) definition <1151>, which is incorporated herein by reference. As used herein, the term "granule" includes an aggregation/conglomeration of distinct solid powder particles to larger multiparticle entities. The granule may be coated. In particular, the granule of the present invention may be coated, preferably by a functional coating, as described herein. Granules may have a mean diameter from about 50 µm to about 2000 µm or from about 100 µm to about 1000 µm. The term "granule" includes a pellet. Also included is a granule as defined in USP <1151>, which is included herein by reference.

A "sieving test" of the granules/powders was performed and analyzed according to 2.9.12 European Pharmacopoeia (EP) and 2.9.38 EP. $D_{10}$, $D_{50}$ and $D_{90}$, respectively, represent mass diameters correlating to 10%, 50% and 90%, respectively, of the mass of the investigated granules/powders.

The term "pellet" refers to small solid typically spherical masses comprising an active ingredient and optionally at least one excipient. The pellet may be produced by granulation, compression and/or molding. Pellets may have a mean diameter from about 100 µm to about 3000 µm or from about 200 µm to about 2000 µm. Also included is a pellet as defined in USP <1151>, which is incorporated herein by reference.

The term "tablet" includes a solid dosage form containing at least one medicinal substance (active agent) and optionally at least one pharmaceutically acceptable diluent and/or excipient. A tablet may comprise at least one active ingredient and typically diluent (filler), binder, and lubricant. In the present invention, comparative IR tablets may comprise a disintegrating agent. MR tablets of the present invention may comprise a matrix retardation agent, and/or may comprise a functional coating, as described herein. Tablets of the present invention, in particular coated tablets or matrix tablets, may have a size in the range of about 5 mm to about 30 mm, preferably from about 7 mm to about 20 mm. If the tablet has an essentially round shape, the size refers to the diameter of the tablet. If the tablet has an oblong shape, the size indicates the size of the longitudinal axis unless specifically stated otherwise. The size may be at least about 5 mm, at least about 6 mm, at least about 7 mm, at least about 8 mm, at least about 9 mm, or at least about 10 mm. The size may be at the most about 20 mm or at the most about 30 mm. If the tablet has an oblong shape, typical sizes of the longitudinal axis may be between about 7 mm and 30 mm, preferably between about 10 mm and 20 mm, and typical sizes of the traverse axis are between about 4 mm and 12 mm, preferably between about 6 mm and 10 mm. Also included is a tablet as defined in USP <1151>, which is incorporated herein by reference.

The term "minitablet" refers to a subform of tablets. A minitablet may be a tablet with typical diameter ranging from 1 mm to 4 mm and a height ranging from 1 mm to 4 mm.

The term "capsule" refers to a solid dosage form in which the drug is enclosed within either a hard or soft soluble container or "shell." The container or shell can be formed from gelatin, starch and/or other suitable substances. Also included is a capsule as defined in USP <1151>, which is incorporated herein by reference.

The terms "multiple dosing units" and "multiple unit dosage forms" are used interchangeably herein and refer to small-sized dosing forms with a size of below about 4 mm, preferably below about 3 mm, more preferably below about 2.5 mm, or even below about 2 mm. "Multiple dosing units" or "multiple unit dosage forms" contain amounts of lacosamide below the amount of a single dose of lacosamide to be administered at a given time, i.e. usually below 25 mg, preferably below 20 mg, below 15 mg, below 10 mg, even more preferably below 5 mg, 4 mg, 3 mg, 2 mg or below 1 mg of lacosamide per physical entity. Accordingly, the administration of a single dose of lacosamide comprises the administration of multiple of such multiple unit dosage forms. "Multiple dosing units" or "multiple unit dosage forms" comprise powders/particles, pellets, minitablets, or granulates, which may be covered with coatings prior to further processing and/or administration, and/or which may be packed into sachets or capsules. "Multiple dosing units" and "multiple unit dosage forms" may be compressed to dispersible tablets consisting of powders/particles, pellets, minitablets, or granulates as further defined herein. Each entity of the "multiple dosing units" (e.g. each pellet, granulate or mini-tablet) is preferably a full functional unit showing in average the in-vitro dissolution properties further defined in this specification.

The term "single unit dosage" or "single unit dosage form" as used herein refers to formulations of lacosamide usually containing at least about half the amount of a single dose of lacosamide to be administered at a given time, i.e. at least 25 mg lacosamide, more preferably at least about 50 mg or 100 mg, or even more than about 200 mg of lacosamide. The average size of a single unit dosage form is usually at least about 4 mm, more preferably at least about 5 mm per physical entity. Single unit dosage forms are physical entities individually showing the dissolution properties disclosed herein. Upon disintegration single unit dosage forms such as e.g. tablets or dragees, usually do not disperse into separate functional units.

In the present invention, the terms "release controlling agent" and "agent capable of retarding release" describe an agent present in a solid pharmaceutical formulation comprising an active agent such as lacosamide, wherein the release controlling agent is capable of retarding the release of the active agent from the formulation, compared with an immediate release formulation of the active agent. If present in the matrix of a solid formulation, the release controlling agent is termed "matrix retardation agent" or "matrix controlling agent". In vitro release may be measured by the USP (edition 24) method <711>, as described herein.

In the present invention, a matrix of a solid formulation, said matrix containing a matrix retardation agent, is termed herein "controlled release matrix" or "modified release matrix".

The term "matrix tablet" refers to a tablet comprising a "controlled release matrix" or "modified release matrix" as defined herein. A "matrix tablet" may or may not comprise a functional coating.

In the present invention, a coating and/or film coat of a solid formulation, said coating and/or film coat comprising a release controlling agent, is termed herein "release controlling layer" or "release modifying layer".

The term "functional coating" in the context of the present disclosure refers to a release controlling layer, in particular a lacosamide release controlling layer, surrounding a core, such as a lacosamide containing matrix.

The term "non functional coating" or "non-functional film coat" in the context of the present disclosure refers to a coating which has essentially no material impact on the release of lacosamide from the formulation. In particular, a "non-functional film coat" or "non-functional coating" relates to a coating of a solid formulation comprising an active agent such as lacosamide, wherein the coating essentially does not retard the release of the active agent from the formulation, compared with the solid formulation without the coating. A "non functional coating" or "non-functional film coat" may nevertheless include some functions unrelated to the lacosamide dissolution, like taste, colouring, or physical integrity of the tablet.

The terms "controlled release formulation" or "modified release formulation" (or in its abbreviated form, "MR formulation") as used interchangeably herein, describe a solid pharmaceutical formulation comprising an active agent such as lacosamide, and a release controlling agent, wherein the release controlling agent is capable of retarding the release of the active agent from the formulation, compared with an immediate release formulation of the active agent.

The term "immediate release formulation", as used herein, refers to a solid formulation comprising an active agent, such as lacosamide, which immediate release formulation releases at least 90 wt-%, at least 95 wt-% or at least 97 wt-% of the total content of the active agent within 15 min or 30 min, when the in-vitro release of the active agent is measured according to USP (edition 24) method <711>, dissolution apparatus 2, in 900 mL of 0.1N HCl at 75 rpm.

As used herein, "repeated administration" or "repeated dosing" refers to administration or dosing over a period of 2 or more days. "Repeated administration" or "repeated dosing" may refer to administration or dosing over a period of at least 2 days, at least 3 days, at least 4 days, at least 5 days, at least 6 days, at least 7 days (one week), or more days, or at least 2 weeks, at least 3 weeks, at least 4 weeks (one month), or more weeks, at least 2 months, at least 3 months, or more months. In particular, "repeated administration" or "repeated dosing" refers to dosing over a period sufficient to reach the steady state plasma concentration of lacosamide, for instance over a period of at least 3 days, at least 4 days, at least 5 days, at least 6 days, at least 7 or more days, or any longer period as indicated herein. The term "low-substituted hydroxypropyl cellulose" refers to a low-substituted hydroxypropyl ether of cellulose. Compared to hydroxypropyl cellulose, low-substituted hydroxypropyl cellulose has only a small proportion of the three free hydroxyl groups per glucose subunit converted to a hydroxypropyl ether. When dried at 105° C. for 1 hour, it usually contains not less than 5.0% and not more than 16.0% of hydroxypropoxy groups (—OCH2CHOHCH3).

"Low-substituted hydroxypropyl cellulose" is sparingly or not soluble in water and does therefore not form viscous solutions. Low-substituted hydroxypropyl cellulose is widely used in oral solid-dosage forms. It is primarily used as a disintegrant, and as a binder for tablets and granules in wet or dry granulation.

"Viscosity" as mentioned herein is in particular determined by Ubbelohde capillary viscosity, preferably by the USP (Edition 24) method <911>.

Solid Formulation

In the present invention, formulations of lacosamide have been developed having the desired release profile. Experimental data for lacosamide absorption obtained with a reliable in vitro model of intestinal absorption (USP (edition 24) method <711>, paddle dissolution test) are provided. Two of these controlled release formulations have been assessed in a human pK trial and showed the predicted in vivo properties, i.e. a direct correlation between in vitro dissolution and in vivo absorption and a decrease of overall side effects compared to the immediate release formulations with the same lacosamide content. This demonstrates and confirms that the in vitro model we employed is predictive of in vivo results.

In a human phase I pK trial, we have determined the pharmacokinetics of two lacosamide MR formulations and a comparative lacosamide IR formulation. In this trial, we determined the pharmacokinetic parameters Cmax and Tmax of two MR formulations after administration of a single dose of lacosamide of each of the two MR formulations. The results showed a direct in-vitro in-vivo correlation and demonstrated a delayed absorption of lacosamide with lower peak concentrations of lacosamide for both MR formulations compared to lacosamide IR formulations. Moreover, it was known from previous trials that absorption and elimination (excretion and/or metabolic degradation) of lacosamide can be described by a first order kinetics. In a computer model calculation, the experimentally determined parameters Cmax and Tmax obtained after administration of a single dose of lacosamide from the two modified release formulations are extrapolated to the pharmacokinetic parameters Cmax, Cmin, AUC, PTF and Tmax after multiple dosing. In the computer simulation, we employed an established model of pharmacokinetics, based on a first order kinetics of absorption and elimination, describing (a) fluctuations of plasma concentration, namely an increase of plasma concentration after dosing until the peak concentration is reached, and a subsequent decrease until the next dosing, and (b) accumulation of an active agent after repeated dosing until a steady state in the plasma concentration is reached. As the experimentally determined parameters Cmax and Tmax after single administration of the respective MR formulations can be described by a first order kinetics of absorption and elimination, as required by the computer model, this computer model we employed is predictive for the in vivo parameters Cmax, Cmin, AUC, PTF and Tmax after multiple administration of MR formulations, i.e. in steady state conditions.

From these results it can be concluded that (a) MR formulations can be provided which provide the same efficacy as the IR formulation but a decreased Cmax and PTF values and delayed Tmax, and an improved side effect profile, and (b) that such optimized pK-parameters can be used to predict the in-vitro dissolution profile of suitable solid MR formulations. These solid MR lacosamide formulation for oral administration can be provided in the pharmaceutical dosage form of, for example, a tablet or a coated granule, having a release profile as defined herein.

In one aspect, the present invention provides a controlled release formulation of lacosamide for oral administration. The present invention relates to a solid controlled release formulation of lacosamide for oral administration, wherein
  (a) an amount of about 8.5 wt-% to about 50 wt-% of lacosamide relative to the total lacosamide content of the formulation is released within 1 h,
  (b) an amount of about 15 wt-% to about 72 wt-% of lacosamide relative to the total lacosamide content of the formulation is released within 2 h, and/or
  (c) an amount of about 28 wt-% to about 95 wt-% of lacosamide relative to the total lacosamide content of the formulation is released within 4 h,
when the in-vitro release of lacosamide is preferably measured according to USP (edition 24) method <711>, dissolution apparatus 2, in 900 mL of 0.1N HCl at 75 rpm. In one aspect, all three dissolution criteria (a), (b) and (c) are met by the MR formulation.

The controlled release formulation of lacosamide for oral administration comprises lacosamide and in particular an agent for retarding the release of the lacosamide, as described herein.

The in-vitro release of lacosamide according to USP (edition 24) method <711>, dissolution apparatus 2, in 900 mL of 0.1N HCl at 75 rpm can be regarded as a model of lacosamide release in vivo. The start of the experimental release by the USP (edition 24) method <711> can represent the time of administration to a subject.

In another aspect, the present invention provides a controlled release formulation of lacosamide for oral administration. The present invention relates to a solid controlled release formulation of lacosamide for oral administration, said formulation comprising lacosamide and a release controlling agent, wherein
  (a) an amount of about 8.5 wt-% to about 50 wt-% of lacosamide relative to the total lacosamide content of the formulation is released within 1 h, and/or
  (b) an amount of about 15 wt-% to about 72 wt-% of lacosamide relative to the total lacosamide content of the formulation is released within 2 h,
when the in-vitro release of lacosamide is preferably measured according to USP (edition 24) method <711>, dissolution apparatus 2, in 900 mL of 0.1N HCl at 75 rpm.

In another aspect, the present invention provides a controlled release formulation of lacosamide for oral administration, said formulation comprising lacosamide and a release controlling agent, wherein
  (a) an amount of about 15 wt-% to about 72 wt-% of lacosamide relative to the total lacosamide content of the formulation is released within 2 h, and/or
  (b) an amount of about 28 wt-% to about 95 wt-% of lacosamide relative to the total lacosamide content of the formulation is released within 4 h,
when the in-vitro release of lacosamide is preferably measured according to USP (edition 24) method <711>, dissolution apparatus 2, in 900 mL of 0.1N HCl at 75 rpm.

The solid controlled release lacosamide formulation of the present invention can be provided in the pharmaceutical dosage form of, for example, a tablet, a coated tablet, or a coated granule, wherein coating may be a functional coating, said formulation having a release profile as defined herein.

In the formulation of the present invention, lacosamide may be present in an amount of 20 to 95 wt-%, -%, in an amount of 30 to 50 wt %, in an amount of 50-95 wt %, or in an amount of 70 to 95 wt %.

In the modified release formulations of the present disclosure any polymorphic form or mixtures of polymorphic forms of lacosamide may be used.

In one aspect, the modified release formulation comprises lacosamide in polymorphic Form (I), either essentially in Form (I), or in admixture with Form (II).

A preferred aspect of the present disclosure relates to a solid modified release formulation of lacosamide as further specified herein, wherein lacosamide is essentially in polymorphic Form (I). Compared to Forms (II) and (III), Form (I) offers various advantages such as in manufacturing and handling. Form (I) is considered the thermodynamically most stable form, and forms suspensions during crystallization which are easy to work with.

The term "polymorph" or "polymorphic Form" of lacosamide includes polymorphic forms (I), (II) and (III) of lacosamide, as further defined below.

"Polymorphic form (I)" is characterized by a powder X-ray diffractogram comprising one or more peaks at 8.30; 13.00, 16.65, 21.05, 21.27 and 24.95±0.25 (°2θ), measured with a Cu—Kα irradiation (1.54060 Å). Additional peaks may typically occur at 10.42, 15.62, 17.7, 19.58, 24.27, and 25.39±0.25 (°2θ). Polymorphic form (I) has a melting point of about 144° C.-146° C. in differential scanning calorimetry at a heating rate of 1° C./min in open and closed vials, and can be obtained according to the procedure described in example 1 and 2 of European patent EP 888 289 B1. Suitable methods for producing Form 1 are the crystallization from lacosamide solutions in acetonitrile or methanol, e.g. at about room temperature or below. Polymorphic form (I) may also be obtained by dissolving lacosamide in a solvent, preferably in ethyl acetate; seeding with pure polymorphic form (I) of (R)-2-acetamido-N-benzyl-3-methoxypropionamide; maintaining the suspension at the seeding temperature, then gradually cooling down; washing with a solvent, preferably ethyl acetate and drying (example 54).

"Polymorphic form (II)" of lacosamide is characterized by a powder X-ray diffractogram comprising one or more peaks at: 5.20; 6.74; 10.42; 10.81; 11.06; 12.64; 15.66; and 16.25; all ±0.25 (°2θ), measured with a Cu—Kα irradiation (1.54060 Å). Additional peaks may typically occur at 19.98; 20.80; 21.67; 22.65; 23.27; 23.99; 25.90; and 27.86; all ±0.25 (°2θ), measured with a Cu—Kα irradiation (1.54060 Å). Polymorphic form (II) of lacosamide typically shows melting point peaks splitted between about 140° C. to 145° C. in differential scanning calorimetry at a heating rate of 1° C./min in open and closed vials. Polymorph form (II) of lacosamide is producable for example by crystallizing lacosamide from acetone at about room temperature.

"Polymorph form (III)" of lacosamide is characterized by a powder X-ray diffractogram comprising one or more major peaks at: 8.42; 9.54; 13.14; 16.61; 17.85; 19.52; 20.0; 23.7; and 24.91; all ±0.25 (°2θ), measured with a Cu—Kα irradiation (1.54060 Å). Additional peaks may typically occur at 14.30, 26.0 and 29.1; all ±0.25 (°2θ), measured with a Cu—Kα irradiation (1.54060 Å). Polymorph (III) is producable e.g. by crystallizing lacosamide from methylene chloride at about room temperature.

The term "essentially in polymorphic Form (I)" means that at least 90%, preferably at least 95%, even more preferably at least 98% or even 99% of lacosamide is in polymorphic Form (I).

In one aspect, the pharmaceutical formulations described herein may be used to administer isotopic analogs of lacosamide instead of lacosamide. The term "isotopic analogs" includes all suitable isotopic variations of lacosamide wherein at least one atom of lacosamide is replaced by an atom having the same atomic number but an atomic mass different from the atomic mass usually found in nature with the most abundant isotope(s) being preferred. Examples of isotopes that can be incorporated into lacosamide include isotopes of hydrogen, carbon, nitrogen, and oxygen such as $H^2$, $H^3$, $C^{11}$, $C^{13}$, $C^{14}$, $N^{15}$, $O^{17}$, $O^{18}$, respectively, with deuterium ($H^2$) being preferred. Isotopic analogs of lacosamide, e.g. deuterated lacosamide, can be prepared for example by conventional procedures using appropriate isotopic variations of suitable reagents.

In one aspect, the pharmaceutical formulations described herein may be also used to administer radioactive variants of lacosamide. Such variants may contain $Tc^{99m}$, $In^{111}$, $Rb^{82}$, $Cs^{137}$, $I^{123}$, $Ga^{67}$, $Ir^{192}$ or $Tl^{201}$, $C^{11}$, $N^{13}$, $O^{15}$, $F^{18}$, $Rb^{82}$, $Sr^{82}$ in an amount sufficient to be used diagnostically in Single Photon Emission Computed Tomography (SPECT) or in Positron-Emission-Tomography (PET).

In one aspect, the pharmaceutical formulations described herein may be also used to administer derivatives of lacosamide. Such derivatives may be encompassed by the general formula I

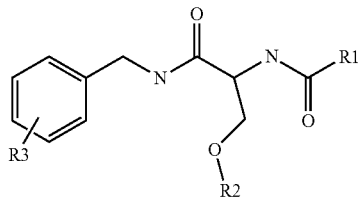

wherein
R1 is ($C_1$-$C_3$)alkyl, preferably methyl
R2 is ($C_1$-$C_6$)alkyl or ($C_2$-$C_6$)alkinyl; preferably R2 is methyl, and
R3 is hydrogen, halogen (preferably fluoro, chloro, bromo, iodo), ($C_1$-$C_3$)alkyl, ($C_1$-$C_3$)alkoxy, ($C_2$-$C_3$)alkenyl, ($C_2$-$C_3$)alkinyl, phenyl, phenyl($C_1$-$C_3$)alkyl, phenoxy or benzyloxy, wherein any of said alkyl, alkoxy, alkenyl, and alkinyl groups may be optionally substituted with one or more halogen atoms, and wherein any phenyl, phenyl($C_1$-$C_3$)alkyl, phenoxy or benzyloxy group may be optionally substituted with one or more substituents selected from halogen (preferably fluoro, chloro, bromo, or iodo), $C_1$-$C_3$ alkoxy, $C_1$-$C_3$ alkyl, and $CF_3$; preferably R3 is hydrogen, fluoro, chloro, bromo, iodo, methyl, methoxy, trifluoromethyl, optionally halogen-, methoxy- or trifluoromethyl-substituted phenoxy, or optionally halogen-, methoxy- or trifluoromethyl-substituted benzyloxy.

Such lacosamide derivatives are described, for example in EP 888289, WO 2010/148300 or US 2011/021482.

In one aspect, the formulation of the present invention may be prepared for a daily dose of lacosamide of at least 25 mg, at least 50 mg, at least 100 mg, at least 150 mg, at least 200 mg, at least 250 mg, at least 300 mg, at least 350 mg, or at least 400 mg. The formulation of the present invention may be prepared for a daily dose of lacosamide of at the most 1200 mg, at the most 1000 mg, at the most 900 mg, at the most 800 mg, at the most 700 mg, at the most 600 mg or at the most 500 mg. Particularly suited ranges for a daily dose are from about 25 mg to about 1000 mg lacosamide, preferably about 100 mg to about 900 mg, more preferably from about 200 mg to about 800 mg, even more preferably from about 250 mg to about 800 mg, from 250 mg to 700 mg, or from 300 mg to 600 mg. In one preferred aspect of the present invention, the modified release formulation disclosed herein is adapted for a 400 mg or 500 mg daily dosage. In one preferred aspect of the present invention, the modified release formulation disclosed herein is adapted for a 600 mg daily dosage. In one preferred aspect of the present invention, the modified release formulation disclosed herein is adapted for a 700 mg or 800 mg daily dosage. One aspect relates to a method of administering the lacosamide formulations of the present invention in daily doses as described hereinbefore In one aspect, the solid formulation of the present invention is prepared for once daily administration. In the solid formulation of the present invention, a single dose preferably comprises at least 25 mg, at least 50 mg, at least 100 mg, at least 150 mg, at least 200 mg, at least 250 mg, at least 300 mg, at least 350 mg, or at least 400 mg lacosamide. In the solid formulation of the present invention preferably, a single dose comprises at the most 1000 mg, at the most 900 mg, at the most 800 mg, at the most 700 mg, at the most 600 mg or at the most 500 mg of lacosamide. Particularly suited ranges for a single dose of a once daily formulations are from about 25 mg to about 1000 mg lacosamide, preferably about 100 mg to about 900 mg, more preferably from about 200 mg to about 800 mg, even more preferably from about 250 mg to about 800 mg, from 250 mg to 700 mg, or from 300 mg to 600 mg lacosamide. In one preferred aspect, the single dose forms comprise 100 mg, 200 mg, 300 mg or 400 mg lacosamide.

One aspect relates to a single solid formulation which is administered once daily and which contains the full daily dosage of lacosamide. Alternatively, at least two solid formulations may be administered at about the same time which both comprise a part of the daily dosage. For example, instead of a once a day administration of one solid formulation comprising 600 mg lacosamide, two formulations may be administered at about the same time which both contain 300 mg lacosamide each, or one formulation containing 400 mg and one containing 200 mg lacosamide may be administered at about the same time. All such potential combinations are considered part of the present disclosure. In one aspect, the invention relates to a kit of parts which consists of two single doses of lacosamide MR formulations, which provides for a total daily dose of lacosamide of between 400 mg and 900 mg, more preferably from about 400 mg to about 800 mg, even more preferably from about 450 mg to about 800 mg, from 500 mg to 700 mg, or from 500 mg to 600 mg. In one preferred aspect of the present invention, the kit of parts disclosed herein is adapted for a 500 mg or 600 mg daily dosage.

The formulation according to the present invention may provide a steady state peak to trough fluctuation (PTF) of less than 80%, wherein the PTF is (Cmax,ss-Cmin,ss)/AUC, tau,ss/tau, with Cmax,ss being the maximal plasma concentration of lacosamide at steady state, and Cmin,ss being the minimal plasma concentration of lacosamide at steady state after oral administration, and AUC,tau,ss being the area under the curve for the dosing interval tau in the steady state, and the dosing interval tau being 24 h. In particular, the PTF is preferably less than about 70%, or less than about 60%, or less than about 55%.

In one particular aspect, the solid controlled release formulation provides a release of
  (a) an amount of about 8.5 wt-% to about 41 wt-% of lacosamide relative to the total lacosamide content of the formulation within 1 h,
  (b) an amount of about 15 wt-% to about 64 wt-% of lacosamide relative to the total lacosamide content of the formulation within 2 h, and/or
  (c) an amount of about 28 wt-% to about 88 wt-% of lacosamide relative to the total lacosamide content of the formulation within 4 h,
when the in-vitro release of lacosamide is preferably measured according to USP (edition 24) method <711>, dissolution apparatus 2, in 900 mL of 0.1N HCl at 75 rpm.

In one preferred aspect, the formulation shows a release of
  (a) an amount of about 9.5 wt-% to about 26 wt-% of lacosamide relative to the total lacosamide content of the formulation within 1 h,
  (b) an amount of about 18 wt-% to about 45 wt-% of lacosamide relative to the total lacosamide content of the formulation within 2 h, and/or
  (c) an amount of about 33 wt-% to about 70 wt-% of lacosamide relative to the total lacosamide content of the formulation within 4 h,
when the in-vitro release of lacosamide is preferably measured according to USP (edition 24) method <711>, dissolution apparatus 2, in 900 mL of 0.1N HCl at 75 rpm.

In one preferred aspect, the composition comprising lacosamide and an agent for retarding the release of the lacosamide shows a release of
  (a) an amount of about 15 wt-% to about 45 wt-% of lacosamide relative to the total lacosamide content of the formulation within 1 h,
  (b) an amount of about 25 wt-% to about 60 wt-% of lacosamide relative to the total lacosamide content of the formulation within 2 h, and/or
  (c) an amount of about 40 wt-% to about 75 wt-% of lacosamide relative to the total lacosamide content of the formulation within 4 h,
when the in-vitro release of lacosamide is preferably measured according to USP (edition 24) method <711>, dissolution apparatus 2, in 900 mL of 0.1N HCl at 75 rpm. Such a formulation provides an in vivo peak-to trough formulation after once a day administration of about 32 to 67% compared to 45 to 50% of the lacosamide immediate release formulation.

In one particular preferred aspect, the formulation shows a release of
  (a) an amount of about 19 wt-% to about 40 wt-% of lacosamide relative to the total lacosamide content of the formulation within 1 h,
  (b) an amount of about 28 wt-% to about 52 wt-% of lacosamide relative to the total lacosamide content of the formulation within 2 h, and/or
  (c) an amount of about 45 wt-% to about 68 wt-% of lacosamide relative to the total lacosamide content of the formulation within 4 h,
when the in-vitro release of lacosamide is preferably measured according to USP (edition 24) method <711>, dissolution apparatus 2, in 900 mL of 0.1N HCl at 75 rpm. Such a formulation provides an in vivo peak-to trough formulation after once a day administration of only about 32% to 54% compared to 45% to 50% of the lacosamide immediate release formulation.

In one preferred aspect, the formulation shows an in-vitro release of
  (a) an amount of about 18 wt-% to about 60 wt-% of lacosamide relative to the total lacosamide content of the formulation within 2 h,
  (b) an amount of about 33 wt-% to about 75 wt-% of lacosamide relative to the total lacosamide content of the formulation within 4 h, and/or
  (c) an amount of about 55% to about 91% of lacosamide relative to the total lacosamide content of the formulation within 8 h,
when the in-vitro release of lacosamide is preferably measured according to USP (edition 24) method <711>, dissolution apparatus 2, in 900 mL of 0.1N HCl at 75 rpm.

In one aspect, the solid controlled release formulation shows at least one, at least two, at least three, at least four of the five, or even all of the five criteria (a) to (e) as follows:
  (a) within 1 h no more than about 50 wt %, preferably no more than about 45 wt %, more preferably no more than about 40 wt %, or no more than about 38 wt % of lacosamide relative to the total lacosamide content of the formulation are released,
  (b) within 2 h no more than about 72 wt %, preferably no more than about 64 wt %, more preferably no more than about 60 wt %, no more than about 52 wt % of lacosamide relative to the total lacosamide content of the formulation are released,
  (c) within 4 hours no more than about 95 wt %, preferably no more than about 88 wt %, more preferably no more than about 75 wt %, or no more than about 68 wt % of lacosamide relative to the total lacosamide content of the formulation are released,
  (d) within 8 hours preferably no more than about 98 wt %, preferably no more than about 93 wt %, more preferably no more than about 90 wt %, or no more than about 85 wt % of lacosamide relative to the total lacosamide content of the formulation are released,
  (e) within 10 hours preferably no more than about 99 wt %, preferably no more than about 95 wt %, more preferably no more than about 93 wt %, or no more than about 90 wt % of lacosamide relative to the total lacosamide content of the formulation are released,
when the in-vitro release of lacosamide is preferably measured according to USP (edition 24) method <711>, dissolution apparatus 2, in 900 mL of 0.1N HCl at 75 rpm.

In one aspect, the solid controlled release formulation shows at least one, at least two, at least three, at least four of the six, preferably five of the six, or even all of the six criteria (a) to (f) as follows:
  (a) within 1 h no more than about 50 wt %, preferably no more than about 41 wt %, more preferably no more than about 26 wt %, or no more than about 20 wt % of lacosamide relative to the total lacosamide content of the formulation are released,
  (b) within 2 h no more than about 72 wt %, preferably no more than about 64 wt %, more preferably no more than about 45 wt %, no more than about 33 wt % of lacosamide relative to the total lacosamide content of the formulation are released,
  (c) within 4 hours no more than about 95 wt %, preferably no more than about 88 wt %, more preferably no more than about 70 wt %, or no more than about 55 wt % of lacosamide relative to the total lacosamide content of the formulation are released,
(d) within 6 hours no more than about 97 wt %, preferably no more than about 95 wt %, more preferably no more than about 83 wt %, or no more than about 70 wt % of lacosamide relative to the total lacosamide content of the formulation are released,
(e) within 8 hours preferably no more than about 98 wt %, preferably no more than about 91 wt %, more preferably no more than about 85 wt %, or no more than about 80 wt % of lacosamide relative to the total lacosamide content of the formulation are released,
(f) within 10 hours preferably no more than about 99 wt %, preferably no more than about 95 wt %, more preferably no more than about 93 wt %, or no more than about 87 wt % of lacosamide relative to the total lacosamide content of the formulation are released,
when the in-vitro release of lacosamide is preferably measured according to USP (edition 24) method <711>, dissolution apparatus 2, in 900 mL of 0.1N HCl at 75 rpm.

In one aspect, the solid controlled release formulation shows at least four of the seven, preferably five of the seven, more preferably six of the seven or even all of the seven criteria (a) to (g) as follows:
(a) within 1 h at least about 8.5 wt %, preferably at least about 9 wt %, more preferably at least about 9.5 wt %, even more preferably at least about 11 wt %, but no more than about 50 wt %, preferably no more than about 41 wt %, more preferably no more than about 26 wt %, or no more than about 20 wt % of lacosamide relative to the total lacosamide content of the formulation are released,
(b) within 2 h at least about 15 wt %, preferably at least about 17 wt %, more preferably at least about 18 wt %, even more preferably at least about 21 wt %, but no more than about 72 wt %, preferably no more than about 64 wt %, more preferably no more than about 45 wt %, no more than about 33 wt % of lacosamide relative to the total lacosamide content of the formulation are released,
(c) within 4 hours at least about 28 wt %, preferably at least about 30 wt %, and more preferably at least about 33 wt %, even more preferably at least about 38 wt %, but no more than about 95 wt %, preferably no more than about 88 wt %, more preferably no more than about 70 wt %, or no more than about 55 wt % of lacosamide relative to the total lacosamide content of the formulation are released,
(d) within 6 hours at least about 38 wt %, preferably at least about 43 wt %, more preferably at least about 45 wt %, even more preferably at least about 52 wt %, but preferably no more than about 97 wt %, preferably no more than about 95 wt %, more preferably no more than about 83 wt %, or no more than about 70 wt % of lacosamide relative to the total lacosamide content of the formulation are released,
(e) within 8 hours at least about 47 wt %, preferably at least about 50 wt %, more preferably at least about 55 wt %, even more preferably at least about 64 wt %, but preferably no more than about 98 wt %, preferably no more than about 91 wt %, more preferably no more than about 85 wt %, or no more than about 80 wt % of lacosamide relative to the total lacosamide content of the formulation are released,
(f) within 10 hours at least about 53 wt %, preferably at least about 58 wt %, more preferably at least about 64 wt %, even more preferably at least about 72 wt %, but preferably no more than about 99 wt %, preferably no more than about 95 wt %, more preferably no more than about 93 wt %, or no more than about 87 wt % of lacosamide relative to the total lacosamide content of the formulation are released,
(g) within 18 hours at least about 80 wt %, preferably at least about 83 wt %, more preferably at least about 90 wt %, even more preferably at least about 95 wt % of lacosamide relative to the total lacosamide content of the formulation are released,
when the in-vitro release of lacosamide is preferably measured according to USP (edition 24) method <711>, dissolution apparatus 2, in 900 mL of 0.1N HCl at 75 rpm.

In one aspect, the solid controlled release formulation shows at least two of the seven, preferably three, four, five of the seven, more preferably six of the seven or even all of the seven criteria (a) to (g) as follows:
(a) within 1 h no more than about 75 wt %, preferably no more than about 55 wt %, more preferably no more than about 50 wt %, or no more than about 45 wt %, or no more than about 41 wt % of lacosamide, and preferably at least about 8.5 wt %, more preferably at least about 15 wt %, more preferably at least about 19 wt %, even more preferably at least about 25 wt % or 28 wt %, relative to the total lacosamide content of the formulation are released,
(b) within 2 h no more than about 80 wt %, more preferably no more than about 72 wt %, or no more than about 64 wt %, even more preferably no more than about 60 wt %, or no more than about 52 wt %, and preferably at least about 15 wt %, more preferably at least about 18 wt % or at least about 25 wt %, even more preferably at least about 28 wt %, or more than about 31 wt %, or even more than about 44 wt % of lacosamide relative to the total lacosamide content of the formulation are released,
(c) within 4 hours no more than about 99 wt %, preferably no more than about 95 wt %, more preferably no more than about 88 wt %, or no more than about 75 wt % or 70%, and preferably at least about 28 wt %, preferably at least about 30 wt % or 33 wt %, and more preferably at least about 40 wt %, even more preferably at least about 45 wt %, or more than 55 wt % of lacosamide relative to the total lacosamide content of the formulation are released,
(d) within 6 hours at least about 45 wt %, more preferably at least about 50 wt %, or more than about 58 wt %, even more preferably at least about 65 wt %, but preferably no more than about 99 wt %, more preferably no more than about 95 wt %, more preferably no more than about 90 wt % or no more than about 83 wt % of lacosamide relative to the total lacosamide content of the formulation are released,
(e) within 8 hours at least about 55 wt %, preferably at least about 64 wt %, more preferably at least about 69 wt %, even more preferably at least about 75 wt %, but preferably no more than about 99 wt %, preferably no more than about 98 wt %, more preferably no more than about 91 wt % of lacosamide relative to the total lacosamide content of the formulation are released,
(f) within 10 hours at least about 64 wt %, preferably at least about 72 wt %, more preferably at least about 78 wt %, even more preferably at least about 85 wt %, but preferably no more than about 99 wt % of lacosamide relative to the total lacosamide content of the formulation are released, (g) within 18 hours at least about 80 wt %, preferably at least about 83 wt %, more preferably at least about 90 wt %, even more preferably at least about 95 wt % of lacosamide relative to the total lacosamide content of the formulation are released, when the in-vitro release of lacosamide is preferably measured according to USP (edition 24) method <711>, dissolution apparatus 2, in 900 mL of 0.1N HCl at 75 rpm.

In just another preferred aspect, the formulation shows a release of (a) an amount of about 8.5 wt % to about 41 wt % of lacosamide relative to the total lacosamide content of the formulation within 1 h, (b) an amount of about 17 wt % to about 64 wt-% of lacosamide relative to the total lacosamide content of the formulation within 2 h, and/or (c) an amount of about 30 wt-% to about 88 wt-% of lacosamide relative to the total lacosamide content of the formulation within 4 h, when the in-vitro release of lacosamide is preferably measured according to USP (edition 24) method <711>, dissolution apparatus 2, in 900 mL of 0.1N HCl at 50 rpm.

In just another preferred aspect, the formulation shows a release of (a) an amount of about 9.5 wt % to about 35 wt % of lacosamide relative to the total lacosamide content of the formulation within 1 h, (b) an amount of about 18 wt % to about 45 wt-% of lacosamide relative to the total lacosamide content of the formulation within 2 h, and/or (c) an amount of about 33 wt-% to about 70 wt-% of lacosamide relative to the total lacosamide content of the formulation within 4 h, when the in-vitro release of lacosamide is preferably measured according to USP (edition 24) method <711>, dissolution apparatus 2, in 900 mL of 0.1N HCl at 50 rpm.

In just another preferred aspect, the formulation shows a release of (a) an amount of about 22 wt % to about 45 wt-% of lacosamide relative to the total lacosamide content of the formulation within 2 h, (b) an amount of about 38 wt-% to about 65 wt-% of lacosamide relative to the total lacosamide content of the formulation within 4 h, and/or (c) an amount of about 55 wt-% to about 85 wt-% of lacosamide relative to the total lacosamide content of the formulation within 8 h, when the in-vitro release of lacosamide is preferably measured according to USP (edition 24) method <711>, dissolution apparatus 2, in 900 mL of 0.1N HCl at 50 rpm.

In one aspect, the solid controlled release formulation shows at least two of the seven, preferably three, four, five of the seven, more preferably six of the seven or even all of the seven criteria (a) to (g) as follows:

(a) within 1 h no more than about 65 wt %, preferably no more than about 50 wt %, more preferably no more than about 41 wt % or 35 wt %, or 28 wt % of lacosamide relative to the total lacosamide content of the formulation are released, (b) within 2 h no more than about 72 wt %, more preferably no more than about 64 wt %, even more preferably no more than about 52 wt %, or no more than about 45 wt %, or no more than about 40 wt % or 33 wt % of lacosamide relative to the total lacosamide content of the formulation are released, (c) within 4 hours no more than about 87 wt %, more preferably no more than about 80 wt %, or no more than about 70 wt %, 65 wt %, 60 wt %, or even no more than about 55 wt % of lacosamide relative to the total lacosamide content of the formulation are released, (d) within 6 hours at least about 35 wt %, more preferably at least about 40 wt %, but no more than about 95 wt %, even more preferably no more than about 85 wt %, and particularly preferably no more than about 75 wt % of lacosamide relative to the total lacosamide content of the formulation are released, (e) within 8 hours at least about 45 wt %, preferably at least about 50 wt % but preferably no more than about 98 wt %, preferably no more than about 91 wt %, more preferably no more than about 85 wt % of lacosamide relative to the total lacosamide content of the formulation are released, (f) within 12 hours at least about 60 wt %, preferably at least about 65 or about 70 wt %, more preferably at least about 75 wt %, or even more than about 80 wt, of lacosamide relative to the total lacosamide content of the formulation are released, (g) within 18 hours at least about 80 wt %, preferably at least about 85 wt %, more preferably at least about 90 wt % lacosamide relative to the total lacosamide content of the formulation are released, when the in-vitro release of lacosamide is preferably measured according to USP (edition 24) method <711>, dissolution apparatus 2, in 900 mL of 0.1N HCl at 50 rpm.

In one aspect, the solid controlled release formulation shows at least two of the seven, preferably three, four, five of the seven, more preferably six of the seven or even all of the seven criteria (a) to (g) as follows:

(a) within 1 h at least about 8.5 wt %, preferably at least about 9.5 wt %, more preferably at least about 13 wt %, even more preferably at least about 15 wt %, but no more than about 65 wt %, preferably no more than about 50 wt %, more preferably no more than about 41 wt % or 35 wt %, or even no more than about 28 wt % of lacosamide relative to the total lacosamide content of the formulation are released, (b) within 2 h at least about 15 wt %, more preferably at least about 17 wt % or more than about 22 wt %, even more preferably at least about 24 wt %, but no more than about 72 wt %, more preferably no more than about 64 wt %, even more preferably no more than about 52 wt %, or no more than about 45 wt % or about 40 wt % of lacosamide relative to the total lacosamide content of the formulation are released, (c) within 4 hours at least about 30 wt %, preferably at least about 33 wt %, and more preferably at least about 38 wt %, but preferably no more than about 88 wt %, more preferably no more than about 80 wt %, or no more than about 70 wt %, 65 wt %, 60 wt %, or 55 wt % of lacosamide relative to the total lacosamide content of the formulation are released, (d) within 6 hours at least about 35 wt %, more preferably at least about 40 wt %, and even more preferably at least about 45 wt % or 50 wt % but no more than about 95 wt %, even more preferably no more than about 85 wt %, and particularly preferably no more than about 75 wt % of lacosamide relative to the total lacosamide content of the formulation are released, (e) within 8 hours at least about 45 wt %, preferably at least about 50 wt % or 55 wt %, more preferably at least about 60 wt %, but preferably no more than about 98 wt %, preferably no more than about 91 wt %, more preferably no more than about 85 wt % of lacosamide relative to the total lacosamide content of the formulation are released,
(f) within 12 hours at least about 60 wt %, preferably at least about 65 or about 70 wt %, more preferably at least about 75 wt %, or even more than about 80 wt, of lacosamide relative to the total lacosamide content of the formulation are released,
(g) within 18 hours at least about 80 wt %, preferably at least about 85 wt %, more preferably at least about 90 wt % lacosamide relative to the total lacosamide content of the formulation are released, when the in-vitro release of lacosamide is preferably measured according to USP (edition 24) method <711>, dissolution apparatus 2, in 900 mL of 0.1N HCl at 50 rpm.

It has been found, surprisingly, that the target dissolution profile and hence the subsequent in-vivo absorption and pharmacokinetic profile of lacosamide can be achieved using a large variety of galenic approaches. Lacosamide thus surprisingly allows for very flexible formulation concepts offering many alternative galenic solutions. It has also been found, surprisingly, that lacosamide is compatible with a large variability of excipients (such as e.g. fillers, binders, lubricants and the like), and with different environmental conditions (such as e.g. different environmental pH values), without substantially altering its properties, stability, or dissolution behaviour.

Accordingly, a variety of solid formulations for the delayed oral administration of lacosamide have been produced which meet the target dissolution and PK profile, and which all form part of the present invention.

One aspect of the present disclosure relates to a pharmaceutical formulation for the oral administration of lacosamide, comprising
(a) lacosamide as active ingredient, and
(b) at least one pharmaceutically acceptable excipient comprising at least one lacosamide release controlling agent.

One aspect of the present disclosure relates to a solid pharmaceutical composition for the oral administration of lacosamide, preferably for the twice daily oral administration of lacosamide, said solid formulation comprising
(a) lacosamide as active ingredient, and
(b) at least one pharmaceutically acceptable excipient comprising at least one lacosamide release controlling agent.

One aspect of the present disclosure relates to a solid pharmaceutical composition for the oral administration of lacosamide, preferably for the once daily oral administration of lacosamide, said solid formulation comprising
(a) about 50 to 1000 mg, preferably about 100 to 900 mg, or about 100 to 800 mg or between 200 and 800 mg of lacosamide as active ingredient, and
(b) at least one excipient being a lacosamide release controlling agent and being present in the matrix and/or in the coating of said solid composition, and
(c) preferably one or more further therapeutically acceptable excipients.

One aspect of the present disclosure relates to a solid pharmaceutical composition for the oral administration of lacosamide, preferably the once daily oral administration of lacosamide, said solid formulation
(1) comprising
(a) about 50 to 1000 mg, preferably about 100 to 900 mg, or about 100 to 800 mg or between 200 and 800 mg of lacosamide as active ingredient (preferably representing about 35 to 50 wt % of the total weight of the formulation), and
(b) at least one excipient being a lacosamide release controlling agent and being present
(b1) in the matrix of said solid composition in an amount of 5 to 50 wt %, preferably in an amount of about 5 to 30 wt % relative to the total weight of the formulation and/or
(b2) in the coating of said solid composition in an amount of 5 to about 35 wt % relative to the total weight of the formulation, and
(c) preferably one or more further therapeutically acceptable excipients, and
(2) showing the in-vitro dissolution profile as further disclosed herein and/or after once daily administration to animals, in particular to humans delivering the pharmacokinetic profile further disclosed herein.

One aspect of the present disclosure relates to a solid pharmaceutical composition for the oral administration of lacosamide, preferably the once daily oral administration of lacosamide, said solid formulation
(1) comprising
(a) about 50 to 1000 mg, preferably about 100 to 900 mg, or about 100 to 800 mg or between 200 and 800 mg of lacosamide (preferably representing about 35 to 50 wt % of the total weight of the formulation) as active ingredient, and
(b) at least one excipient being a lacosamide release controlling agent and being present
(b1) in the matrix of said solid composition in an amount of 5 to 50 wt %, preferably in an amount of about 5 to 30 wt % relative to the total weight of the formulation and/or
(b2) in the coating of said solid composition in an amount of 5 to about 35 wt % relative to the total weight of the formulation, and
(c) preferably one or more further therapeutically acceptable excipients, and
(2) delivering
(2.1) the in-vitro dissolution profile as further disclosed herein and/or
(2.2) after once daily administration to animals, in particular to humans a pharmacokinetic profile comprising one or more of the following features:
(a) a Cmax,ss,norm of 0.016 to 0.023, or of 0.018 to 0.023, preferably of 0.016 to 0.0215, or more preferably of 0.018 to 0.0215 µg lacosamide/ml plasma/mg lacosamide administered per dose in patients with an average distribution volume of 50 L, and/or
(b) a time point Tmax, ss for reaching the maximum plasma concentration of lacosamide after drug administration in steady state of between 4 and 10 hours, preferably between about 5 and 9 hours, more preferably between about 6.5 and 9 hours, or between about 6.8 and 8.6 hours, and/or
(c) a dose-normalized AUC in the steady state (AUC, ss, norm) of between about 0.34 to about 0.42 µg/ml/mg, preferably of about 0.400 µg/ml/mg lacosamide per dose in patients with an average distribution volume of 50 L, and/or
(d) a peak-trough fluctuation (PTF) is below 82%, preferably below 70%, more preferably below 55%, even more preferably below 45%, and/or
(e) a dose normalized minimum steady state plasma levels Cmin,ss,norm of between 0.0095 and 0.015, and preferably between 0.01 and 0.014 µg lacosamide/ml plasma/mg lacosamide per dosage unit in patients with an average distribution volume of 50 liters, and/or (f) a ka value of absorption of between about 0.1/h to about 0.5/h, preferably of between about 0.1/h to about 0.3/h, and more preferably of between about 0.1/h to 0.2/h.

One aspect of the present disclosure relates to a solid pharmaceutical composition for the once daily oral administration of lacosamide, preferably a tablet, said solid formulation (1) comprising
(a) (about 50 to 600 mg, preferably about 100 to 400 mg, most preferably 100 mg, 200 mg, 300 mg or 400 mg (in each instance preferably representing about 35 to 60 wt % of the total weight of the formulation) as active ingredient, and
(b) at least one excipient being a lacosamide release controlling agent and being present
   (b1) in the matrix of said solid composition in an amount of 1 to 40 wt %, preferably in an amount of about 5 to 30 wt %, even more preferably in an amount of 8 to 25 wt %, and particularly preferably in an amount of 10 to 20 wt % relative to the total weight of the formulation and/or
   (b2) in the coating of said solid composition in an amount of between about 3 wt % and about 35 wt % relative to the total weight of the formulation, and
(c) preferably one or more further therapeutically acceptable excipients, which may optionally comprise one or more of the group comprising fillers/diluents, binders, and lubricants, glidants in a total amount of between about 25 and 70 wt %, preferably between about 30 and 60 wt % relative to the total weight of the formulation,
and
(2) said formulation
   (2.1) delivering the in-vitro dissolution profile as further disclosed herein, and preferably
   (2.1.1.)
      (a) an amount of about 9.5 wt % to about 35 wt % of lacosamide relative to the total lacosamide content of the formulation within 1 h,
      (b) an amount of about 18 wt % to about 45 wt-% of lacosamide relative to the total lacosamide content of the formulation within 2 h, and/or
      (c) an amount of about 33 wt-% to about 70 wt-% of lacosamide relative to the total lacosamide content of the formulation within 4 h,
when the in-vitro release of lacosamide is preferably measured according to USP (edition 24) method <711>, dissolution apparatus 2, in 900 mL of 0.1N HCl at 50 rpm, and/or
   (2.1.2)
      (a) an amount of about 15 wt-% to about 45 wt-% of lacosamide relative to the total lacosamide content of the formulation within 1 h,
      (b) an amount of about 25 wt-% to about 60 wt-% of lacosamide relative to the total lacosamide content of the formulation within 2 h, and/or
      (c) an amount of about 40 wt-% to about 75 wt-% of lacosamide relative to the total lacosamide content of the formulation within 4 h,
when the in-vitro release of lacosamide is preferably measured according to USP (edition 24) method <711>, dissolution apparatus 2, in 900 mL of 0.1N HCl at 75 rpm, and/or said formulation (2.2) after once daily administration to animals, in particular to humans provides a pharmacokinetic profile comprising one or more of the following pharmacokinetic features:
   (a) a time point Tmax, ss for reaching the maximum plasma concentration of lacosamide after drug administration in steady state of between 4 and 10 hours, preferably between about 5 and 9 hours, more preferably between about 6.5 and 9 hours, or between about 6.8 and 8.6 hours, and/or
   (b) a time point Tmax for reaching the maximum plasma concentration of lacosamide after single dose administration of between about 10 and 18 hours, or between 12 and about 15 hours, and/or
   (c) a peak-trough fluctuation (PTF) is below 60%, preferably below 50%, and more preferably below about 45%, or even below about 40% and/or
   (d) a ka value of absorption of between about 0.1/h to about 0.5/h, preferably of between about 0.1/h to about 0.3/h, and more preferably of between about 0.1/h to 0.2/h.

Such an MR formulation may deliver lacosamide to the animal body in an amount leading to one or more of the following pharmacokinetic values:
   (a) a dose normalized minimum steady state plasma levels Cmin,ss,norm of between 0.0095 and 0.015, and preferably between 0.01 and 0.014 μg lacosamide/ml plasma/mg lacosamide per dosage unit in patients with an average distribution volume of 50 liters, and/or
   (b) a Cmax,ss,norm of 0.016 to 0.023, or of 0.018 to 0.023, preferably of 0.016 to 0.0215, or more preferably of 0.018 to 0.0215 μg lacosamide/ml plasma/mg lacosamide administered per dose in patients with an average distribution volume of 50 L, and/or
   (c) a dose-normalized AUC in the steady state (AUC, ss, norm) of between about 0.34 to about 0.42 μg/ml/mg, preferably of about 0.37 to 0.4 μg/ml/mg lacosamide per dose in patients with an average distribution volume of 50 L.

One aspect of the present disclosure relates to a solid pharmaceutical composition for the once daily oral administration of lacosamide, preferably a tablet, said solid formulation (1) comprising
(a) about 100 to 400 mg, most preferably 100 mg, 200 mg, 300 mg or 400 mg (in each instance preferably representing about 35 to 50 wt % of the total weight of the formulation) as active ingredient, and
(b) at least one excipient being a lacosamide release controlling agent and being present
   (b1) in the matrix of said solid composition in an amount of about 8 to 25 wt %, and particularly preferably in an amount of about 10 to 20 wt % relative to the total weight of the formulation and/or
   (b2) in the coating of said solid composition in an amount of between about 0.5 wt % and about 20 wt % relative to the total weight of the formulation, and
(c) preferably one or more further therapeutically acceptable excipients, which may optionally comprise one or more of the group comprising fillers/diluents, binders, and lubricants, glidants in a total amount of between about 25 and 70 wt %, preferably between about 30 and 60 wt % relative to the total weight of the formulation,
and
(2) said formulation
   (2.1) delivering the in-vitro dissolution profile as further disclosed herein, and preferably (2.1.1.)
a. an amount of about 9.5 wt % to about 35 wt % of lacosamide relative to the total lacosamide content of the formulation within 1 h,
b. an amount of about 18 wt % to about 45 wt-% of lacosamide relative to the total lacosamide content of the formulation within 2 h, and/or
c. an amount of about 33 wt-% to about 70 wt-% of lacosamide relative to the total lacosamide content of the formulation within 4 h, when the in-vitro release of lacosamide is preferably measured according to USP (edition 24) method <711>, dissolution apparatus 2, in 900 mL of 0.1N HCl at 50 rpm, and/or (2.1.2)
(a) an amount of about 15 wt-% to about 45 wt-% of lacosamide relative to the total lacosamide content of the formulation within 1 h,
(b) an amount of about 25 wt-% to about 60 wt-% of lacosamide relative to the total lacosamide content of the formulation within 2 h, and/or
(c) an amount of about 40 wt-% to about 75 wt-% of lacosamide relative to the total lacosamide content of the formulation within 4 h, when the in-vitro release of lacosamide is preferably measured according to USP (edition 24) method <711>, dissolution apparatus 2, in 900 mL of 0.1N HCl at 75 rpm,
and/or said formulation (2.2) after once daily administration to animals, in particular to humans comprises a pharmacokinetic profile comprising one or more of the following pharmacokinetic features:
(a) a time point Tmax, ss for reaching the maximum plasma concentration of lacosamide after drug administration in steady state of between 4 and 10 hours, preferably between about 5 and 9 hours, more preferably between about 6.5 and 9 hours, or between about 6.8 and 8.6 hours, and/or
(b) a time point Tmax for reaching the maximum plasma concentration of lacosamide after single dose administration of 7 hours or more, 8 hours or more, and preferably between about 10 and 18 hours, or between 10 and about 15 hours, and/or
(c) a peak-trough fluctuation (PTF) is below 50%, and more preferably below about 45%, or even below about 40% and/or
(d) a ka value of absorption of between about 0.1/h to about 0.3/h, and more preferably of between about 0.1/h to 0.2/h.

In one aspect in the MR formulation as described hereinbefore, the at least one release controlling agent is present only in the matrix of the formulation, while the coating, if present, is non-functional, i.e. non-retarding.

In one aspect the formulation according to present invention is provided in the form of a solid oral dosage, preferably selected from tablets with a modified release matrix, functionally coated tablets, capsules, mini tablets, pellets and granules. In a preferred aspect, the formulation of the present invention is provided in the form of a tablet, such as a matrix tablet, said tablet being with or without functional coating, or in the form of granules, such as coated granules or functionally coated granules.

One aspect is a matrix tablet with a modified release matrix and without functional coating. One aspect is a tablet with an immediate release matrix and functional coating. One aspect is a tablet with a modified release matrix and functional coating. Another aspect is a granule with an immediate release matrix and functional coating. Yet another aspect is a granule with an modified release matrix and functional coating.

In one preferred aspect of the present invention, the solid formulation may comprise a lacosamide-containing matrix, wherein the matrix comprises at least one matrix retardation agent. In the matrix, any known matrix retardation agent may be used, which, when formulated with an active agent in a matrix, is known to be capable of delaying the release of the active agent from the matrix. In particular, a matrix retardation agent as described herein may be used.

Further specific aspects of the present invention refer to solid formulations, as defined herein in terms of its ingredients, having a lacosamide release profile covered by at least one of the release profiles, as described herein. In these specific aspects, the release profile can be an in-vitro dissolution profile which may be defined in terms of lacosamide in-vitro release by USP (edition 24) method <711>, or may be expressed as the rate constant of dissolution $K_{diss}$. The administration of the solid formulations disclosed herein to animals, in particular to human beings, may result in certain pharmacokinetic profiles defined by the rate constant of absorption $k_a$, the AUC,ss,norm, the PTF, the time point Tmax or/and Cmax,ss,norm, as described herein. Specific aspects of the present invention refer to a generic or specific solid formulation as defined herein in terms of its ingredients, combined with a specific or generic release profile and/or pharmacokinetic profiles, as disclosed herein. The formulations of these specific aspects can cover one or more examples of the present invention, each disclosing a specific formulation and the corresponding release profile and/or the corresponding pharmacokinetic profile.

Granules and pellets generally may have a mean diameter of up to 3000 μm, preferably between about 200 μm and 2000 μm ($D_{50}$).

More specifically, the granules of the present invention may have a mean diameter of from about 50 μm to about 2000 μm or about 200 μm to about 1000 μm ($D_{50}$).

In one aspect, the pellets of the present invention may have a mean diameter of from about 100 μm to about 3000 μm or from about 200 μm to about 2000 μm ($D_{50}$).

The tablets of the present invention, in particular coated tablets or matrix tablets, may have a size in the range of about 5 mm to about 30 mm, preferably from about 7 mm to about 20 mm. If the tablet has an essentially round shape, the size refers to the diameter of the tablet. If the tablet has an oblong shape, the size indicates the size of the longitudinal axis. The size may be at least about 5 mm, at least about 6 mm, at least about 7 mm, at least about 8 mm, at least about 9 mm, or at least about 10 mm. The size may be at the most about 20 mm or at the most about 30 mm.

The formulation of the present invention may comprise the at least one matrix retardation agent in the matrix in an amount of at least about 1 wt %, at least 1.5 wt %, at least about 2 wt %, at least 3 wt %, at least 4 wt %, at least 5 wt %, at least 6 wt %, at least 7 wt %, at least 8 wt %, 9 wt %, at least 10 wt %, at least 12 wt % or at least about 15 wt %, relative to the total weight of the formulation. Matrix retarding agents may be present in the matrix in an amount of usually no more than about 80 wt %, preferably in an amount less than 70 wt %, less than 60 wt %, or less than 50 wt % relative to the total weight of the formulation. In particular, the at least one matrix retardation agent may be present in the matrix in an amount of 10 wt-% to 50 wt-%, preferably 10 wt % to 30 wt %, or 15 wt % to 40 wt %, relative to the total weight of the formulation. Other suitable ranges are for example 3 wt % to 80 wt %, 5 wt % to 70 wt %, 5 wt % to 60 wt %, or 5 wt % to 30 wt %, or 8 wt % to 30 wt % of a matrix retarding agent being present in the matrix, calculated relative to the total weight of the formulation.

The matrix retardation agent may be selected from polymeric and non-polymeric matrix retardation agents. For example, the non-polymer material may have a melting point greater than 37° C., preferably a melting point ranging from 40° C. to 100° C. The non-polymer material preferably is a hydrophobic material. In one aspect, the retardation agent is preferably a polymeric material.

The matrix retardation agent may also be selected from hydrophilic matrix retardation agents, hydrophobic matrix retardation agents, and inert polymers.

In one aspect, the retardation agent is preferably a hydrophilic matrix retardation agent. Hydrophilic retardation agents have the general advantages of usually becoming completely degraded in the animal body, being well characterized excipients, and showing good technical processability also on larger scale. It has also been shown in the present disclosure that hydrophilic matrix retardation agents are surprisingly well suited to control the dissolution of lacosamide.

Accordingly, in one aspect, the retardation agent is a hydrophilic polymer material preferably selected from cellulose derivatives such as hydroxyethylcellulose, hydroxypropylcellulose (HPC), methylcellulose, and hydroxypropylmethylcellulose (HPMC), and having a viscosity of 2,000 mPa·s to 200,000 mPa·s in a 2 wt-% aqueous solution at 20° C., preferably a viscosity of 5,000 mPa·s to 150,000 mPa·s in a 2 wt-% aqueous solution at 20° C. when measured using Ubbelohde capillary viscosity, or between 10,000 mPa·s and 150,000 mPa·s, in particular between 30,000 and 150,000 mPa·s, or between 50,000 mPa·s and 150,000 mPa·s.

If a high viscosity hydrophilic polymer, in particular a cellulose derivative, e.g. HPC or HPMC, having a viscosity of at least about 30,000 mPa·s, preferably of at least about 50,000 Pa·s or at least about 100,000 mPa·s in 2% aqueous solution is being used as retarding agent, the amount of HPMC in the formulation can surprisingly be as low as about 8 wt % or less, 6 wt % or less, 5 wt % or less, 4 wt % or less, 3 wt % or less or even between 1 wt % and 2 wt % relative to the total weight of the formulation. Examples of such MR formulation comprising an unexpectedly low content of HPMC are given in Examples 16 (8.3 wt % HPMC), 38 (1.8 wt % HPMC), or 39 (about 3 wt % HPMC).

Accordingly, in those aspects of the present invention where the lacosamide MR formulations comprises as the retarding agent a hydrophilic cellulose derivative such as e.g. HPC or HPMC, having a viscosity of at least about 30,000 mPa·s, preferably of at least about 50,000 Pa·s or at least about 100,000 mPa·s in 2% aqueous solution, the amount of such hydrophilic retarding agent may be generally about 8 wt % or less, about 6 wt % or less, about 5 wt % or less, about 4 wt % or less, about 3 wt % or less, or between 1 wt % and 2 wt %, relative to the total weight of the formulation. A minimum content of 1 wt % of the hydrophilic polymer, as indicated, may be present. The hydrophilic polymer, as indicated, may be the only retardation agent present, or the formulation may comprise at least one further retardation agent. The amounts of the other components given in various instances and examples herein remain unchanged.

In addition to the medium to high-viscosity cellulose derivatives described above, it has been surprisingly found that cellulose derivatives with a medium to low viscosity are also well suited for the retardation of lacosamide. This is particularly unexpected in view of the high water solubility of lacosamide which is being classified as a class I drug substance according to the Biopharmaceutics Classification System (BCS). It has been found by the present inventors that cellulose derivatives such as e.g. HPMC with a viscosity of between about 500 and 5000 mPa·s in a 2 wt-% aqueous solution at 20° C., in particular between about 600 and 2000 mPa·s can also be used to effectively modify the release of lacosamide (see examples 40, 42-45).

Likewise, in one aspect, the retardation agent is hydroxyethylcellulose, methylcellulose or hydroxypropylcellulose (HPC) having a viscosity of between about 100 mPa·s and 5,000 mPa·s in a 2 wt-% aqueous solution at 20° C. when measured using Ubbelohde capillary viscosity. In one aspect the viscosity of HPC may be between about 200 mPa·s and 2000 mPa·s if measured in a 10 wt % aqueous solution at 20° C. In another aspect, the retardation agent may be HPC having a viscosity as low as 200 mPa·s to 1000 mPa·s, or between about 200 mPa·s and 600 mPa·s in a 10 wt % aqueous solution at 20° C.

If a low viscosity hydrophilic retardation agent is used such as e.g. a HPMC having a viscosity of between about 600 and 2000 mPa·s in a 2 wt-% or aqueous solution, or a HPC having a viscosity of between about 200 and 3000 mPa·s, or between about 200 mPa·s and 600 mPa·s in an up to 10 wt-% aqueous solution, preferably amounts of at least about 8 wt %, more preferably at least about 10 wt %, or even more preferably at least about 12 wt % of such low viscosity retarding agent relative to the total weight of the formulation can be used. Corresponding formulations are disclosed e.g. as examples 40-45.

In another aspect, the matrix retardation agent is a polyethylene glycol having a viscosity given as a 1% solution in water at 25° C. of between about 1,000 and 50,000 mPas, preferably between 1,500 and 20,000 mPas (cPs), and particularly preferable between about 1500 mPa·s and 15000 mPa·s.

In another aspect, the matrix retardation agent is starch having a viscosity given as a 2% solution in water at 25° C. of between about 20 and 200 mPa·s when measured using Ubbelohde capillary viscosity, preferably between 50 and 100 mPa·s (cP·s), and particularly preferably of about 70 mPa·s.

In another aspect, the matrix retardation agent is xanthan having a viscosity given as a 1% solution in water at 25° C. of between about 500 and 2000 mPa·s when measured using Ubbelohde capillary viscosity, preferably between 1000 and 2000 mPa·s (cP·s). If such a xanthan is being used as retarding agent, the amount of xanthan in the formulation can surprisingly be as low as about 5 wt % or less, 4 wt % or less, 3 wt % or less or even between 1 wt % and 2 wt % relative to the total weight of the formulation. Examples of such MR formulation comprising a rather low content of xanthan are given in Examples 33 (2.5 wt %) or 34 (5 wt %).

Accordingly, in those aspects of the present invention where the lacosamide MR formulations comprises a xanthan as the retarding agent, the amount of such xanthan may be about 5 wt % or less, about 4 wt % or less, about 3 wt % or less, or between 1 wt % and 2 wt %, relative to the total weight of the formulation. A minimum content of 1 wt % of the xanthan as indicated may be present. The xanthan as indicated, may be the only retardation agent present, or the formulation may comprise at least one further retardation agent. The amounts of the other components given in various instances and examples herein remain unchanged.

The hydrophilic matrix retardation agent may be selected from the group of gums, cellulose ethers, cellulose esters, and other cellulose derivatives, gelatine, polysaccharides, starch, starch derivatives, vinyl acetate and its derivatives, vinyl pyrrolidone and its derivatives, and polyethylene glycols. The hydrophilic matrix retardation agents are preferably selected from the group of poloxamers, hydroxyethylcellulose, hydroxypropylcellulose (HPC), methylcellulose, carboxymethylcellulose, hydroxypropylmethylcellulose (HPMC), polyvinyl pyrrolidone, polyvinyl alcohols, modified starch, pregelatinized starch, hydroxypropyl starch, sodium hyaluronate, alginic acid, alginate salts, carrageenan, chitosan, guar gum, pectin, and xanthan gum. In one aspect hydroxypropylmethylcelluloses, hydroxypropylcelluloses and polyethylene glycols are particularly preferred.

Suitable hydrophilic matrix retardation agents as described above are widely commercially available and well known to those of skill in the art of pharmaceutical formulations.

In one aspect, the matrix retardation agent is a hydrophobic, preferably non polymeric retardation agent having a melting point greater than about 37° C., preferably a melting point ranging from 40° C. to 100° C., or even more preferred between 60° C. and 100° C., or between 60° C. and 80° C.

Hydrophobic matrix retardation agents offer the surprising advantage that for a delayed dissolution of lacosamide lower amounts of retardation agents are required compared to hydrophilic retardation agents. Hence, solid formulations of smaller size can be produced which are easier to swallow and potentially cheaper compared to those formulations using larger amounts of retardation agents.

The hydrophobic matrix retardation agent may be a digestible long-chain substituted or unsubstituted hydrocarbon including a total of between 8 and about 100 carbon atoms, preferably comprising one to three carbon chains each comprising about 10 to 35 carbon atoms, such as fats, lipids, waxes, fatty alcohols, fatty acids, fatty alcohol ethers, and fatty acid esters. The melting point of the retardation agent is preferably above the animal's body temperature in order to avoid the too rapid erosion of the matrix after administration. Preferably the melting point is above the processing temperature used in the manufacturing of the solid lacosamide formulation to avoid the retardation agents sticking to the processing tools such as e.g. the tablet stamps. Hence, hydrophobic retardation agents with a meting point above 37° C., preferably above 40° C., more preferably above 50° C., or in particular above about 60° C. are preferred.

Hydrophobic matrix retardation agents are preferably selected from the group of C8-C30 monohydric alcohols, monoglycerides, diglycerides, triglycerides, glycerine esters, hydrogenated castor oil, glyceryl behenate, hydrogenated soybean oil, lauroyl macrogolglycerides, stearyl macrogolglycerides, glyceryl palmitostearate, cethyl palmitate, glycerol esters of fatty acids and cetyl alcohol. In one aspect triglycerides and glyceryl behenate are particularly preferred.

Suitable hydrophobic matrix retardation agents as described above are widely commercially available and well known to those of skill in the art of pharmaceutical formulations.

In one aspect, the matrix retardation agent is an inert polymer, i.e. polymers which are not or only poorly biodegradable in the animal's body. For example, the inert polymer may be selected from the group of acrylic resins, cellulose derivatives, vinyl acetate derivatives, and non-water soluble polyesters, and preferably selected from the group of polyvinyl acetate, ethylcellulose, hydroxypropylmethylcellulose acetate phthalate, hydroxypropylmethylcellulose acetate succinate, shellac, polymethacrylic acid derivatives, methacrylic acid copolymer type A, methacrylic acid copolymer type B, methacrylic acid copolymer type C, ammonio methacrylate copolymer type A, ammonio methacrylate copolymer type B, neutral ethyl methyl methacrylate copolymer and basic butylated methacrylate copolymer. In one aspect polyvinyl acetates, methacrylic acid copolymer type B and neutral methacrylic acid are preferred. It has been determined, surprisingly, that some inert polymers very efficiently delay the release of lacosamide even when used in relatively low amounts.

In one preferred aspect, the matrix retardation agent is selected from the group of hydroxypropylmethylcelluloses, polyethylene glycols, ethylcelluloses, triglycerides, glyceryl behenate, polyvinyl acetates, methacrylic acid copolymer type B and neutral methacrylic acid, preferably in a total amount of 10 wt-% to 30 wt-% relative to the total weight of the formulation.

Suitable inert polymer matrix retardation agents as described above are widely commercially available and well known to those of skill in the art of pharmaceutical formulations.

In one aspect, the formulation of the present comprises lacosamide, a matrix retardation agent, and preferably at least one excipient selected from fillers, diluents, binders, lubricants, glidants, flow modifiers and non-functional film coats.

In one aspect of the present disclosure, the solid formulation comprises
  (a) lacosamide in an amount of 20 to 95 wt-%, preferably in an amount of about 35-95 wt %, more preferably in an amount of about of 50-95 wt %, or in an amount of 70 to 95 wt %,
  (b) at least one matrix retardation agent in a total amount of 5 to 80 wt-%, preferably 5 to 50 wt %, or 5 to 30 wt %, and, optionally
  (c) one or more excipients in a total amount of up to 75 wt-%, and selected from the group of fillers, diluents, binders, lubricant, glidants, flow modifier, plasticizer, anti-adherent agents, stabilizers, antioxidants, and/or
  (d) a non-functional film coat in an amount of up to 30 wt-%,
all amounts (a) to (d) relative to the total weight of the formulation.

In one aspect of the present disclosure, the solid formulation comprises
  (a) lacosamide in an amount of 20 to 95 wt-%, preferably in an amount of about 30-90 wt %, more preferably in an amount of about of 35-85 wt %, or in an amount of 40-80 wt %,
  (b) at least one matrix retardation agent in a total amount of about 1 to 15 wt-%, preferably of about 1.5 to 10 wt %, or 3 to 8 wt %, wherein said retardation agent is preferably selected from the group of cellulose derivatives having a viscosity of at least about 30,000 mPa·s, of at least about 50,000 Pa·s or at least about 100,000 mPa·s in 2% aqueous solution, and of xanthan gums, and optionally
  (c) one or more excipients in a total amount of up to 75 wt-%, and selected from the group of fillers, diluents, binders, lubricant, glidants, flow modifier, plasticizer, anti-adherent agents, stabilizers, antioxidants, and/or
  (d) a non-functional film coat in an amount of up to 30 wt-%,
all amounts (a) to (d) relative to the total weight of the formulation.

Such formulations with a high ratio of lacosamide and a low content of retardation agent are particularly useful for high dosage forms containing at least 400 mg, at least 500 mg, at least 600 mg or even at least 800 mg lacosamide.

In one aspect, the controlled release formulation is a tablet having a size of between about 7 mm and about 30 mm, preferably between about 8 mm and 20 mm, more preferably between about 10 mm and about 20 mm, and comprising
- (a) lacosamide in an amount of 20 to 95 wt-%, preferably in an amount of about 35-95 wt %, more preferably in an amount of about of 50-95 wt %, or in an amount of 70 to 95 wt %,
- (b) at least one matrix retardation agent in a total amount of 5 to 80 wt-%, preferably 5 to 50 wt %, or 5 to 30 wt % and, optionally
- (c) one or more excipients in a total amount of up to 75 wt-%, and selected from the group of fillers, diluents, binders, lubricants, glidants, flow modifiers, plasticizers, anti-adherent agents, stabilizers, antioxidants, and/or
- (d) a non-functional film coat in an amount of up to 30 wt-%, all amounts (a) to (d) relative to the total weight of the formulation.

In one aspect, the controlled release formulation is a tablet having a size of between about 5 mm and about 10 mm, preferably between about 5 mm and about 8 mm, comprising
- (a) lacosamide in an amount of 20 to 95 wt-%, preferably in an amount of about 35-95 wt %, more preferably in an amount of about 50-95 wt %, or in an amount of 70 to 95 wt %,
- (b) at least one matrix retardation agent in a total amount of at least about 5 wt-%, preferably of at least 15 wt % such as between 15 and 60%, or between 20 to 50% and, optionally
- (c) one or more excipients in a total amount of up to 75 wt-%, and selected from the group of fillers, diluents, binders, lubricants, glidants, flow modifiers, plasticizers, anti-adherent agents, stabilizers, antioxidants, and/or
- (d) a non-functional film coat in an amount of up to 30 wt-%.

all amounts (a) to (d) relative to the total weight of the formulation.

Another aspect relates to an oral controlled release formulation which comprises lacosamide in an amount of 70 to 95 wt-%, a matrix retardation agent in an amount of 5 to 30 w, a filler and/or diluent in an amount of 0 to 25 w, a binder in an amount of 0 to 15 w, a lubricant, glidant and/or flow modifier in an amount of 0 to 10 wt-%, and a non-functional film coat in an amount of 0 to 10 w, all amounts relative to the total weight of the formulation.

It has been found surprisingly that granulation, preferably wet granulation, with a retardation agent and lacosamide allows for high drug loading in the range of more than 50 wt %, or even between 70 wt % to 95 wt % lacosamide. This has the advantage of producing small, easy to swallow tablets with low amount of polymers, and accordingly lower cost of goods. Preferred excipients for use in these formulations are ethylcellulose, polyvinylacetate, and methacrylate copolymer.

Fillers and/or diluents may be selected from the group of dibasic calcium phosphate derivatives, magnesium carbonates, magnesium aluminium silicate, starch, modified starch, cellulose, microcrystalline cellulose, silicified microcrystalline cellulose, chitosan, lactose, sugars, sodium chloride, magnesium aluminometasilicate, fats, waxes, fatty alcohols or fatty acid esters, mineral oils, vegetable oils, and unsubstituted or substituted carbons.

Binders may be selected from the group of microcrystalline cellulose, silicified microcrystalline cellulose, lactose, dibasic calcium phosphate derivatives, magnesium carbonates, magnesium aluminium silicate, sodium bicarbonate, polyethylene glycol, polyvinyl pyrrolidone, copovidone, polyvinyl acetate, polyvinyl alcohol, poloxamers, ethylcellulose, hydroxyethylcellulose, hydroxypropylmethylcellulose acetate phthalate, hydroxypropylcellulose, low substituted hydroxypropylcellulose, methylcellulose, hydroxypropylmethylcellulose, hydroxypropylmethylcellulose acetate succinate, shellac, starch, modified starch, pregelatinized starch, hydroxypropyl starch, sodium carboxymethylated starch acrylic resins, materials derived from protein, methacrylic acid copolymer type A, methacrylic acid copolymer type B, methacrylic acid copolymer type C, ammonio methacrylate copolymer type A, ammonio methacrylate copolymer type B, basic butylated methacrylate copolymer, sodium hyaluronate, dextrate, dextrin, maltodextrin, alginic acid, alginate salts (e.g. sodium, potassium, calcium), carrageenan, chitosan, guar gum, pectin, xanthan gum, cethyl palmitate, glyceryl behenate, glyceryl monostearate, glyceryl palmitostearate, monoglycerides, diglycerides, triglycerides, glycerine esters, fatty alcohols, and fatty acid esters.

In the present invention, a filler being a hydrophilic polymer can typically have a viscosity below 100 mPa·s (cP·s), and in particular below 50 mPa·s, below 30 mPa·s, or below 10 mPa·s (cP·s) when measured using Ubbelohde capillary viscosity.

In the present invention, a binder being a hydrophilic polymer can typically have a viscosity below 100 mPa·s (cP·s), and in particular below 50 mPa·s, below 30 mPa·s, or below 10 mPa·s (cP·s) when measured using Ubbelohde capillary viscosity.

Lubricants, glidants or flow modifiers can be selected from the group of magnesium stearate, calcium stearate, stearic acid, talc, silicium dioxide, methylated silicium dioxide, and polyethylene glycol.

Plasticizers can be selected from the group of triethyl citrate, triacetin, glycerol, polyethylene glycol, lecithin, dibutyl phthalate, dibutyl sebacate, and diethyl phthalate.

Anti-adherent agents may be selected from the group of talcum, glyceryl monostearate, magnesium stearate, and stearic acid.

Other common excipients such as e.g. antioxidants, stabilizers, flavouring agents, colours etc. may be optionally present in the solid formulation.

Suitable non functional film coats may be preferably based on HPMC, HPC and polyvinylalcohol.

In one aspect, the weight/weight ratio between lacosamide and the matrix retardation agent may be between about 1:2 and 1:6 and preferably between about 1:3 and 1:5.

A particular aspect of the present disclosure relates to an oral controlled release formulation which comprises
- (a) lacosamide in an amount of 70 to 95 wt-%,
- (b) a matrix retardation agent in an amount of 5 to 30 wt-%, preferably of 5 to 25 wt %, and preferably selected from ethylcellulose, polyvinylacetate, and methacrylate copolymer.
- (c) a filler and/or diluent in an amount of 0 to 25 wt-%,
- (d) a binder in an amount of 0 to 15 wt,
- (e) a lubricant, glidant and/or flow modifier in an amount of 0 to 25%, preferably 0-10%, and/or
- (f) a non-functional film coat preferably in an amount of 0 to 10 wt-%, (g) all amounts relative to the total weight of the formulation.

It is to be understood that specific compounds which can be employed in the formulations described herein can be suitable as a binder and filler, wherein, in this context, the term "filler" includes diluents as described herein. For example, microcrystalline cellulose can serve as a binder, as a filler, or for both. If a specific formulation contains a compound suitable as a binder and as a filler, the amount of this compound (e.g. given in wt %) in the specific formulation may be allocated to one of the amounts of binder and filler present in a formulation as disclosed herein (in particular a generic formulation as disclosed herein), or may be allocated to both present in the formulation. For example, if a composition described in this application comprises 0 to 25 wt % of a filler/diluent and 0 to 15 wt % binder, and if certain excipients may count for both, binders and fillers, the amount of binders and fillers/diluents may be added up to a total binder plus filler/diluent content of up to 40 wt %

Another aspect of the present invention relates to an oral controlled release formulation, preferably a tablet, comprising (a) lacosamide in an amount of 1 to 80 wt-%, preferably in an amount of 20 to 75 wt %, more preferably 30 to 60 wt-%, or even more preferred about 35 to 60 wt %,
(b) a matrix retardation agent in an amount of 5 to 80 wt-%, preferably 5 to 50 wt %, or 5 to 30 wt %,
(c) filler and/or diluents in an amount of 0 to 80 wt-%, preferably 20-55 wt %,
(d) binder in an amount of 0 to 80 wt-%, preferably 10 to 50 wt %,
(e) lubricant, glidant and/or flow modifier in an amount of 0 to 80 wt-%, preferably 0 to 20 wt %, and
(f) a non-functional film coat in an amount of 0 to 30 wt-%, preferably 0 to 5 wt %, all amounts relative to the total weight of the formulation.

In particular, the formulation comprises lacosamide, a matrix retardation agent, and preferably at least one excipient selected from fillers, diluents, binders, lubricants, glidants, flow modifiers and non-functional film coats.

Another aspect of the present invention relates to an oral controlled release formulation, preferably a tablet, comprising (a) lacosamide in an amount of 30 to 60 wt %, preferably 30 to 50 wt %, or even more preferred about 35 to 50 wt %
(b) a matrix retardation agent in an amount of about 5 to 25 wt-%, preferably about 8 to about 20 wt %,
(c) filler and/or diluent in an amount of about 15 to about 30 wt %,
(d) binder in an amount of about 15 to 40 wt %, preferably about 20 to 30 wt %,
(e) lubricant, glidant and/or flow modifier in an amount of 0 to about 10 wt-%, preferably up to about 5 wt %, and
(f) a non-functional film coat in an amount of 0 to 5 wt %, all amounts relative to the total weight of the formulation.

Another preferred aspect of the present invention relates to an oral controlled release formulation, preferably a tablet, comprising (a) lacosamide in an amount of 30 to 50 wt %, or 35 to 50 wt %;
(b) a matrix retardation agent in an amount of 5 to 25 wt-%, preferably 8 to 20 wt %, more preferably about 10 to about 20 wt-%, wherein the retardation agent is preferably selected from the group of hydroxyethylcellulose, hydroxypropylcellulose (HPC), methylcellulose, and hydroxypropylmethylcellulose (HPMC), and mixtures thereof, and all having a viscosity of between about 600 mPa·s and 150,000 mPa·s, preferably between 5,000 mPa·s to 150,000 mPa·s in a 2 wt-% aqueous solution at 20° C. when measured using Ubbelohde capillary viscosity,
(c) binder, filler and/or diluent in a total amount of 20-70, preferably 30-60 wt %, wherein the filler and/or diluent is preferably selected from microcrystalline cellulose and silicified microcrystalline cellulose, and wherein the binder may be selected from microcrystalline cellulose, silicified microcrystalline cellulose, hydroxypropylcellulose, low substituted hydroxypropylcellulose, ethylcellulose, hydroxyethylcellulose, hydroxypropylmethylcellulose, methylcellulose, and mixtures thereof, all such binders being preferably either not soluble in water, or having a viscosity of less then about 2,000 mPas, preferably less than about 100 mPa·s in a 2 wt-% aqueous solution at 20° C. when measured using Ubbelohde capillary viscosity,
(d) lubricant, glidant and/or flow modifier in an amount of 0 to 5 wt-%, and
(e) a non-functional film coat in an amount of 0 to 5 wt %, all amounts relative to the total weight of the formulation.

One aspect of the present disclosure relates to a solid pharmaceutical composition for the once daily oral administration of lacosamide, preferably a tablet, said solid formulation (1) comprising
(a) about 50 to 600 mg, preferably 100 to 400 mg, most preferably 100 mg, 200 mg, 300 mg or 400 mg (in each instance preferably representing about 35 to 50 wt % of the total weight of the formulation) as active ingredient, and
(b) at least one excipient being a lacosamide release controlling agent and being present in the matrix of said solid composition in an amount of about 1 to 30 wt %, preferably 5 to 30 wt %, more preferably 8 to 25 wt %, and particularly preferably in an amount of about 10 to 20 wt % relative to the total weight of the formulation and/or
(c) preferably one or more further therapeutically acceptable excipients, which may optionally comprise one or more of the group comprising fillers/diluents, binders, and lubricants, glidants in a total amount of between about 25 and 70 wt %, preferably between about 30 and 60 wt % relative to the total weight of the formulation, wherein optionally
(c1) the filler and/or diluent may be present in an amount of 15-30 wt %, wherein the filler and/or diluent may be selected from microcrystalline cellulose and silicified microcrystalline cellulose,
(c2) the binder may be present in an amount of 15 to 40 wt %, preferably about 18 to 30 wt %, wherein the binder may be selected from microcrystalline cellulose, silicified microcrystalline cellulose, hydroxypropylcellulose, low substituted hydroxypropylcellulose, ethylcellulose, hydroxyethylcellulose, hydroxypropylmethylcellulose, methylcellulose, and mixtures thereof, all such binders being preferably either not soluble in water, or having a viscosity of less then about 2,000 mPas, preferably less than about 100 mPas in a 2 wt-% aqueous solution at 20° C. when measured using Ubbelohde capillary viscosity, and
(c3) a lubricant, glidant and/or flow modifier may be present in an amount of 0 to 5 wt-%, and (2) said formulation
(2.1) delivering the in-vitro dissolution profile as further disclosed herein, and preferably
(2.1.1.)
    (a) an amount of about 8.5 wt % to about 41 wt % of lacosamide relative to the total lacosamide content of the formulation within 1 h,
    (b) an amount of about 17 wt % to about 64 wt-% of lacosamide relative to the total lacosamide content of the formulation within 2 h, and/or
    (c) an amount of about 30 wt-% to about 88 wt-% of lacosamide relative to the total lacosamide content of the formulation within 4 h,
when the in-vitro release of lacosamide in is preferably measured according to USP (edition 24) method <711>, dissolution apparatus 2, in 900 mL of 0.1N HCl at 50 rpm, and/or
(2.1.2)
    (a) an amount of about 8.5 wt-% to about 50 wt-% of lacosamide relative to the total lacosamide content of the formulation within 1 h,
    (b) an amount of about 15 wt-% to about 70 wt-% of lacosamide relative to the total lacosamide content of the formulation within 2 h, and/or
    (c) an amount of about 28 wt-% to about 90 wt-% of lacosamide relative to the total lacosamide content of the formulation within 4 h,
when the in-vitro release of lacosamide is preferably measured according to USP (edition 24) method <711>, dissolution apparatus 2, in 900 mL of 0.1N HCl at 75 rpm, and/or said formulation
(2.2) after once daily administration to animals, in particular to humans comprises a pharmacokinetic profile comprising one or more of the following pharmacokinetic features:
    (a) a time point Tmax, ss for reaching the maximum plasma concentration of lacosamide after drug administration in steady state of between 4 and 10 hours, preferably between about 5 and 9 hours, more preferably between about 6.5 and 9 hours, or between about 6.8 and 8.6 hours, and/or
    (b) a time point Tmax for reaching the maximum plasma concentration of lacosamide after single dose administration of 7 hours or more, 8 hours or more, and preferably between about 10 and 18 hours, or between 10 and about 15 hours, and/or
    (c) a peak-trough fluctuation (PTF) is below 50%, and more preferably below about 45%, or even below about 40% and/or
    (d) a ka value of absorption of between about 0.1/h to about 0.3/h, and more preferably of between about 0.1/h to 0.2/h.

Another preferred aspect of the present invention relates to an oral controlled release formulation, preferably a tablet, comprising
(a) lacosamide in an amount of 30 to 50 wt %, or 35 to 50 wt %;
(b) a matrix retardation agent in an amount of 5 to 25 wt-%, preferably 8 to 20 wt %, more preferably about 8 to about 18 wt-%, wherein the retardation agent is preferably selected from the group of hydroxyethylcellulose, hydroxypropylcellulose (HPC), methylcellulose, and hydroxypropylmethylcellulose (HPMC), and mixtures thereof, and all having a viscosity of 5,000 mPas to 150,000 mPas in a 2 wt-% aqueous solution at 20° C. when measured using Ubbelohde capillary viscosity,
(c) filler and/or diluent in an amount of 15-30 wt %, wherein the filler and/or diluent is preferably selected from microcrystalline cellulose and silicified microcrystalline cellulose,
(d) binder in an amount of 15 to 40 wt %, preferably about 18 to 30 wt %, wherein the binder is preferably selected from microcrystalline cellulose, silicified microcrystalline cellulose, hydroxypropylcellulose, low substituted hydroxypropylcellulose, ethylcellulose, hydroxyethylcellulose, hydroxypropylmethylcellulose, methylcellulose, and mixtures thereof, all such binders being preferably either not soluble in water, or having a viscosity of less then about 2,000 mPas in a 2 wt-% aqueous solution at 20° C. when measured using Ubbelohde capillary viscosity,
(e) lubricant, glidant and/or flow modifier in an amount of 0 to 5 wt-%, and
(f) a non-functional film coat in an amount of 0 to 5 wt %,
all amounts relative to the total weight of the formulation.

Another aspect of the present invention relates to an oral controlled release formulation, preferably a tablet, comprising
(a) lacosamide in an amount of about 30 to 60 wt %, or about 35 to 50 wt %;
(b) a matrix retardation agent in an amount of 8 to 40 wt-%, preferably 10 to 30 wt %, more preferably about 12 to about 25 wt-%, wherein the retardation agent is selected from the group of
    a. ethylcellulose, methylcellulose or hydroxypropylcellulose (HPC), having a viscosity of 100 mPa·s to 5,000 mPa·s in a 2 wt-% aqueous solution and/or between 200 and 600 mPas in a 10 wt % solution;
    b. hydroxypropylmethylcellulose (HPMC) having a viscosity of between about 500 and 5000 mPa·s in a 2 wt-% aqueous solution and mixtures thereof,
(c) binder, filler and/or diluent in an amount of 25-70 wt %, wherein the filler and/or diluent is preferably selected from microcrystalline cellulose and silicified microcrystalline cellulose, and the binder is preferably selected from microcrystalline cellulose, silicified microcrystalline cellulose, hydroxypropylcellulose, low substituted hydroxypropylcellulose, ethylcellulose, hydroxyethylcellulose, hydroxypropylmethylcellulose, methylcellulose, and mixtures thereof, all such fillers, diluents and binders being preferably either not soluble in water, or having a viscosity of less then about 100 mPa·s in a 2 wt-% aqueous solution,
(d) lubricant, glidant and/or flow modifier in an amount of 0 to 5 wt-%, and
(e) a non-functional film coat in an amount of 0 to 5 wt %,
all amounts relative to the total weight of the formulation.

Another preferred aspect of the present invention relates to an oral controlled release formulation, preferably a tablet, comprising
(a) lacosamide in an amount of 35 to 45 wt %,
(b) a matrix retardation agent in an amount of 8 to 20 wt %, more preferably about 8 to about 18 wt-%, wherein the retardation agent is preferably hydroxypropylmethylcellulose (HPMC) having a viscosity of 5,000 mPas to 50,000 mPas in a 2 wt-% aqueous solution at 20° C. when measured using Ubbelohde capillary viscosity, (c) filler and/or diluent in an amount of about 15 to about 30 wt %, wherein the filler and/or diluent is preferably silicified microcrystalline cellulose,
(d) binder in an amount of about 18 to 28 wt %, wherein the binder is preferably a mixture of
  (d1) 8 to 15 wt %, preferably 10-12 wt % microcrystalline cellulose or silicified microcrystalline cellulose,
  (d2) 0 to 5 wt %, preferably 0.5 to 2 wt % hydroxypropylcellulose,
  (d3) 5 to 15 wt %, preferably 8 to 12 wt % low substituted hydroxypropylcellulose,
(e) such binders being preferably either not soluble in water, or having a viscosity of less then about 2,000 mPas in a 2 wt-% aqueous solution at 20° C. when measured using Ubbelohde capillary viscosity
(f) a lubricant, glidant and/or flow modifier in an amount of 0 to 5 wt-%, preferably 0.5 to 2 wt %, wherein the lubricant may be magnesium stearate, and
(g) a non-functional film coat in an amount of 0 to 5 wt %,
all amounts relative to the total weight of the formulation.

Another preferred aspect of the present invention relates to an oral controlled release formulation, preferably a tablet, comprising
(a) lacosamide in an amount of 30 to 60%, preferably 35 to 45 wt %,
(b) a matrix retardation agent in an amount of 8 to 20 wt %, more preferably about 8 to about 18 wt-%, wherein the retardation agent is preferably hydroxypropylmethylcellulose (HPMC) having a viscosity of 5,000 mPas to 50,000 mPas in a 2 wt-% aqueous solution at 20° C. when measured using Ubbelohde capillary viscosity, such as e.g. Methocel® K15M
(c) at least one filler and/or diluent in an amount of about 10 to about 40 wt %,
(d) at least one binder in an amount of about 10 to about 40 wt %,
(e) lubricant, glidant and/or flow modifier in an amount of 0 to 10 wt-%, preferably 0.5 to 5 wt %, and
(f) a non-functional film coat in an amount of 0 to 5 wt %,
all amounts relative to the total weight of the formulation.

Another preferred aspect of the present invention relates to an oral controlled release formulation, preferably a tablet, comprising
(a) lacosamide in an amount of 20 to 60%, preferably 30 to 50 wt %, more preferably 35 to 45 wt %,
(b) a matrix retardation agent in an amount of 6 wt % to 25 wt %, more preferably about 8 wt % to about 20 wt %, even more preferably between about 8 wt % and 18 wt-%, wherein the retardation agent is preferably hydroxypropylmethylcellulose (HPMC) having a viscosity of 5,000 mPas to 50,000 mPas in a 2 wt-% aqueous solution at 20° C. when measured using Ubbelohde capillary viscosity, such as e.g. Methocel® K15M, and
(c) at least one excipient selected from
  (c1) fillers, and/or diluents, preferably in an amount of about 10 to about 40 wt %,
  (c2) binders, preferably in an amount of about 10 to about 40 wt %,
  (c3) lubricants, glidants, or flow modifiers, preferably in an amount of 0 to 10 wt-%, preferably 0.5 to 5 wt %, or 0.5 to 2 wt %, and
  (c4) a non-functional film coat, preferably in an amount of 0 to 5 wt %,
all amounts relative to the total weight of the formulation, and wherein the tablet has a size of at least about 8 mm, more preferably of at least about 10 mm. In one aspect, the tablet has an oblong shape with a longitudinal axis of about 10 to 20 mm, and a traverse axis of about 6 to 12 mm.

One aspect of the present invention relates to a method of manufacturing a solid formulation comprising a lacosamide controlled release matrix, wherein the method comprises the following steps:
(a) mixing suitable amounts of lacosamide, a matrix retardation agent, and optionally a binder, preferably in an aqueous solvent,
(b) granulating the mixture produced in step (a), preferably by wet granulation,
(c) adding the remaining matrix excipients and mixing with the granules produced in step (b),
(d) pressing the blend produced in step (c) to tablets, and
(e) optionally applying a coating to the tablets obtained in step (d).

In another aspect of the present invention is a solid controlled release formulation of lacosamide for oral administration, wherein the formulation comprises
(a) a lacosamide-containing matrix, and
(b) at least one release controlling layer surrounding said lacosamide-containing matrix, the at least one release controlling layer comprising a release controlling agent.

In this aspect, the lacosamide-containing matrix may comprise at least one excipient. In this aspect, the lacosamide-containing matrix may be any matrix as described herein. In particular, the lacosamide-containing matrix (a) may be
(i) an immediate release matrix, as described herein, or
(ii) a modified release matrix comprising at least one release controlling agent.

In the formulation of this aspect, the modified release matrix (ii) may be any modified release matrix as described herein. In particular, the modified release matrix (ii) may be provided in any solid form as described herein. The release controlling agent in (ii) may be selected from matrix retardation agents as disclosed herein.

In one aspect, the release of lacosamide is controlled by the functional layer surrounding the lacosamide containing matrix, said layer comprising at least one lacosamide release controlling agent, which is preferably a release controlling polymer.

In another aspect, the release controlling layer may solely control the lacosamide release from the solid formulation, if, for example, the lacosamide-containing matrix (a) is an immediate release matrix.

In another aspect, the release controlling layer may surround a lacosamide-containing matrix which may also include a release controlling agent. In this case, the release of lacosamide may be delayed in part by the controlled release matrix, and in part by the release controlling layer. This has the advantage that even if the outer layer is disrupted during processing, storage or handling by the patient, the matrix would still provide some delay of the lacosamide release. In addition, the delayed release layer would minimize the "burst" effect based on an immediate release of the part of lacosamide which is attached to the surface of the matrix. Hence, the twofold delay of the lacosamide release by both the matrix and the delayed release coating allows for a particularly well controlled release. This is particularly suited for multiple unit doses, wherein the single units are very small (with a size in the mm or even μm range) and have a high specific surface area that makes lacosamide retardation solely via a release matrix more difficult.

The at least one release controlling layer (b) may comprise at least one water-insoluble wax or at least one polymer capable of delaying the release of lacosamide. Any wax or polymer may be employed which, when used in a release controlling layer surrounding a core, is known to be capable of delaying the release of an active agent from the core.

For example, the release controlling layer may comprise at least one release delaying polymer which is selected from acrylic resins, cellulose derivatives, or vinyl acetate derivatives. These polymers may be water-soluble or water-insoluble. These polymers are preferably selected from polyvinyl pyrrolidone, polyvinyl acetate, ethylcellulose, hydroxypropylmethylcellulose acetate phthalate, hydroxypropylcellulose, hydroxypropylmethylcellulose acetate succinate, shellac, methacrylic acid copolymer type A, methacrylic acid copolymer type B, methacrylic acid copolymer type C, ammonio methacrylate copolymer type A, ammonio methacrylate copolymer type B, and basic butylated methacrylate copolymer Suitable release controlling polymers as described above are widely commercially available and well known to those of skill in the art of pharmaceutical formulations.

In the formulation of the present invention, the release controlling layer may be present in an amount of 1 to 60 wt-%, preferably in an amount of 5 to 45 wt %, and more preferably in an amount of 5 to 35 wt-% relative to the total weight of the formulation. In one aspect of the invention, the release controlling layer may be present in an amount between about 1 and 20 wt %, preferably between about 2 and 15 wt % relative to the total weight of the formulation.

The total content of retarding agent in the release controlling layer (functional coating) relative to the total weight of the formulation may be between about 0.2 and 20 wt %, preferably between about 0.5 and 15 wt %. Examples of MR formulations comprising a total content of retarding agent as low as between about 0.9 wt % and 3 wt % are given in Examples 53 and 54 herein. Examples of MR formulations comprising a higher total content of retarding agent in the functional coating are provided in Examples 7 to 13 herein.

In one aspect of the present disclosure, the lacosamide dissolution is primarily controlled by the erosion, disruption or swelling of the release controlling layer, which is a function of the nature of the layer. Alternatively, water-soluble pore-forming agents may be present in the release controlling layer as well. Water-soluble pore-forming agents such as hydroxypropylmethylcellulose, polyethyleneglycol, mono- or disaccharides, and inorganic salts may be embedded within the less soluble release controlling agent(s) and rapidly dissolve in aqueous environment thus opening pores through which lacosamide is released.

In the formulation of the present invention, the release controlling layer may comprise the release delaying polymer in a total amount of 5 to 35 wt-% relative to the total weight of the formulation. Preferred release delaying polymers for use in the release controlling layer are ethylcelluloses, polyvinyl acetates, methacrylic acid copolymer type B and neutral ethyl methyl methacrylate copolymer.

In addition to the one or more lacosamide release delaying polymers, the release controlling layer of the present disclosure may further comprise one or more additional excipients which may be selected from the group of co-binders, pore formers, anti-sticking agents, antifoam agents, flavouring agents, pigments, dyes, and processing aid agents, like plasticizers, emulsifiers or stabilizers as are generally known in the art.

In another aspect of the present invention is a solid controlled release formulation of lacosamide for oral administration, wherein the formulation comprises
  (a) a lacosamide-containing matrix, and
  (b) at least one release controlling layer surrounding said lacosamide-containing matrix, the at least one release controlling layer comprising a release controlling agent,
wherein the lacosamide-containing matrix (a) is either an immediate release matrix, or comprises at least one matrix retardation agent as described herein.

In one aspect of the present disclosure, the solid formulation comprises
  (a) a lacosamide-containing matrix, and
  (b) at least one release controlling layer surrounding said lacosamide-containing matrix, the at least one release controlling layer comprising a release controlling agent,
  (c) and at least one selected from
    (c1) an intermediate layer which is located between the lacosamide containing matrix (a) and the release controlling layer (b) and
    (c2) a final outer layer surrounding the release controlling matrix (b)

In this aspect, the solid formulation may comprise layer (c1) and (c2).

An immediate release layer between the lacosamide containing matrix and the release controlling outer layer may or may not contain lacosamide and may or may not contribute to the final release profile.

An outer coating surrounding the release controlling layer may contain colours and/or flavours, and/or may provide excipients useful to ensure the stability of the tablet during storage One aspect of the present disclosure relates to a solid formulation for the oral administration of lacosamide comprising
  (a) a matrix comprising
    (a1) lacosamide in an amount of 1 to 95 wt-%, preferably 30-95 wt %, more preferably 40 to 95 wt %, even more preferably 50 to 95 wt %,
    (a2) a filler and/or diluent in an amount of 0 to 80 wt-%, preferably 0-50 wt %, more preferably 0 to 30 wt %,
    (a3) a binder in an amount of 0 to 80 wt-%, preferably 0-50 wt %, more preferably 0 to 30 wt %, or 0 to 15 wt %,
    (a4) optionally a lubricant, glidant and/or flow modifier in an amount of 0 to 80 wt %, and
  (b) a controlled release layer in an amount of 1 to 60 wt-%, preferably 5 to 35 wt %, and optionally
  (c) a final outer layer or film coat surrounding the release controlling matrix (b) in an amount of 0-30 wt-%,
all amounts relative to the total weight of the formulation.

One aspect of the present disclosure relates to a solid formulation for the oral administration of lacosamide, said formulation being a granule or pellet for use in a multiple dosage unit, and each granule or pellet comprising
  (a) a matrix comprising
    (a1) lacosamide in an amount of 1 to 95 wt-%, preferably 30-95 wt %, more preferably 40 to 95 wt %, even more preferably 50 to 95 wt %,
    (a2) a filler and/or diluent in an amount of 0 to 80 wt-%, preferably 0-50 wt %, more preferably 0 to 30 wt %, (a3) a binder in an amount of 0 to 80 wt-%, preferably 0-50 wt %, more preferably 0 to 30 wt %, or 0 to 15 wt %,
(a4) optionally a lubricant, glidant and/or flow modifier in an amount of 0 to 80 wt %, and
(b) a controlled release layer in an amount of 1 to 60 wt-%, preferably 5 to 35 wt %, and optionally
(c) a final outer layer or film coat surrounding the release controlling matrix (b) in an amount of 0-30 wt-%, all amounts relative to the total weight of the formulation.

One aspect of the present invention relates to a method of manufacturing a solid formulation comprising a lacosamide release controlling layer, wherein the method comprises the following principle steps:
(a) mixing suitable amounts of lacosamide, and optionally a filler, binder and matrix retardation agent, preferably using an aqueous solvent,
(b) granulating the mixture produced in step (a), preferably by wet granulation,
(c) applying a functional-coating to the granules, particles or pellets obtained in step (b),
(d) adding and mixing the remaining excipients with the granules produced in step (c),
(e) filling the blend produced in step (d) into capsules or sachets and optionally pressing into tablets.

The solid formulation of the present invention can be produced by a method comprising one selected from dry granulation, wet granulation, melt extrusion, melt embedding and direct compression. In particular, a solid formulation having a release profile of lacosamide, as disclosed herein, can be produced by a method comprising one selected from dry granulation, wet granulation, melt extrusion, melt embedding and direct compression.

Specific aspects of the present invention relate to solid formulations as defined herein in terms of its ingredients, having a lacosamide release profile covered by at least one of the release profiles, as described herein, wherein the formulation is produced by a method comprising one selected from dry granulation, wet granulation, melt extrusion, melt embedding and direct compression. In these specific aspects, the release profile can be an in-vitro dissolution profile which may be defined in terms of lacosamide in-vitro release by USP (edition 24) method <711>. The release profile may also be defined by the rate of dissolution $k_{diss}$, or may be expressed as the rate constant of dissolution $K_{diss}$. The administration of a solid lacosamide formulation produced by a method described herein may result in certain pharmacokinetic profiles defined by the rate constant of absorption $k_a$, the AUC,ss,norm, the PTF, the time point Tmax or/and Cmax,ss,norm, as described herein. Specific aspects of the present invention refer to a generic or specific solid formulation as defined herein in terms of its ingredients, combined with a specific or generic release profile and/or a pharmacokinetic profile, as disclosed herein, wherein the formulation is produced by a method comprising one selected from dry granulation, wet granulation, melt extrusion, melt embedding and direct compression. The formulations of these specific aspects can cover one or more examples of the present invention, each disclosing the production of a specific formulation, and the release profile of and/or the pharmacokinetic profile associated with the formulation.

Further specific aspects of the present invention relate to solid formulations having a lacosamide release profile covered by at least one of the release profiles, as described herein, wherein the formulation is produced by a method comprising one selected from dry granulation, wet granulation, melt extrusion, melt embedding and direct compression. In these specific aspects, the release profile can be an in-vitro dissolution profile which may be defined in terms of lacosamide in-vitro release by USP (edition 24) method <711>. The release profile may also be defined by the rate of dissolution $k_{diss}$, or may be expressed as the rate constant of dissolution $k_{diss}$. The administration of a solid lacosamide formulation produced by a method described herein may result in certain pharmacokinetic profiles defined by the rate constant of absorption $k_a$, AUC,ss,norm, the PTF, the time point Tmax or/and Cmax,ss,norm, as described herein. Specific aspects of the present invention refer to a generic or specific solid formulation having a specific or generic release profile and/or a pharmacokinetic profile, as disclosed herein, wherein the formulation is produced by a method comprising one selected from dry granulation, wet granulation, melt extrusion, melt embedding and direct compression. The formulations of these specific aspects can cover one or more examples of the present invention, each disclosing the production of a specific formulation, and the release profile of the formulation.

A formulation of the present invention can be produced by wet granulation. An exemplary method for producing the formulation of the present invention by wet granulation can comprise the steps
(a) mixing suitable amounts of lacosamide, and optionally one or more fillers, binders and/or matrix retardation agents, preferably using an aqueous solvent,
(b) granulating the mixture produced in step (a), preferably by wet granulation,
(c) optionally applying a functional coating to the granules,
(d) optionally adding and mixing the remaining excipients with the granules produced in step (b) or (c),
(e) pressing the blend produced in step (d) into tablets, and
(f) optionally applying a functional coating to the tablets.

Examples 14-32 provide formulations produced by this method (no functional coating).

Examples 51 to 52 provide tablets produced by this method having a functional coating applied to the tablets. In one aspect of the method described hereinbefore, steps (a) and (b) comprise the mixing and granulating of lacosamide with one or more binders and/or fillers, step (d) comprises blending the granules produced in step (b) with at least one retardation agent and optionally other excipients, and steps (c) and (f) are missing.

The formulation of the present invention can be produced by dry granulation. An exemplary method for producing the formulation of the present invention by dry granulation can comprise the steps
(a) mixing suitable amounts of lacosamide and optionally and optionally a filler, binder or/and further excipient,
(b) compacting the mixture of (a)
(c) breaking down the compacted mixture of (b) to granules
(d) adding a suitable amount of at least one matrix retardation agent to the granules of (c) to form a blend, and
(e) compressing the blend of (d) to tablets.

Examples 37-47 provide formulations produced by this method.

Another exemplary method for producing the formulation of the present invention by dry granulation can comprise the steps
(a) mixing suitable amounts of lacosamide, at least one matrix retardation agent, and optionally a filler, binder or/and further excipient,
(b) compacting (including roller-compacting) the mixture of (a), (c) breaking down the compacted mixture of (b) to granules, and
(d) compressing the granules of (c) to tablets.

Examples 33 to 35 provide formulations produced by this method. If the tablets are mini-tablets, the method can comprise a further step (e): filling the mini-tablets into capsules.

The formulation of the present invention can be produced by direct compression. An exemplary method for producing the formulation of the present invention by direct compression can comprise the steps
(a) mixing suitable amounts of lacosamide, a matrix retardation agent, and optionally a filler, binder or/and further excipient,
(b) compressing the mixture of (a) to tablets.

Example 48 provides a formulation produced by this method.

The formulation of the present invention can be produced by melt embedding or/and melt extrusion. An exemplary method for producing the formulation of the present invention by melt embedding or/and melt extrusion can comprise the steps
(a) mixing suitable amounts of lacosamide, a matrix retardation agent, and optionally a further excipient,
(b) heating the blend of (a) until a dispersion of lacosamide and the matrix retardation is formed by melting of the matrix retardation agent,
(c) filling the dispersion of (b) into capsules, and
(d) cooling down the capsules of (c) to room temperature and closing the capsules.

The skilled person knows matrix retardation agents suitable for this melt extrusion/melt embedding method. Example 49 provides a formulation produced by this method.

Furthermore, formulations of the present invention being film-coated granules may be prepared by a method comprising granulation, preferably wet granulation. An exemplary method for producing the granules according to the present invention by granulation can comprise the steps
(a) mixing suitable amounts of lacosamide with a matrix retardation agent, and optionally a filler, binder and further excipient, preferably using an aqueous solvent,
(b) granulating the mixture produced in step (a), preferably by wet granulation, and
(c) applying a functional coating to the granules, particles or pellets obtained in step (b), Examples 7 to 13 provide formulations produced by this method.

It is preferred to produce the formulation of the present invention by a method comprising wet granulation.

It is also preferred to produce the formulation of the present invention by a method comprising dry granulation.

It is also preferred to produce the formulation of the present invention by a method comprising melt embedding or/and melt extrusion.

The formulations according to the present disclosure can be present as single unit dosage, in particular in the form of a tablet.

The lacosamide controlled release formulation may also be prepared in the form of multiple dosing units such as powders/particles, pellets, minitablets, or granulates which maybe then packed into sachets, capsules or digestable coatings prior to storage and/or oral administration.

Accordingly, one aspect of the present invention relates to lacosamide modified release formulations as disclosed herein comprising multiple unit dosage forms. One aspect of the present invention relates to multiple unit dosage forms comprising lacosamide, wherein a multitude of such multiple unit dosage forms provide an average lacosamide in vivo absorption and/or in-vitro dissolution profile as disclosed herein. One aspect of the present invention relates to the use of multiple unit dosage forms comprising lacosamide for the manufacturing of a lacosamide modified release formulation as disclosed herein.

Multiple unit dosage forms for the oral administration of lacosamide are not previously known but offer a variety of advantages to the patient:
flexible dosing of lacosamide because individual dosages can be prepared by weighing or counting the powders/particles, pellets, minitablets or granules that are to be administered. This is particularly important if a patient needs a defined individual dosage in order to guarantee efficacy on one hand but minimize or eliminate undesirable side effects on the other hand.
ease of administration because the powders/particles, pellets, minitablets or granules can be administered via various dosing forms. While they are typically administered via capsules, they can also be dispersed into liquids such as juice or water, which is particularly convenient for patients having difficulties or aversions to swallowing tablets.
powders/particles, pellets, minitablets or granules allow oral administration of lacosamide via tube feeding. Hence even patients who are completely unable to swallow and could otherwise not take oral anticonvulsives could benefit from these oral lacosamide formulations.

Accordingly, one aspect of the present disclosure is a solid formulation for the oral administration of lacosamide having a diameter of below about 3 mm, and more preferably a diameter of between about 0.1 and 2.5 mm. In one preferred aspect, said formulation is in the form of a particle, pellet, mini-tablet or granule and releases lacosamide in a controlled release fashion as further described in this application.

The release of lacosamide from said controlled release formulation may be pH dependent or pH independent. For example, the formulation may be designed in a way such that the lacosamide release will be triggered by an acidic or basic environment such that lacosamide may be preferably released in a certain part of the gastrointestinal tract. This can be achieved by using appropriate excipients which erode or disintegrate pH-dependently. However, in a preferred aspect of the present disclosure, the release of lacosamide from the controlled release formulation is pH independent, i.e. lacosamide will be released and absorbed during the entire passage of the gastrointestinal tract.

Medical Uses and Methods of Treatment

The formulation according to the present invention may be used in the prevention, alleviation, and/or treatment of a disease of the central nervous system, and respective methods.

The formulation according to the present invention may be used in the prevention, alleviation, and/or treatment of a disease selected from neurological diseases, psychiatric diseases, or/and inflammatory diseases, and respective methods.

The formulation according to the present invention may be used in the prevention, alleviation, and/or treatment of a neurological disease, such as epilepsy, a pain syndrome, a motoneuron disorder, a dyskinesia, or a tremor syndrome, and respective methods.

The formulation according to the present invention may be used in the prevention, alleviation, and/or treatment of a psychiatric disease, such as psychosis, bipolar disorder, anxiety diseases, depressions, obsessive-compulsive disorders, or/and schizophrenia, and respective methods.

The formulation according to the present invention may be used in the prevention, alleviation, and/or treatment of an inflammatory disease such as arthritis or an arthritic condition associated with inflammation, e.g. inflammatory osteoarthritis, and respective methods.

The formulation according to the present invention may be used in the prevention, alleviation, and/or treatment of a disease selected from epilepsy, pain syndromes, motoneuron disorders, dyskinesias, tremor syndromes, psychosis, especially schizophrenia and bipolar disorder, arthritis or an arthritic condition such as osteoarthritis, fibromyalgia and any condition or disease included therein as described herein, and combinations thereof, and respective methods.

The formulation according to the present invention may be used in the prevention, alleviation, and/or treatment of a disease selected from epilepsy, pain syndromes, motoneuron disorders, dyskinesias, tremor syndromes different from Parkinsonian tremor syndrome, arthritis or an arthritic condition such as osteoarthritis, fibromyalgia and any condition or disease included therein as described herein, and combinations thereof, and respective methods.

The formulation according to the present invention may be used in the prevention, alleviation, and/or treatment of a disease selected from epilepsy, epileptic seizures and epilepsy conditions as described herein.

The formulation according to the present invention may be used in the prevention, alleviation, and/or treatment of a disease selected from pain syndromes, and respective methods.

The formulation according to the present invention may be used in the prevention, alleviation, and/or treatment of a disease selected from motoneuron disorders, and respective methods.

The formulation according to the present invention may be used in the prevention, alleviation, and/or treatment of a disease selected from dyskinesias, and respective methods.

The formulation according to the present invention may be used in the prevention, alleviation, and/or treatment of a disease selected from tremor syndromes, such as tremor syndromes different from Parkinsonian tremor syndrome, and respective methods.

The formulation according to the present invention may be used in the prevention, alleviation, and/or treatment of psychosis, especially schizophrenia, and bipolar disorder including the depressive phase of bipolar disorder, and respective methods.

The formulation according to the present invention may be used in the prevention, alleviation, and/or treatment of a disease selected from arthritis or an arthritic condition such as fibromyalgia and osteoarthritis, and respective methods.

The formulation according to the present invention may be used in the prevention, alleviation, and/or treatment of a disease selected from epilepsy. Epilepsy conditions include heritary, idiopathic and acquired forms of epilepsy including status epilepticus. Preferred epilepsy conditions to be treated with the formulation of the present disclosure are, focal epilepsy syndromes such as partial onset seizures with and without secondary generalization, complex partial seizures with and without secondary generalization, generalized epilepsy syndromes including those associated with clonic and/or tonic seizures (including primary generalized tonic clonic seizures, PGTS), or with myoclonic or absence seizures, and respective methods.

A preferred pain syndrome to be treated with the present formulation is painful diabetic neuropathy, preferably associated with Diabetes mellitus Type I or II, more preferably Type II. Another preferred pain syndrome is pain associated with arthritis or an arthritic condition, in particular with osteoarthritis.

Treatment and Prevention of Epilepsy:

Epilepsy includes, but is not limited to, primary generalized seizures, complex partial seizures with and without secondary generalization, status epilepticus and a status epilepticus-related condition, e.g. acute repetitive seizures, seizure clusters, etc. The epilepsy condition according to the present disclosure includes idiopathic (e.g. familial) and acquired forms. Further, epilepsy, in particular before/during acute seizures, may require neuroprotective treatment to reduce brain damage, short term memory loss, cognitive decline, or/and additional seizures (anti-epileptogenesis). Epileptogenesis is a process by which normal brain tissue is transformed into tissue capable of generating spontaneous seizures (Löscher and Brandt, Pharmacol Review, 62.4, 668-700, 2010). Events which may trigger epileptogenic transformations are brain insults, including traumatic brain injury, stroke, infections, tumors, neurodegenerative diseases, and prolonged acute symptomatic seizures, such as complex febrile seizures. However, drugs which alleviate such epileptic processes thereby preventing or reducing secondary epilepsy and/or reducing the number of subsequent seizures are still missing. A need therefore exist for drugs which can be used subsequent to brain insults in order to prevent or diminish epileptogenic processes in the brain tissue thereby preventing secondary (symptomatic) epilepsy and/or associated seizures. It has been shown in the past that lacosamide exhibits neuroprotective effects in various experimental models such as e.g. in animal models of brain ischemia (U.S. Pat. No. 6,133,261) and status epliepticus (US 2006/0009384), or in an in vitro neurotoxicity assay (WO 2008/000513).

The present invention also relates to antiepileptogenic properties of lacosamide. Accordingly, one embodiment of the present disclosure is lacosamide for use in the preventative treatment of patients which experienced brain insults. One embodiment of the present disclosure is lacosamide for use in the prevention or alleviation of epileptogenesis in patients which suffered from brain insults. One embodiment of the present disclosure is lacosamide for use in the prevention of epilepsy and/or epileptic seizures in patients which experienced brain insults. Examples for such brain insults for which lacosamide can be used include traumatic brain injury, stroke, infections, tumors, neurodegenerative diseases, and prolonged acute symptomatic seizures, such as complex febrile seizures. In one embodiment, the brain insult after which lacosamide is being used is traumatic brain injury. In one embodiment, the brain insult in which lacosamide is being used is a brain tumor. In one embodiment, the brain insult during which lacosamide is used is a neurodegenerative disease. In these brain insults potentially triggering epileptogenic processes lacosamide is preferably administered in the form of a modified release formulation disclosed herein.

One embodiment of the present invention thus relates to lacosamide for use in the prophylaxis of epilepsy subsequent to a brain insult, wherein lacosamid is administered as an oral modified release formulation further disclosed herein, preferably for the once daily administration of 400 mg, 600 mg, 700 mg or 800 mg. One embodiment of the present invention relates to lacosamide for use in the prevention or alleviation of epileptogenesis associated with a brain insult, wherein lacosamid is administered as an oral modified release formulation further disclosed herein, preferably for the once daily administration of 400 mg, 600 mg, 700 mg or 800 mg. One embodiment of the present invention relates to lacosamide for use in the prevention or alleviation of epileptogenesis associated with a brain insult, wherein lacosamid is administered as an oral modified release formulation further disclosed herein, preferably for the once daily administration of 400 mg, 600 mg, 700 mg or 800 mg, wherein the brain insult is selected from traumatic brain injury, stroke, infections, tumors, neurodegenerative diseases, and prolonged acute symptomatic seizures, such as complex febrile seizures. One embodiment of the present invention relates to lacosamide for use in the prevention or alleviation of epileptogenesis associated with traumatic brain injury, wherein lacosamide is administered as an oral modified release formulation further disclosed herein, preferably for the once daily administration of 400 mg, 600 mg, 700 mg or 800 mg, most preferably in a daily amount of 600 mg. One embodiment of the present invention relates to lacosamide for use in the prevention or alleviation of epileptogenesis associated with a brain tumor, wherein lacosamid is administered as an oral modified release formulation further disclosed herein, preferably for the once daily administration of 400 mg, 600 mg, 700 mg or 800 mg, most preferably in 600 mg units.

Status epilepticus includes partial or/and generalized seizures. Generalized seizures can be convulsive, such as tonic-clonic, tonic, clonic, or myoclonic seizures, or non-convulsive, such as absences or atonic seizures. Details of the prevention, alleviation or/and treatment of status epilepticus and neuroprotective treatment by lacosamide are described in EP 1 541 138, the disclosure of which is incorporated herein by reference.

Further, epilepsy includes a refractory epileptic condition. The term "refractory epileptic condition" herein refers to an epileptic disease state such as status epilepticus, an epileptic seizure, a repetitive seizure or a seizure cluster that is at least partially or substantially resistant to treatment with one or more anti-epileptic drugs. The term "refractory epileptic conditions" or "refractory epilepsy" such as for example "refractory status epilepticus" used herein refers to an epileptic condition such as a status epilepticus as defined herein exhibiting at least partial or substantial resistance to treatment with one or more anti-epileptic drugs. Such drugs in either case include benzodiazepines, barbiturates and anticonvulsants other than a compound of Formula (I) as defined herein. For example and without limitation, resistance can be exhibited to treatment with one or more drugs selected from diazepam, lorazepam, midazolam, phenobarbital, carbamazepine, phenyloin, fosphenyloin, oxcarbazepine, lamotrigine, gabapentin, pregabalin, valproic acid, pentobarbital, thiopental, propofol and pharmaceutically acceptable salts thereof.

Further, refractory epilepsy as used herein may be initially responsive to treatment with such drugs but becomes at least partially refractory when it lasts for at least about 10 minutes, for example at least about 15 minutes, at least about 20 minutes, at least about 30 minutes, at least about 45 minutes or at least about 60 minutes.

Further, a refractory epileptic condition including refractory status epilepticus can be present a priori, or, in the case of refractory status epilepticus, can be associated with the duration of status epilepticus as indicated above.

Details of the prevention, alleviation or/and treatment of refractory status epilepticus and neuroprotective treatment by lacosamide, as described herein are described in EP 2 035 029 and WO 2007/144196 the disclosure of which is incorporated herein by reference.

If lacosamide is being used in the treatment of refractory or other serious epileptic conditions, such as in the treatment (including the adjunctive treatment) of patients suffering from primary generalized tonic clonic seizures (PGTCS; grand mal), or in the treatment of (symptomatic) generalized seizures secondary to brain insults an increase of the daily administered dosage of lacosamide compared to the maximum daily administered dosage usually given in immediate release form (i.e. up to 400 mg/day) may be required. Accordingly, it has been determined by the present inventors that the presently disclosed modified release formulation of lacosamide is particularly suited for treatment of such severe, or refractory forms of epilepsy because the efficacy/side effect ratio is improved compared to the presently approved IR formulation (see e.g. FIGS. 4A-4C). Hence, one embodiment of the present invention relates to an oral modified release formulation as disclosed herein, for use in the treatment (including the adjunctive treatment) of refractory or otherwise severe forms of epilepsy, including but not limited to PGTCS, or symptomatic generalized seizures. In one embodiment, in the treatment of the recractory or otherwise severe form of epilepsy, e.g. of PGTCS, the modified release formulation of lacosamide will be administered once daily in a total daily amount of at at least 100 mg, at least 200 mg, at least 300 mg, or at least 400 mg, e.g. of about 400 to about 1000 mg, preferably of about 400 to 800 mg, more preferably of about 600 mg per day.

In one aspect the formulation of the present invention may administered as monotherapy or monoprevention of epilepsy or of convulsive conditions or may be given adjunctive to or in combination with at least one further compound in a method for the prevention, alleviation or/and treatment of epileptic seizures, wherein the compound is different from lacosamide, wherein this composition has a synergistic effect in the prevention, alleviation or/and treatment of epileptic seizures as compared to the effect of the compounds (a) or (b) given alone. Details of such combination are disclosed in EP 1 925 314 and EP 2 037 965, the disclosure of which is incorporated herein by reference. The combination may be for the preparation of a medicament for the prevention, alleviation or/and treatment of epileptic seizures. The epileptic seizures may be selected from partial seizures with and without secondary generalisation, primarily generalised seizures, and status epilepticus.

If lacosamide is being used in the monotherapy of epilepsy, such as in the monotherapy of partial onset seizures (with and without secondary generalization), or in the monotherapy of generalized tonic clonic seizures, an increase of the daily administered dosage compared to the daily administered dosage given as adjunctive therapy may be required. Accordingly, it has been determined by the present inventors that the presently disclosed modified release formulation of lacosamide is particularly suited for the monotherapy of epilepsy because the efficacy/side effect ratio is improved compared to the presently approved IR formulation (see e.g. FIGS. 4A-4C). Hence, one embodiment of the present invention relates to a oral modified release formulation as disclosed herein, for use in the monotherapy if epilepsy, preferably in the monotherapy of partial onset seizures or of generalized tonic clonic seizures. In one embodiment, the modified release formulation of lacosamide will be administered as monotherapy once daily in a total daily amount of 100-800 mg, 200-800 mg, or 400-800 mg, preferably 200 mg, 300 mg, 400 mg, 500 mg or 600 mg per day.

The epileptic conditions for which the presently disclosed modified release formulation can be used can also comprise absence seizures. In absence seizures, there is abnormal brain activity without exhibiting motor spasms. The patients will usually not lose normal body posture but appear to be staring into space and may move from one location to another without any purpose. One embodiment of the present invention relates to an oral modified release formulation as disclosed herein, for use in the treatment of absence seizures.

Treatment of Pain Syndromes:

Pain syndromes include, but are not limited to, allodynia, phantom pain, acute and chronic pain, neuropathic pain including central neuropathic pain and peripheral neuropathic pain, painful diabetic neuropathy, painful conditions associated with or/and caused by cortical spreading depression (CSD), pain associated with a mononeuropathy, tumor pain, chemotherapy induced pain, nucleoside induced pain, and nucleoside analogue induced pain, non-inflammatory musculoskeletal pain, pain associated with arthritis or with an arthritic condition.

Allodynia includes, but is not limited to, allodynia as a major and unique pain symptom independent of the nature of the underlying disease, and phantom pain. Details of the prevention, alleviation or/and treatment of allodynia by lacosamide are described in EP 1 243 263, the disclosure of which is incorporated herein by reference.

Acute and chronic pain include, but are not limited to, non neuropathic inflammatory pain including chronic inflammatory pain, rheumatoid arthritis pain, and secondary inflammatory osteoarthritic pain. Details of the prevention, alleviation or/and treatment of acute and chronic pain by lacosamide are described in EP 1 243 262, the disclosure of which is incorporated herein by reference.

Neuropathic pain includes, but is not limited to, pain associated with lesions of the nervous system. Neuropathic pain includes peripheral and central neuropathic pain.

Central neuropathic pain includes, but is not limited to, spinal cord injury pain or/and CNS injury pain. Details of the prevention, alleviation or/and treatment of central neuropathic pain by lacosamide are described in WO 2005/053667 A1, the disclosure of which is incorporated herein by reference.

Peripheral neuropathic pain includes, but is not limited to, pain associated with injury, infection or dysfunction of peripheral sensory nerves.

Painful diabetic neuropathy includes, but is not limited to, a condition associated with painful diabetic neuropathy The painful diabetic neuropathy may be associated with Diabetes mellitus Type I or Diabetes mellitus Type II. Details of the prevention, alleviation or/and treatment of painful diabetic neuropathy by lacosamide are described in WO 2005/092313 A1, the disclosure of which is incorporated herein by reference.

Details of the prevention, alleviation or/and treatment of painful conditions associated with or/and caused by CSD, in particular chronic headache, with Lacosamide are described in WO 2005/099740 A1, the disclosure of which is incorporated herein by reference.

Details of the prevention, alleviation or/and treatment of trigeminal neuropathic pain by lacosamide are described in WO 2005/120539 A2, the disclosure of which is incorporated herein by reference.

Details of the prevention, alleviation or/and treatment of tumor pain, chemotherapy induced pain, nucleoside induced pain and nucleoside analogue induced pain by lacosamide and respective methods are described in WO 2006/021412 A2, the disclosure of which is incorporated herein by reference.

Details of the prevention, alleviation or/and treatment of non-inflammatory musculoskeletal pain, in particular specific manifestations of non-inflammatory musculoskeletal pain such as muscular hyperalgesia or/and allodynia occurring in fibromyalgia, myofascial pain syndrome or/and back pain and respective methods, are described in the application EP 1 754 476, which is included herein by reference.

Details of the prevention, alleviation or/and treatment of motoneuron disorders such as ALS by lacosamide are described in WO 2005/120476 A2, the disclosure of which is incorporated herein by reference.

Details of the prevention, alleviation or/and treatment of dyskinesias by lacosamide are described in WO 2005/110390, the disclosure of which is incorporated herein by reference.

Tremor includes, but is not limited to, essential tremor, physiologic tremor, enhanced physiologic tremor, undetermined tremor syndrome, primary orthostatic tremor, dystonic tremor, task- and position-specific tremors, Parkinsonian tremor syndromes, cerebellar tremor syndromes, Holmes tremor, palatal tremors, neuropathic tremor syndrome, drug-induced and toxic tremor syndromes, psychogenic tremor, myorhythmia, rest tremor, action tremor, postural tremor, kinetic tremor, task- or position-specific tremor or isometric tremor. Details of the prevention, alleviation or/and treatment of tremor by lacosamide are described in WO 2006/000397, the disclosure of which is incorporated herein by reference.

Details of the prevention, alleviation or/and treatment of schizophrenia in an add-on therapy by lacosamide and respective methods are described in WO 2006/079547, the disclosure of which is incorporated herein by reference.

The formulation according to the present invention may be used in methods for the prevention, alleviation, and/or treatment of a disease associated with hyperexcitability. Details of the prevention, alleviation or/and treatment of a disease associated with hyperexcitability by lacosamide and respective methods are described in EP 1 920 780, the disclosure of which is incorporated herein by reference.

In particular, the hyperexcitability may be a sodium channelopathy, i.e. a disease associated with a dysfunction of voltage-gated sodium channels. The sodium channelopathy may be a skeletal muscle selected from the group of (a) inherited myotonia and periodic paralyses (including paramyotonia congenita, potassium aggravated myotonia, myotonia fluctuans, myotonia permanens, aetazolamide responsive myotonia, hyperkalemic periodic paralysis and normokalemic paralysis), (b) movement disorders (including paroxysmal dystonia, Morvan syndrome, and Isaak syndrome), (c) an epileptic condition (including generalized epilepsy with febrile seizures plus (GEFS+); severe myoclonic epilepsy in infancy (SMEI; Dravet's syndrome); benign familial neonatal infantile seizures (BNIFS); intractable childhood epilepsy with generalized tonic-clonic seizures (ICEGTC), and infantile spasms (West syndrome)) and (d) certain pain disorders (such as erythermalgia (=erythromelagia) or familial rectal pain).

Sodium channelopathies are usually rare and difficult to treat diseases, and often require a long-lasting treatment. The chronic administration of the oral modified release formulation of lacosamide represents an excellent option for patients suffering from channelopathies due to the improved efficacy/side effect ratio compared to the oral immediate release formulation.

Accordingly, one embodiment of the present disclosure relates to the modified release formulation of lacosamide disclosed herein for use in the treatment or alleviation of a channelopathy, in particular of a myotonia, or of an epileptic condition (including generalized epilepsy with febrile seizures plus (GEFS+); severe myoclonic epilepsy in infancy (SMEI; Dravet's); benign familial neonatal infantile seizures (BNIFS); intractable childhood epilepsy with generalized tonic-clonic seizures (ICEGTC), and infantile spasms (West syndrome)). In one embodiment, in the treatment of such channelopathies the modified release formulation of lacosamide will be administered once daily in a total daily amount of about 400 to about 800 mg, preferably of about 600 mg per day.

Accordingly, one aspect of the present disclosure relates to a solid pharmaceutical composition for the oral administration of lacosamide, preferably the once daily oral administration of lacosamide, said solid formulation (1) comprising
  (a) about 50 to 1000 mg, preferably about 100 to 900 mg, or about 100 to 800 mg or between 200 and 800 mg of lacosamide (preferably representing about 35 to 50 wt %, or 35 to 45 wt % of the total weight of the formulation) as active ingredient, and
  (b) at least one excipient being a lacosamide release controlling agent and being present
  (b1) in the matrix of said solid composition in an amount of 1 to 50 wt %, preferably 5 to 50 wt %, preferably in an amount of about 5 to 30 wt %, or in an amount of about 10 to 30 wt % relative to the total weight of the formulation and/or
  (b2) in the coating of said solid composition in an amount of 5 to about 35 wt % relative to the total weight of the formulation, and
  (c) preferably one or more further therapeutically acceptable excipients, and
(2) delivering
  (2.1) the in-vitro dissolution profile as further disclosed herein and/or
  (2.2) after once daily administration to animals, in particular to humans a pharmacokinetic profile comprising one or more of the following features:
  (a) a Cmax,ss,norm of 0.016 to 0.023, or of 0.018 to 0.023, preferably of 0.016 to 0.0215, or more preferably of 0.018 to 0.0215 µg lacosamide/ml plasma/mg lacosamide administered per dose in patients with an average distribution volume of 50 L, and/or
  (b) a time point Tmax, ss for reaching the maximum plasma concentration of lacosamide after drug administration in steady state of between 4 and 10 hours, preferably between about 5 and 9 hours, more preferably between about 6.5 and 9 hours, or between about 6.8 and 8.6 hours, and/or
  (c) a dose-normalized AUC in the steady state (AUC, ss, norm) of between about 0.34 to about 0.42 µg/ml/mg, preferably of about 0.400 µg/ml/mg lacosamide per dose in patients with an average distribution volume of 50 L, and/or
  (d) a peak-trough fluctuation (PTF) is below 82%, preferably below 70%, more preferably below 55%, even more preferably below 45%, and/or
  (e) a dose normalized minimum steady state plasma levels Cmin,ss,norm of between 0.0095 and 0.015, and preferably between 0.01 and 0.014 µg lacosamide/ml plasma/mg lacosamide per dosage unit in patients with an average distribution volume of 50 liters, and/or
  (f) a ka value of absorption of between about 0.1/h to about 0.5/h, preferably of between about 0.1/h to about 0.3/h, and more preferably of between about 0.1/h to 0.2/h, for use in the alleviation or treatment (whether adjunctive or as monotherapy) of a disease preferably selected from partial onset seizures, primary generalized tonic clonic seizures, refractory seizures in particular refractory status epilepticus, tremor, tinnitus aureum, a channelopathy [in particular of a myotonia, or of an epileptic condition (including generalized epilepsy with febrile seizures plus (GEFS+); severe myoclonic epilepsy in infancy (SMEI; Dravet's); benign familial neonatal infantile seizures (BNIFS); intractable childhood epilepsy with generalized tonic-clonic seizures (ICEGTC), and infantile spasms (West syndrome)) or in the prevention or alleviation of epileptogenesis in patients which suffered from brain insults, in particular after traumatic brain injury or brain tumors.

Combination Therapy:

In one aspect the formulation of the present invention may be administered in combination with at least one further compound effective in combination therewith in a method to provide enhanced treatment of epilepsy, wherein said second compound may be selected from the group consisting of racetams, gamma amino butyric acid analogs, dibenzazepines, phenyltriazine derivatives, monosaccharide sulfamates, hydantoin derivatives, and barbiturates. The racetam may be selected from the group consisting of piracetam, aniracetam, oxiracetam, pramiracetam, phenylpiracetam, etiracetam, levetiracetam, nefiracetam, rolziracetam, nebracetam, fasoracetam, coluracetam, brivacetam, and seletracetam. The gamma amino butyric acid analog may be selected from the group consisting of gapapentin and pregabalin. The dibenzazepine may be carbamazepine. The phenyltriazine derivative may lamotrigine. The monosaccharide sulfamate may be topiramate. The hydantoin derivative may be selected from the group consisting of ethotoin, phenyloin, mephenyloin, and fosphenyloin. The barbiturate may be selected from the group consisting of phenobarbital, methylphenobarbital, metharbital, pentobarbital, and barbexaclone. In a preferred embodiment, the second compound is selected from the group consisting of levetiracetam, lamotrigine, carbamazepine, topiramate, gabapentin, brivaracetam, seletracetam, zonisamide, felbamate, tiagabine, vigabatrine, diazepam, midazolam, pentobarbital, and ethosuximide.

Most preferably, the second compound is levetiracetam or brivaracetam. Most preferably, the second compound used in the combination therapy with the modified release formulation of lacosamide, either in a fixed combination, or as a part of a "kit" or provided as separate package, is levetiracetam or brivaracetam.

If lacosamide and levetiracetam or brivaracetam are being provided in the same formulation, preferably both compounds are incorporated in the same modified release formulation, i.e. both compounds are either embedded in a joint matrix which is a modified release matrix and/or which matrix is coated by a functional coating, or both compounds are present in different layers of the same formulation wherein both compounds are released with a suitable modified release profile.

If lacosamide and levetiracetam or brivaracetam are being provided as "kit", the modified release formulation comprising lacosamide and a physically separated formulation of levetiracetam or brivaracetam, preferably also a modified release formulation, are being provided in a combination package. Such combination package may comprise a certain number of modified release formulations (e.g. tablets) of lacosamide supplying a patient with sufficient dosing units of lacosamide over a certain period of time, and a respective suitable number of separate levetiracetam or brivaracetam dosing units (e.g. tablets). For the patient's convenience, the lacosamide and the levetiracetam or brivatacetam dosing units may have a different appearance to allow an easy identification of the proper dosing unit to be adminstered; for example, the size, shape and/or color of the respective dosing units and/or of the blisters may differ.

In a preferred aspect, the formulation according to the present invention is for use in a method for the prevention, alleviation, and/or treatment of a disease of the central nervous system. In another preferred aspect, the inventive lacosamide formulation is for use in a method for treating, preventing or alleviating a disease of the central nervous system which is selected from pain, epilepsy, disorders associated with epileptic seizures, essential tremor, bipolar disorder, schizophrenia, obsessive compulsive disorders, dyskinesia, and hyperexcitability disorders. In yet another preferred aspect, the inventive lacosamide formulation is for use in a method for treating, preventing or alleviating a disease of the central nervous system which is selected from epilepsy, disorders associated with epileptic seizures, essential tremor, and bipolar disorder. In yet another preferred aspect, the formulation of the present invention is for use in epileptic seizure prevention and/or the treatment of epilepsy.

Yet another aspect of the present invention is the use of the formulation of the present invention, as described herein, for the preparation of a medicament for the prevention, alleviation, and/or treatment of a disease as described herein.

Yet another aspect of the present invention is a method of treatment of a subject suffering from a disease as described herein, said method comprising administering an effective amount of a formulation according to the present invention to the subject in need of such treatment. The method may comprise administering the formulation once a day.

All publications recited herein are incorporated by reference in their entirety. To the extent of any conflict between this disclosure and that of the recited publications, this disclosure takes precedence.

References
1. Pharmacokinetics, Milo Gibaldi and Donald Perrier (Eds.), Marcel Dekker, New York, 1975
2. Remington, The Science and Practice of Pharmacy, 21th edition 2005, Lippincott Williams & Wilkins, Philadelphia
3. Note for Guidance on the Investigation of Bioavailability and Bioequivalence. London: European Agency for the Evaluation of Medicinal Products; 2001. Report no. CPMP/EWP/QWP/1401/98.

The invention is further illustrated by the following Figures and Examples. These illustrations are given solely by way of example and do not limit the general spirit of the invention.

The Examples of the present invention cover different retardation principles which can achieve the lacosamide release profile of the present invention. For example, lacosamide release profiles as described herein can be achieved by film-coated matrix granules based on ethyl cellulose or PVA/PVP. Other examples provide lacosamide release profiles as described herein by film coated tablets based upon neutral ethyl acetate/methyl methacrylate copolymer or polyvinylacetate. Further examples provide lacosamide release profiles as described herein by a matrix based upon hydrophilic polymer (for example HPC, HPMC, PEG, xanthan or starch), or based upon an inert polymer (for example ethylcellulose, PVA/PVP, ammonium methacrylate copolymer type B). Yet another example provides a lacosamide release profile as described herein by a lipophilic matrix based upon glyceryl dibehenate. Yet another example provides a lacosamide release profile as described herein by a lipophilic matrix capsule based upon glyceryl palmitostearate. A summary of Examples of the present invention is given by the following table.

LACOSAMIDE MR EXAMPLES

| Example No. | Dosage form | Strengths | Lacosamide concentration | Retarding principle | Comment |
|---|---|---|---|---|---|
| 6 | SUD Film coated tablet | 50 mg-200 mg | 40.1% | N/A | IR tablets Wet granulation Non-functional coating |
| 7 | MUD | N/A | 79.7% | Film-coated matrix granules Matrix and functional film-coat is based on ethyl cellulose (Surelease) | Wet granulation with ethyl cellulose and subsequent film-coating in a fluidbed granulator with ethylcellulose Functional film-coating based on ethyl cellulose |
| 8 | MUD | N/A | 75.7% | | |
| 9 | MUD | N/A | 71.9% | | |
| 10 | MUD | N/A | 68.1% | | |
| 11 | MUD | N/A | 80.2% | | |
| 12 | MUD | N/A | 71.9% | Film-coated matrix granules Matrix and functional film-coat is based on PVA/PVP (Kollicoat SR) | Wet granulation with PVA/PVP and subsequent film-coating in a fluidbed granulator with PVA/PVP Functional film-coating based on PVA/PVP |
| 13 | MUD | N/A | 68.5% | | |
| 14 | SUD Tablet | 200 mg | 41.7% | Matrix tablet based on | Formulation is based on IR |

-continued

| Example No. | Dosage form | Strengths | Lacosamide concentration | Retarding principle | Comment |
|---|---|---|---|---|---|
| | | | | hydrophilic polymer: PEG (Polyox WSR 301) Concentration: 8.3% Viscosity: 3'500 mPa · s (1%-solution) | granules Wet granulation |
| 15 | SUD Tablet | 200 mg | 41.7% | Matrix tablet based on hydrophilic polymer: HPMC (Methocel K4M & K100M) Concentration: 8.3% Viscosity: 4'000 mPa · s & 100'000 mPa · s (2%-solution) | Formulation is based on IR granules Wet granulation |
| 16 | SUD Tablet | 200 mg | 41.7% | Matrix tablet based on hydrophilic polymer: HPMC (Methocel K100M) Concentration: 8.3% Viscosity: 100'000 mPa · s (2%-solution) | Formulation is based on IR granules Wet granulation |
| 17 | SUD Tablet | 300 mg | 41.7% | Matrix tablet based on hydrophilic polymer: HPMC (Methocel K100M) Concentration: 8.3% Viscosity: 100'000 mPa · s (2%-solution) | Formulation is based on IR granules Wet granulation |
| 18 | SUD Tablet | 200 mg | 41.7% | Matrix tablet based on hydrophilic polymer: PEG (Polyox WSR 301) Concentration: 8.3% Viscosity: 3'500 mPa · s (1%-solution) | Formulation is based on IR granules Wet granulation |
| 19 | SUD Tablet | 200 mg | 40.0% | Matrix tablet based on hydrophilic polymer: HPMC (Methocel K15M CR) Concentration: 10.0% Viscosity: 15'000 mPa · s (2%-solution) | Formulation is based on IR granules Wet granulation |
| 20 | SUD Tablet | 200 mg | 40.0% | Matrix tablet based on hydrophilic polymer: HPMC (Methocel K15M CR) Concentration: 20.0% Viscosity: 15'000 mPa · s (2%-solution) | Formulation is based on IR granules Wet granulation |
| 21 | SUD Tablet | 200 mg | 40.0% | Matrix tablet based on hydrophilic | Formulation is based on IR granules |

-continued

| Example No. | Dosage form | Strengths | Lacosamide concentration | Retarding principle | Comment |
|---|---|---|---|---|---|
| | | | | polymer: HPMC (Methocel K15M CR) Concentration: 15.0% Viscosity: 15'000 mPa · s (2%-solution) | Wet granulation |
| 22 | SUD Tablet | 200 mg | 40.0% | Matrix tablet based on hydrophilic polymer: HPMC (Methocel K4M) Concentration: 20.0% Viscosity: 4'000 mPa · s (2%-solution) | Formulation is based on IR granules Wet granulation |
| 23 | SUD Tablet | 200 mg | 40.0% | Matrix tablet based on hydrophilic polymer: HPMC (Methocel K100M CR) Concentration: 20.0% Viscosity: 100'000 mPa · s (2%-solution) | Formulation is based on IR granules Wet granulation |
| 24 | SUD Tablet | 200 mg | 40.0% | Matrix tablet based on hydrophilic polymer: HPMC (Methocel K100M DC) Concentration: 20.0% Viscosity: 100'000 mPa · s (2%-solution) | Formulation is based on IR granules Wet granulation |
| 25 | SUD Tablet | 156.4 mg | 92.0% | Matrix tablet based on inert polymer: EC (Surelease) Concentration: 7.2% | Wet granulation |
| 26 | SUD Tablet | 150.7 mg | 87.6% | Matrix tablet based on inert polymer: EC (Surelease) Concentration: 11.4% | Wet granulation |
| 27 | SUD Tablet | 133.6 mg | 78.1% | Matrix tablet based on inert polymer: EC (Surelease) Concentration: 20.9% | Wet granulation |
| 28 | SUD Tablet | 100.6 mg | 58.0% | Matrix tablet based on inert polymer: EC (Surelease) Concentration: 7.8% | Wet granulation |
| 29 | SUD Tablet | 138 mg | 81.1% | Matrix tablet based on inert polymer: PVA/PVP (Kollicoat SR) Concentration: 16.2% | Wet granulation |
| 30 | SUD Tablet | 98.8 mg | 58.1% | Matrix tablet based on inert polymer: PVA/PVP (Kollicoat SR) | Wet granulation |

-continued

| Example No. | Dosage form | Strengths | Lacosamide concentration | Retarding principle | Comment |
|---|---|---|---|---|---|
| 31 | SUD Tablet | 140.4 mg | 81.6% | Concentration: 11.6% Matrix tablet based on inert polymer: ammonium methacrylat copolymer type B (Eudragit RS) Concentration: 14.5% | Wet granulation |
| 32 | SUD Tablet | 100.3 mg | 58.2% | Matrix tablet based on inert polymer: ammonium methacrylat copolymer type B (Eudragit RS) Concentration: 10.3% | Wet granulation |
| 33 | SUD Tablet | 743.8 mg | 87.5% | Matrix tablet based on hydrophilic polymer: Xanthan Concentration: 2.5% | Dry Granulation |
| 34 | SUD Tablet | 425 mg 722.6 mg 850 mg | 85.0% | Matrix tablet based on hydrophilic polymer: Xanthan Concentration: 5% | Dry Granulation |
| 35 | SUD Tablet | 52 mg 400 mg 680.1 mg 800 mg | 80.0% | Matrix tablet based on hydrophilic polymer: Xanthan Concentration: 10% | Dry Granulation |
| 36 | SUD Film coated tablet | 300 mg | 38.1%-39.2% | Matrix tablet based on hydrophilic polymer: HPMC (Methocel K15M CR) Concentration: 9.5-9.8% Viscosity: 15'000 mPa·s (2%-solution) | Formulation is based on IR granules Wet granulation Non-functional coating |
| 37 | SUD Tablet | 25 mg | 39.9% | Matrix tablet based on hydrophilic polymer: HPMC (Methocel K100M) Concentration: 20.0% Viscosity: 100'000 mPa·s (2%-solution) | Dry granulation |
| 38 | SUD Tablet | 600 mg | 59.0% | Matrix tablet based on hydrophilic polymer: HPMC (Methocel K100M) Concentration: 1.8% Viscosity: 100'000 mPa·s (2%-solution) | Dry granulation |
| 39 | SUD Tablet | 600 mg | 59.0% | Matrix tablet based on hydrophilic | Dry granulation |

-continued

| Example No. | Dosage form | Strengths | Lacosamide concentration | Retarding principle | Comment |
|---|---|---|---|---|---|
| | | | | polymer: HPMC (Methocel K100M) Concentration: 2.9% Viscosity: 100'000 mP·s (2%-solution) | |
| 40 | SUD Tablet | 300 mg | 49.7% | Matrix tablet based on inert polymer: PVA/PVP (Kollidon SR) Concentration: 29.6% | Dry granulation |
| 41 | SUD Tablet | 300 mg | 55.2% | Matrix tablet based on hydrophilic polymer: HPC (Klucel EF) Concentration: 16.6% Viscosity: 200-600 mPa·s (10%-solution) | Dry granulation |
| 42 | SUD Tablet | 25 mg | 66.6% | Matrix tablet based on hydrophilic polymer: HPMC (Methocel K100M) Concentration: 33.3% Viscosity: 100'000 mPa·s (2%-solution) | Dry granulation |
| 43 | SUD Tablet | 50 mg | 50% | Matrix tablet based on hydrophilic polymer: HPMC (Benecel K1500LV-PH) Concentration: 10.0% Viscosity: 1500 mPa·s (2% solution) | Dry granulation |
| 44 | SUD Tablet | 50 mg | 50% | Matrix tablet based on hydrophilic polymer: HPMC (Benecel K750 LV-PH) Concentration: 10.0% Viscosity: 750 mPa·s (2% solution) | Dry granulation |
| 45 | SUD Tablet | 300 mg | 42.9% | Matrix tablet based on hydrophilic polymer: HPMC (Benecel K750 LV-PH) Concentration: 12.9% Viscosity: 750 mPa·s (2% solution) | Dry granulation |
| 46 | SUD Tablet | 300 mg | 42.9% | Matrix tablet based on hydrophilic polymer: HPMC (Benecel K750 LV-PH) Concentration: 8.6% Viscosity: 750 mPa·s (2% solution) | Dry granulation |

-continued

| Example No. | Dosage form | Strengths | Lacosamide concentration | Retarding principle | Comment |
|---|---|---|---|---|---|
| 47 | SUD Tablet | 300 mg | 58.4% | Matrix tablet based on hydrophilic polymer: (Pregelatinized) Starch (Swelstar MX-1) Concentration: 11.7% Viscosity: 70 mPa·s (2%-solution) | Dry granulation |
| 48 | SUD Tablet | 50 mg | 20.8% | Lipophilic matrix tablet based on glyceryl dibehenate (Compritol 888 ATO) Concentration: 20.0% Melting point: 65-77° C. | Dry granulation |
| 49 | SUD Capsule | 50 mg | 84.7 | Lipophilic matrix capsule based on glyceryl palmitostearate (Precirol ATO 5) Concentration: 15.3% Melting point: 53-57° C. | Melt embedding |
| 50 | MUD Minitablets in capsule | 5 mg | 33.3% | Matrix tablet based on hydrophilic polymer: HPMC (Benecel K750 LV-PH) Concentration: 20.0% Viscosity: 750 mPa·s (2% solution) | Dry granulation |
| 51 | SUD Film-coated tablets | 50 mg | 41.0-41.8% | Film coated tablet with functional coating based on neutral ethyl acrylate/metyl methacrylate copolymer (Eudragit NE 40 D) Concentration: 2-4% | Wet granulation Functional coating |
| 52 | SUD Film-coated tablets | 50 mg | 51.7-52.2% | Film coated tablet with functional coating based on polyvinylacetate (Kollicoat SR 30 D) Concentration: 2-3% | Wet granulation Functional coating |

Abbreviations:
MUD, multiple unit dosage;
SUD, single unit dosage

Example 1

Correlation Between Side Effects of Lacosamide and Plasma Concentration

Correlation Between Dizziness and Cmax/Tmax

In a thorough QT trial safety profile of lacosamide (LCM) was characterized. During day 2-6 of multiple dose administration of an IR formulation (Vimpat®) of 200 or 400 mg LCM bid 45 times 'DIZZINESS' was detected as adverse event (AE). Time of onset was 1.4+/−0.8 h after actual administration of LCM. This corresponds exactly to the typical time for maximum LCM plasma concentration $t_{max}$ (e.g., 1 h (median, range 1-4-h) at day 6 of SP640).

Example 2

Phase I Study of Lacosamide Pharmacokinetics

The primary objective of this study was to evaluate in a phase 1, single site, open-label, randomized, 3-way crossover, pilot study the pharmacokinetics (PK, or pK) of a single oral dose of 2 different MR formulations of lacosamide (LCM) provided by Examples 19 and 20 in comparison to an IR tablet (Vimpat®) in healthy male subjects (n=12). The study was comprised of 3 treatment periods of 5 days each during which identical procedures have been performed. A single oral dose of study drug was administered on the first day morning of each treatment period following an overnight fast of at least 10 hours. A wash-out period of at least 7 days separated each administration of study drug. The PK variables at each time point of blood sampling included area under the concentration-time curve from time 0 up to the last analytically quantifiable concentration ($AUC_{0-tlast}$), maximum plasma concentration ($C_{max}$), time corresponding to $C_{max}$ ($t_{max}$), plasma concentration, area under the concentration-time curve from time 0 to infinity ($AUC_{0-inf}$), and terminal half-life ($t_{1/2}$). To characterize the PK profile of the MR formulations compared to the IR formulation, $AUC_{0-tlast}$, $C_{max}$, and $t_{max}$ have been assessed.

The secondary objective of this study was to evaluate the safety and tolerability of LCM after single oral administration of 2 different MR formulation tablets and IR tablet. The safety variables included assessment of adverse events (AEs), and other parameters.

Results

The results are summarized in FIG. 1 and the following Tables 1 to 3. In treatment A, the MR formulation of Example 19 ("formulation A") was administered. In treatment B, the MR formulation of Example 20 was administered ("formulation B"). In treatment C, the IR formulation of Example 6 was administered.

TABLE 1 pK parameters determined in a human phase I trial administering the formulation A

| Parameter | n | Treatment A LS Means | Treatment C LS Means | Point estimate for ratio A/C | 90% confidence interval | ANOVA CV (%) |
|---|---|---|---|---|---|---|
| $C_{max}$ (µg/mL) | 12 | 2.58 | 5.45 | 0.47 | [0.43; 0.52] | 13.0 |
| $AUC_{(0-tlast)}$ (µg/mL * h) | 12 | 84.55 | 89.88 | 0.94 | [0.85; 1.04] | 14.9 |
| $AUC_{(0-inf)}$ (µg/mL * h) | 12 | 87.86 | 92.07 | 0.95 | [0.86; 1.06] | 15.5 |

TABLE 2 pK parameters determined in a human phase I trial administering the formulation B

| Parameter | n | Treatment B LS Means | Treatment C LS Means | Point estimate for ratio B/C | 90% confidence interval | ANOVA CV (%) |
|---|---|---|---|---|---|---|
| $C_{max}$ (µg/mL) | 12 | 2.23 | 5.45 | 0.41 | [0.37; 0.45] | 13.0 |
| $AUC_{(0-tlast)}$ (µg/mL * h) | 12 | 77.45 | 89.88 | 0.86 | [0.78; 0.96] | 14.9 |
| $AUC_{(0-inf)}$ (µg/mL * h) | 12 | 80.84 | 92.07 | 0.88 | [0.79; 0.98] | 15.5 |

The pharmacokinetics show that $t_{max}$ after single administration was found to be about 1 h in the comparative IR formulation C, about 12 h in the MR formulation A and about 15 hours for MR formulation B. $C_{max}$ of the MR formulations A and B tested are approximately 47 to 41% of the $C_{max}$ of the comparative IR formulation C ("point estimate" at $t_{max}$), respectively. The ratio of $AUC_{0-tlast}$ and $AUC_{0-inf}$ of the MR formulations and the IR formulation is larger than 94% and 86%, respectively. The acceptance range of the treatment ratios in the view of bioequivalence is [0.8; 1.25] (see reference 3). Taking into account that the respective 90% confidence interval of $AUC_{(0-tlast)}$ for the treatment ratio of formulation NC is within the bioequivalence range, the exposure (bioavailability) between formulation A and comparative formulation C is equivalent. Evaluation for formulation B results in a slightly reduced exposure compared to the comparative IR formulation C, as the 90% confidence interval for the treatment ratio of formulation B/C overlaps with the bioequivalence range.

The incidence of drug-related treatment-emergent adverse events (TEAE) summary (population: safety set) is summarized in Table 3. It turned out that side effects were already reduced after single administration of MR formulations A and B compared with comparative formulation C.

TABLE 3

Incidence of TEAEs in a human phase I trial after administration of formulations A and B

| Treatment A<br>n = 1 (7.7%)<br>[# = 1] | Treatment B<br>n = 2 (15.4%)<br>[# = 5] | Treatment C<br>n = 4 (30.8%)<br>[# = 10] |
|---|---|---|
| paraesthesia | paraesthesia oral<br>chest discomfort<br>anxiety | paraesthesia oral<br>nausea<br>back pain<br>paraesthesia<br>smnolence<br>dizziness<br>dysgeusia |

: number of adverse event reports, n: number of subjects reporting adverse events The data suggest that
A delayed absorption of lacosamide with lower peak concentrations of lacosamide for both new formulations A and B was observed, compared with a comparative IR formulation.
Explorative analysis indicates similar exposure between formulation A and comparative formulation C in terms of $AUC_{(0-tlast)}$. The respective 90% confidence interval for the treatment ratio is within the bioequivalence range of [0.8; 1.25]. Evaluation for formulation B indicates a slightly reduced exposure compared to the comparative IR formulation C.
Lower incidence of drug-related AEs has been observed for both MR formulations A and B compared to the comparative IR formulation C. It is to be expected that the differences in side effects of MR and IR formulations are more pronounced after multiple administration of these formulations, i.e. in steady state conditions.

Example 3

Simulation of Lacosamide Pharmacokinetics, Therapeutic Effect, and Adverse Event Over Time Profile The present simulations combine the simulation of the plasma concentrations profile (pharmacokinetics) with corresponding exposure-response models to a new view of therapeutic effects and the incidence of AEs as a function of time. With this combination the outcome of changes in the pharmacokinetics profile, e.g. by retardation, for the therapeutics effect and the incidence of AEs can be judged.

Model of Pharmacokinetics

The model for simulation of the pharmacokinetics profile is the function (1)

$$C_n(t) = \frac{dose \cdot k_a}{V_d \cdot (k_a - k_e)} \cdot (r_e \cdot e^{-k_e t} - r_a \cdot e^{-k_a t}) \text{ (Reference 2)} \quad \text{Equation (1)}$$

with parameters:

$k_e$ = rate constant of elimination (0.05/h)

$k_a$ = rate constant of absorption ($k_a$ = 2/h for IR formulaion, $k_a$ between 0.1 and 0.5 for MR formulation)

$V_d$ = volume of distribution (50 L)

dose = 200 mg IR vs 400 mg MR dosing interval = 12 h (IR) vs 24 h (MR)

$$r_e = \frac{1 - e^{-nk_e\tau}}{1 - e^{-k_e\tau}}$$

$$r_a = \frac{1 - e^{-nk_a\tau}}{1 - e^{-k_a\tau}}$$

$n$ = number of dosing during repeated dose

Absorption Characteristics of Lacosamide after IR or MR Formulation

Under precondition of a first order process of absorption the amount of absorption over time can be described by the equation:

$$A(t) = 100 \cdot (1 - e^{-k_a \cdot t}) \quad \text{Equation (2)}$$

Figure 2A:
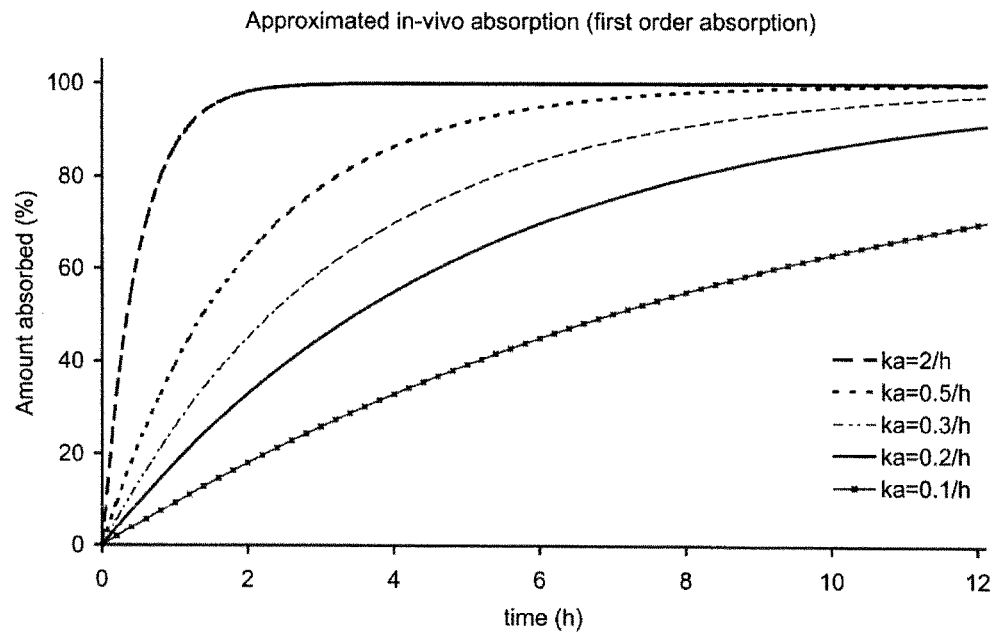

Following Table 4 and FIG. 2A illustrate the amount absorbed over time profiles of lacosamide after oral administration as IR formulation ($k_a$=2/h) or MR formulation ($k_a$=0.1/h, 0.2/h, 0.3/h or 0.5/h).

TABLE 4

Calculated absorption profiles for IR and MR formulations of LCM (Amount absorbed % of dose)

| Time (h) | IR<br>($k_a$ = 2/h) | $k_a$ = 0.5/h | $k_a$ = 0.3/h | $k_a$ = 0.2/h | $k_a$ = 0.1/h |
|---|---|---|---|---|---|
| 0 | 0 | 0 | 0.0 | 0 | 0 |
| 1 | 86.5 | 39.3 | 25.9 | 18.1 | 9.5 |
| 2 | 98.2 | 63.2 | 45.1 | 33.0 | 18.1 |
| 3 | 99.8 | 77.7 | 59.3 | 45.1 | 25.9 |
| 4 | 100.0 | 86.5 | 69.9 | 55.1 | 33.0 |
| 5 | 100.0 | 91.8 | 77.7 | 63.2 | 39.3 |
| 6 | 100.0 | 95.0 | 83.5 | 69.9 | 45.1 |
| 7 | 100.0 | 97.0 | 87.8 | 75.3 | 50.3 |
| 8 | 100.0 | 98.2 | 90.9 | 79.8 | 55.1 |
| 9 | 100.0 | 98.9 | 93.3 | 83.5 | 59.3 |
| 10 | 100.0 | 99.3 | 95.0 | 86.5 | 63.2 |
| 11 | 100.0 | 99.6 | 96.3 | 88.9 | 66.7 |
| 12 | 100.0 | 99.8 | 97.3 | 90.9 | 69.9 |
| 13 | 100.0 | 99.8 | 98.0 | 92.6 | 72.7 |
| 14 | 100.0 | 99.9 | 98.5 | 93.9 | 75.3 |
| 15 | 100.0 | 99.9 | 98.9 | 95.0 | 77.7 |
| 16 | 100.0 | 100.0 | 99.2 | 95.9 | 79.8 |
| 17 | 100.0 | 100.0 | 99.4 | 96.7 | 81.7 |
| 18 | 100.0 | 100.0 | 99.5 | 97.3 | 83.5 |
| 19 | 100.0 | 100.0 | 99.7 | 97.8 | 85.0 |
| 20 | 100.0 | 100.0 | 99.8 | 98.2 | 86.5 |
| 21 | 100.0 | 100.0 | 99.8 | 98.5 | 87.8 |

TABLE 4-continued

Calculated absorption profiles for IR and MR formulations
of LCM (Amount absorbed % of dose)

| Time (h) | IR ($k_a$ = 2/h) | $k_a$ = 0.5/h | $k_a$ = 0.3/h | $k_a$ = 0.2/h | $k_a$ = 0.1/h |
|---|---|---|---|---|---|
| 22 | 100.0 | 100.0 | 99.9 | 98.8 | 88.9 |
| 23 | 100.0 | 100.0 | 99.9 | 99.0 | 90.0 |
| 24 | 100.0 | 100.0 | 99.9 | 99.2 | 90.9 |

Taking into account that lacosamide provides almost 100% bioavailability, which indicates that 100% of the lacosamide released into the intestine is absorbed (i.e. transferred into the plasma), the release kinetics of a solid lacosamide formulation corresponds to the absorption kinetics of lacosamide, provided that the release of lacosamide does not take more than eighteen (18) hours. A release period of more than eighteen (18) hours from the formulation results in a partial loss of active agent, due to passing through the gastro-intestinal tract in yet unreleased form.

Figure 2B:
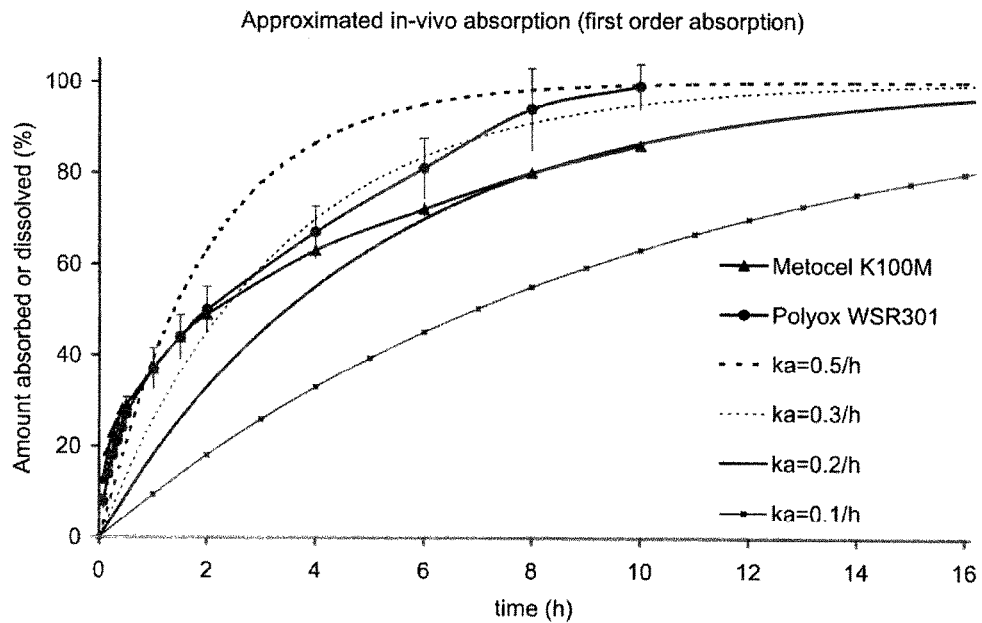
Figure 2C:
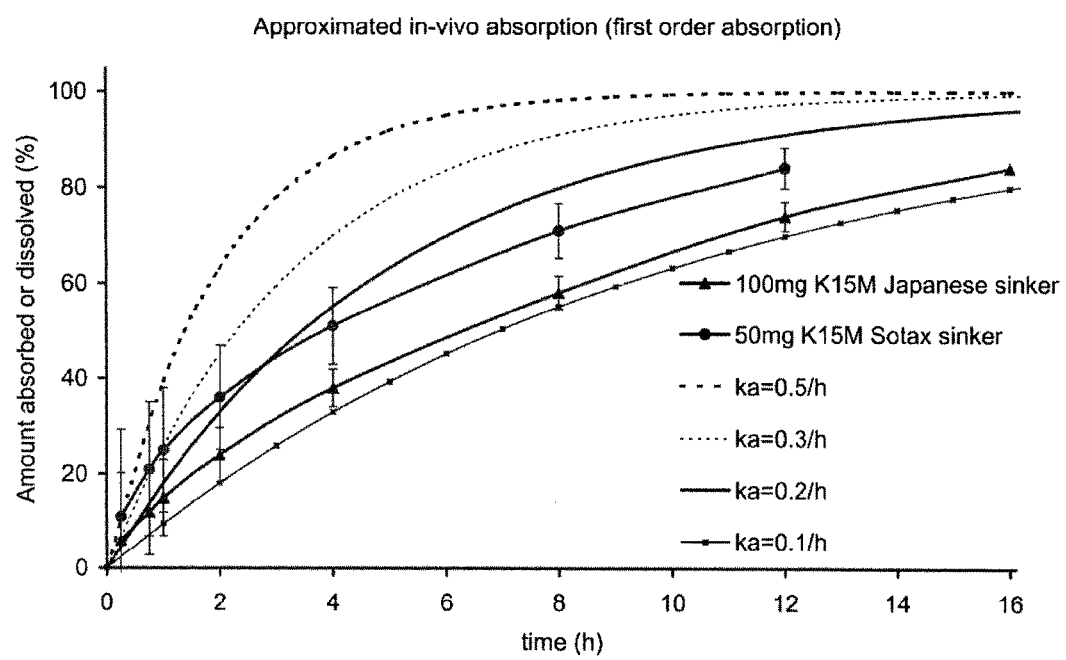

The release kinetics can be described by in-vitro dissolution profiles, obtained by standardized methods, as described in Example 5. FIG. 2B and FIG. 2C describe typical in-vitro dissolution profiles (Metocel K100M, Polyox WSR301, MR compositions of Examples 19 and 20) and the simulated in-vivo absorption data under the condition of a first order absorption with a rate constant of absorption $k_a$=0.1/h, 0.2/h, 0.3/h and 0.5/h. It turned out that the experimentally determined in-vitro dissolution profiles of the MR compositions fit very well with the range of in-vivo absorption covered by simulated formulations with rate constants $k_a$ between 0.1/h and 0.5/h (FIGS. 2B and 2C). Thus, MR formulations of lacosamide can be provided having rate constants $k_a$ selected from the range of 0.1/h and 0.5/h and preferably between 0.1/h and 0.3/h.

Accordingly, the calculation of pharmacokinetic parameters presented below is based upon (a) a direct correlation between the in-vitro dissolution profile of a lacosamide formulation and the in-vivo lacosamide absorption, and (b) the efficacy/side effect ratio of lacosamide can be improved by an appropriate adjustment of the lacosamide release profile from the formulation thereby leading to an improved pharmacokinetic profile.

Pharmacodynamic Model

The therapeutic effect of an anti-epileptic-drug like lacosamide is the reduction of the frequency of seizure episodes. In the exposure-response analysis for LCM, the Emax-model was identified as the appropriate model to illustrate the change of seizure frequency as a function of the LCM concentration in plasma.

$$E(C) = 100 - E_{max} \cdot \frac{C(t)}{k_d + C(t)} \qquad \text{Equation (3)}$$

With C(t) (see equation 1) is the plasma concentration at time t, $E_{max}$ is the maximum effect (71%, see Example 54) describing the maximal decrease of seizures by LCM with reference to the baseline value before LCM treatment. The kd value is the concentration for half of the maximum effect (2.917 μg/mL corresponding to an AUC,tau,ss of 35 μg/mL*h, see Example 54).

Incidence of an Adverse Event

As one of the most common adverse events (AE, also termed herein treatment-emergent adverse events, TEAE) after multiple doses of lacosamide 'dizziness' was identified in the human clinical study of Example 2). The incidence of this AE was tested by a logit-regression with the model AE=lacosamide concentration in plasma. The evaluation was done by the SAS procedure LOGIT based on the data of said clinical study at day 6. The values for parameters intercept A and slope B of the logit equation logit(concentration)=$A+B$*concentration are
$A$=−2.4683 and $B$=0.1414.

Logit-function was used to simulate the probability (p) of the AE dizziness as a function of the lacosamide concentration (C).

$$p(C) = \frac{e^{A+B \cdot C}}{1 + e^{A+B \cdot C}} \qquad \text{Equation (4)}$$

Results

Pharmacokinetics

The LCM plasma concentrations after MR formulation (ka=0.1/h) have the same mean level as illustrated for administration of IR formulation. Peak concentrations are lower under MR formulation (ka=0.1/h), trough concentrations are higher than under IR formulation (FIG. 5A). The main parameters of pharmacokinetics under steady state condition are summarized in Table 5.

Therapeutic Effect

Figure 4B:
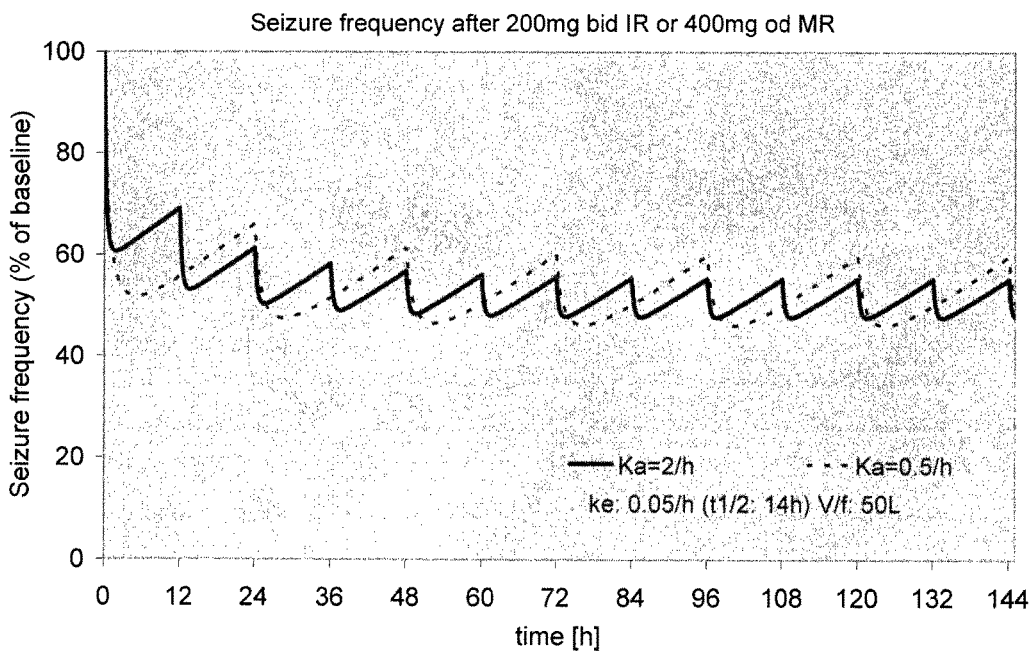

Illustration shows a decrease of the seizure frequency by about 50% under multiple dose of 200 mg bid as IR or 400 mg od preferred MR formulation (ka=0.1/h). Comparison of both curves suggest that the therapeutic effect under IR formulation is very similar for both formulations using different dosing intervals of 12 h (IR) or 24 h (MR) (FIG. 4B).

Adverse Event (Dizziness)

Figure 4C:
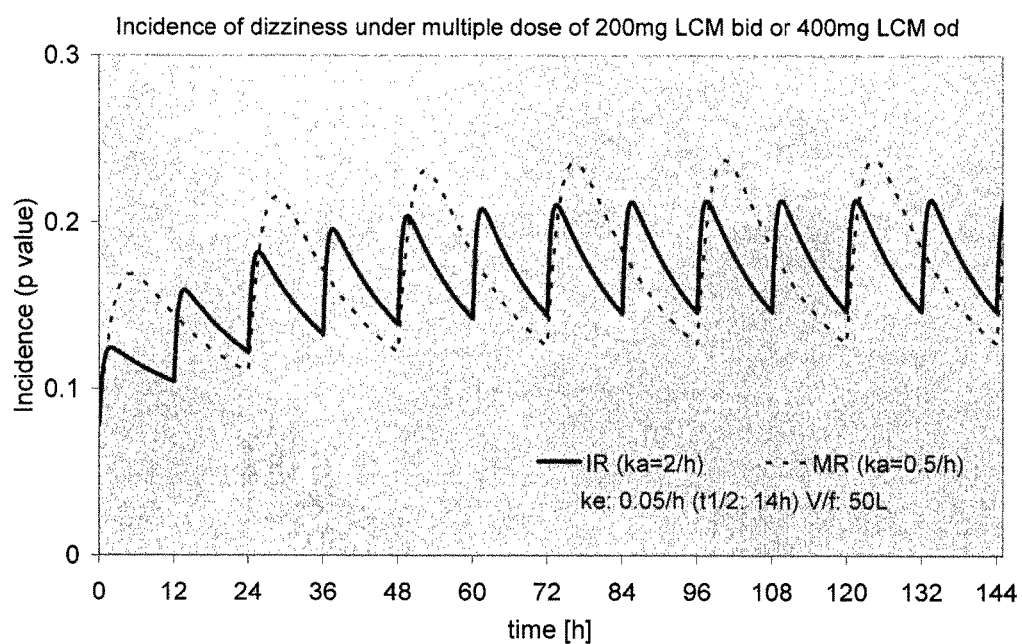

The highest incidence of the AE is given under IR formulation (p=0.213) compared to preferred MR formulation (ka=0.1/h) (p=0.183) (FIG. 4C).

The increase of rate of absorption for MR formulation (0.2/h instead of 0.1/h) results in:
- maximum of LCM plasma concentration is the very similar after MR formulation compared to IR formulation (FIG. 3A and Table 5) using different dosing intervals of 12 h (IR) or 24 h (MR)
- effect over time profile almost is the very similar after MR than IR formulation (FIG. 3B) using different dosing intervals of 12 h (IR) or 24 h (MR)
- same incidence of an AE like dizziness (FIG. 3C) using different dosing intervals of 12 h (IR) or 24 h (MR).

TABLE 5

Parameters of LCM pharmacokinetics under steady-state condition (dose 200 mg bid for IR and 400 mg od for MR)

| Parameter | Vd (L) | IR formulation ka = 2/h dose = 200 mg | MR formulation ka = 0.1/h dose = 400 mg | MR formulation ka = 0.2/h dose = 400 mg | MR formulation ka = 0.3/h dose = 400 mg | MR formulation ka = 0.5/h dose = 400 mg |
|---|---|---|---|---|---|---|
| Cmax, ss (µg/mL) | 40 | 10.29 | 9.31 | 10.13 | 10.74 | 11.53 |
|  | 50 | 8.23 | 7.45 | 8.1 | 8.59 | 9.22 |
|  | 70 | 5.88 | 5.32 | 5.79 | 6.14 | 6.59 |
| Cmax, ss, norm (µg/mL/mg) | 40 | 0.0514 | 0.0233 | 0.0253 | 0.0268 | 0.0288 |
|  | 50 | 0.0412 | 0.0186 | 0.0203 | 0.0215 | 0.0231 |
|  | 70 | 0.0294 | 0.0133 | 0.0145 | 0.0153 | 0.0165 |
| tmax, ss (h) |  | 1.4 | 8.6 | 6.8 | 5.8 | 4.4 |
| tau (h) |  | 12 | 24 | 24 | 24 | 24 |
| Cmin, ss (µg/mL) | 40 | 6.23 | 6.63 | 5.63 | 5.16 | 4.79 |
|  | 50 | 4.98 | 5.3 | 4.5 | 4.13 | 3.83 |
|  | 70 | 3.56 | 3.79 | 3.21 | 2.95 | 2.74 |
| Cmin, ss, norm (µg/mL/mg) | 40 | 0.0311 | 0.0166 | 0.0141 | 0.0129 | 0.0120 |
|  | 50 | 0.0249 | 0.0133 | 0.0113 | 0.0103 | 0.0096 |
|  | 70 | 0.0178 | 0.0095 | 0.0080 | 0.0074 | 0.0068 |
| AUCtau, ss (µg/mL * h) | 40 | 99.9 | 199.9 | 199.9 | 199.9 | 199.9 |
|  | 50 | 79.9 | 159.9 | 159.9 | 159.9 | 159.9 |
|  | 70 | 57.1 | 114.2 | 114.2 | 114.2 | 114.2 |
| AUCtau, ss, norm (µg/mL * h/mg) | 40 | 0.499 | 0.500 | 0.500 | 0.500 | 0.500 |
|  | 50 | 0.400 | 0.400 | 0.400 | 0.400 | 0.400 |
|  | 70 | 0.285 | 0.286 | 0.286 | 0.286 | 0.286 |
| PTF (%) |  | 48.8 | 32.3 | 54.0 | 66.9 | 80.9 |

Cmax, ss = maximum of plasma concentration in steady state;
Cmax, ss, norm = Cmax, ss normalized by dose administered;
tmax, ss = time after actual administration to reach Cmax, ss;
Cmin, ss = maximum of plasma concentration in steady state;
Cmin, ss, norm = Cmin, ss normalized by dose administered;
AUCtau, ss = area under the curve for the dosing interval tau (=12 h for IR or =24 h for MR formulation) in steady state;
AUCtau, ss, norm = AUCtau, ss normalized by dose administered;
PTF = peak to trough fluctuation

Example 4

Simulation of Pharmacokinetics Based Upon Human Phase I Trial

By the method described in Example 3, we determined the pharmacokinetic parameters of the MR formulation of Example 19 and the comparative IR formulation (Vimpat®, Example 6) for repeated dose (200 mg lacosamide bid), based upon the $k_a$ and $k_e$ determined from the data obtained in the human clinical phase I trial of Example 2.

Based on equation $$CL = V \cdot k_e = \frac{dose}{AUC} \quad \text{Equation (5)}$$

volume of distribution V can be calculated by:

$$V = \frac{dose}{AUC \cdot k_e} \quad \text{Equation (6)}$$

With measured $AUC_{(0-inf)}$ of 87.86 µg/mL*h for treatment A (formulation of Example 6) and 92.86 µg/mL*h for treatment C (comparative formulation Vimpat®) and calculated $k_e$ of 0.0537/h for treatment A and 0.05576/h for treatment C (all values geometric means reported in Example 2) V is approximated as:

=42.4 L for treatment A
=38.6 L for treatment C

TABLE 6

| | PK parameters for simulations | |
|---|---|---|
| Treatment | MR Formulation A Example 19 | IR Formulation C Vimpat® Example 6 |
| $k_a$ (1/h) | 0.14 | 2 |
| $k_e$ (1/h) | 0.0537 | 0.05576 |
| Vd (L) | 42.4 | 38.6 |

The results of the simulation are depicted in FIG. 6. Table 7 describes the parameters determined by the simulation.

TABLE 7

| Parameter | IR 200 mg bid ka = 2, V = 38.6 L | IR ka = 2, V = 50 L (normalized) | MR 400 mg od ka = 0.14, V = 42.4 L | MR 400 mg od ka = 0.14, V = 50 L (normalised) |
|---|---|---|---|---|
| tmax, ss (h) | 1.5 | 1.5 | 7.8 | 7.8 |
| Cmax, ss (µg/mL) | 9.78 | 7.55 | 8.58 | 7.28 |
| Cmax, ss, norm (µg/ml) | 0.049 | 0.038 | 0.022 | 0.018 |
| Cmin, ss (µg/mL) | 5.59 | 4.32 | 5.27 | 4.47 |
| Cmin, ss, norm (µg/mL) | 0.028 | 0.022 | 0.013 | 0.011 |
| PTF (%) | 54.2 | 54.2 | 45.2 | 45.2 |
| AUCtau, ss (µg/mL) | 92.8 | 71.64 | 175.6 | 148.9 |

TABLE 7-continued

| Parameter | IR 200 mg bid ka = 2, V = 38.6 L | IR ka = 2, V = 50 L (normalized) | MR 400 mg od ka = 0.14, V = 42.4 L | MR 400 mg od ka = 0.14, V = 50 L (normalised) |
|---|---|---|---|---|
| AUCtau, ss, norm (μg/mL) | 0.464 | 0.358 | 0.439 | 0.372 |

As can be seen from FIG. 6 and Table 7, the modified release formulation of treatment A (Example 6) provides largely reduced PTF, compared with the comparative IR formulation C. The simulated ratio of $AUC_{0\text{-}tlast}$ and $AUC_{0\text{-}tlast}$ of the MR formulation and the IR formulation is 94.6%, indicating a similar exposure (bioavailability) between formulation A and comparative formulation C, as determined experimentally for a single dose administration in Example 2.

By the reduced PTF (reduced Cmax), the formulation of Example 19 is expected to provide an improved side effect profile (in particular reduced dizziness), compared with the comparative IR formulation. The similar exposure indicates that the clinical efficacy is expected to be similar to that of the comparative IR formulation.

It is concluded that other formulations having a similar release profile, as determined for instance by the method of Example 5, are also expected to provide an improved side effect profile, while maintaining the clinical efficacy, compared with a comparative IR formulation. In the following Examples 7 to 35 such beneficial solid lacosamide MR formulations are described. Also described are comparative IR formulations (Example 6).

Example 5

In Vitro Dissolution Test of Solid Lacosamide Formulations

USP method <711> and Ph.Eur. 2.9.3, respectively, refer to an in vitro dissolution test for pharmaceutical compositions. In the present invention a paddle apparatus 2 as described in method <711> of the US Pharmacopoeia (edition 33) and in chapter 2.9.3 of the Pharmacopoeia European (edition 6.8), respectively, with 900 mL of 0.1 molar hydrochloric acid at a stirring speed of 75 rpm at 37±0.5° C. was used to determine the in vitro release of Lacosamide from solid lacosamide formulations.

The amount of Lacosamide released at any time was determined via UV spectrometric detection. The values shown have been averaged over at least 3 samples in each case.

Example 6

Vimpat® IR Tablets

Immediate release tablets with following composition per tablet were produced in the following way with batch sizes varying from 1 to 750 kg:

| Component | Quantity [mg] | | | |
|---|---|---|---|---|
| | 50 mg vs. 124.8 mg | 100 mg vs. 249.6 mg | 150 mg vs. 374.4 mg | 200 mg vs. 499.2 mg |
| Lacosamide | 50.0 | 100.0 | 150.0 | 200.0 |
| Crospovidone | 10.0 | 20.0 | 30.0 | 40.0 |
| Cellulose, microcrystalline (type 102) | 14.0 | 28.0 | 42.0 | 56.0 |
| Hydroxypropylcellulose (low substituted) | 12.5 | 25.0 | 37.5 | 50.0 |
| Hydroxypropylcellulose | 1.0 | 2.0 | 3.0 | 4.0 |
| Silicified microcrystalline cellulose[a] | 31.3 | 62.6 | 93.9 | 125.2 |
| Magnesium stearate | 1.2 | 2.4 | 3.6 | 4.8 |
| Water, purified[b] | q.s. | q.s. | q.s. | q.s. |
| Tablet core | 120.0 | 240.0 | 360.0 | 480.0 |
| Opadry® II G or Opadry® II F[c] from Colorcon company | 4.8 | 9.6 | 14.4 | 19.2 |
| Water, purified[b] | q.s. | q.s. | q.s. | q.s. |
| Total | 124.8 | 249.6 | 374.4 | 499.2 |

[a]Silicified microcrystalline cellulose contains 98% cellulose, microcrystalline and 2% silica, colloidal anhydrous
[b]Water is evaporated during process and is not present in final product; q.s. = quantum satis, as much as needed
[c]Opadry® II G and Opadry® II F are non-functional coating systems with polyvinyl alcohol as film former 1) The binder solution was prepared by dissolving hydroxypropylcellulose in water.
2) Lacosamide, microcrystalline cellulose and low-substituted hydroxypropylcellulose were sieved (seiving and screening of lacosamide and other exclipients in this and the following examples was usually performed by passing trough 1-2 mm sieves/screens), transferred into a high-shear granulator and mixed.
3) The binder solution was added to the dry mixture under stirring.
4) The mixture was granulated (scraping down the sides and lid before and after, which was usually done in the granulation processes described in this and the following examples herein).
5) The wet granules were transferred into a fluid bed dryer and the granules were dried with an inlet air temperature of about 70° C.±5° C. and a product temperature of NMT 50° C. until the loss on drying was NMT 3.0%.
6) The dried granules were sieved
7) Silicified microcrystalline cellulose and crospovidone were screened.
8) The granules and the two ingredients from the previous step were blended.
9) Magnesium stearate was sieved together with a part of the blend from the previous step.
10) This pre-mixture was combined with the residual blend and finally blended
11) The finished final blend was compressed to tablets.
12) Purified water is dispensed into a vessel and the appropriate Opadry II coating system is added while stirring.
13) The coating suspension is stirred for a minimum of 45 min.
14) The tablets are coated in a pan coating system with the coating suspension until the particular mean weight is reached.

The in vitro release of lacosamide was measured according to USP (edition 24) method <711>, dissolution apparatus 2, in 900 mL of 0.1N HCl at 75 rpm and is given in the following table.

| Time [min] | Released total amount of active ingredient [%] | | | |
|---|---|---|---|---|
| | 50 mg vs. 124.8 mg | 100 mg vs. 249.6 mg | 150 mg vs. 374.4 mg | 200 mg vs. 499.2 mg |
| 15 | 97 | 97 | 99 | 98 |
| 30 | 98 | 97 | 99 | 98 |

Example 7

Granules

Granules with following composition were produced in the following way on a batch size of about 2-3 kg:

| Component | Quantity | Particle size[d] |
|---|---|---|
| a) Granules: | | $D_{10}$ = 142 µm |
| | | $D_{50}$ = 388 µm |
| | | $D_{90}$ = 778 µm |
| Lacosamide | 92.8 wt-% | |
| Surelease☐ E-7-19030 from Colorcon company[a,b] | 7.2 wt-% | |
| Water, purified[c] | q.s. | |
| b) Coating: | | |
| Surelease☐ E-7-19030 from Colorcon company[a,b] | 100.0 wt-% | |
| Water, purified[c] | q.s. | |
| c) Total (film coated granules): | | $D_{10}$ = 267 µm |
| | | $D_{50}$ = 545 µm |
| | | $D_{90}$ = 915 µm |
| Lacosamide | 79.7 wt-% | |
| Surelease☐ E-7-19030 from Colorcon company[a,b] | 20.3 wt-% | |
| Water, purified[c] | q.s. | |

[a]Surelease☐ E-7-19030 is an aqueous dispersion with a solid content of 25 wt-% consisting of ethylcellulose, dibutyl sebacat, oleic acid, ammonium hydroxide and colloidal anhydrous silica
[b]Water is evaporated during process and is not present in final product, 20.3 wt-% in the final product corresponds to 81.2 wt-% of 25 wt-% Surelease☐ E-7-19030 dispersion
[c]Water is evaporated during process and is not present in final product, q.s. = quantum satis, as much as needed
[d]The particle size distribution was determined by a sieving test. The sieving test of the granules/powders was performed and analyzed according to 2.9.12 EP and 2.9.38 EP. $D_{10}$, $D_{50}$ and $D_{90}$, respectively, represent mass diameters correlating to 10%, 50% and 90%, respectively, of the mass of the investigated granules/powders 1) The binder solution was prepared by diluting Surelease® E-7-19030 dispersion with purified water to a concentration of 15 wt-%.
2) Lacosamide was weighed, sieved and transferred into a high-shear granulator.
3) The binder solution was added to Lacosamide under continuous stirring.
4) The mixture was granulated for about 2-3 minutes.
5) The wet granules were sieved, and dried for about 21 h with a temperature of about 45° C.
6) The dried granules were sieved and transferred to the fluid bed granulator.
7) The binder solution was prepared by diluting Surelease® E-7-19030 dispersion with purified water to concentration of 15 wt-%. Water and Surelease® E-7-19030 were mixed until a homogenous dispersion was formed and screened.
8) The spray granulation was performed with inlet air temperature ranging from 30° C. to 74° C. The product temperature was kept constant between 30° C. to 32° C. and the spray rate ranged from 9.4 g/min to 24 g/min.
9) After the target amount of binder solution was sprayed, the granules were passed through a 1.6 mm sieve and transferred into a tray dryer. The granules were dried for at least 24 h with a temperature of about 45° C.

The in vitro release of lacosamide was measured according to USP (edition 24) method <711>, dissolution apparatus 2, in 900 mL of 0.1N HCl at 75 rpm and is given in the following table.

| Time [min] | Released total amount of active ingredient [%] | |
|---|---|---|
| | Granules | Film-coated granules |
| 5 | 42 | 1 |
| 10 | 87 | 4 |
| 15 | 98 | 8 |
| 20 | 99 | 11 |
| 25 | 100 | 15 |
| 30 | 100 | 18 |
| 60 | 99 | 36 |
| 90 | 99 | 50 |
| 120 | 99 | 61 |
| 150 | 99 | 69 |
| 180 | 99 | 75 |
| 240 | 98 | 84 |
| 300 | 98 | 89 |
| 360 | 98 | 93 |
| 480 | 98 | 97 |

Example 8

Granules with following composition were produced in the following way on a batch size of about 2-3 kg:

| Component | Quantity | Particle size[d] |
|---|---|---|
| a) Granules | | $D_{10}$ = 142 µm |
| | | $D_{50}$ = 388 µm |
| | | $D_{90}$ = 778 µm |
| Lacosamide | 92.8 wt-% | |
| Surelease☐ E-7-19030 from Colorcon company[a,b] | 7.2 wt-% | |
| Water, purified[c] | q.s. | |
| b) Coating: | | |
| Surelease☐ E-7-19030 from Colorcon company[a,b] | 100.0 wt-% | |
| Water, purified[c] | q.s. | |
| c) Total (film coated granules): | | $D_{10}$ = 296 µm |
| | | $D_{50}$ = 610 µm |
| | | $D_{90}$ = 967 µm |
| Lacosamide | 75.7 wt-% | |
| Surelease☐ E-7-19030 from Colorcon company[a,b] | 24.3 wt-% | |
| Water, purified[c] | q.s. | |

[a]Surelease☐ E-7-19030 is an aqueous dispersion with a solid content of 25 wt-% consisting of ethylcellulose, dibutyl sebacat, oleic acid, ammonium hydroxide and colloidal anhydrous silica
[b]Water is evaporated during process and is not present in final product, 24.3 wt-% in the final product corresponds to 97.2 wt-% of 25 wt-% Surelease☐ E-7-19030 dispersion
[c]Water is evaporated during process and is not present in final product, q.s. = quantum satis, as much as needed
[d]The particle size distribution was determined by a sieving test. The sieving test of the granules/powders was performed and analyzed according to 2.9.12 EP and 2.9.38 EP. $D_{10}$, $D_{50}$ and $D_{90}$, respectively, represent mass diameters correlating to 10%, 50% and 90%, respectively, of the mass of the investigated granules/powders Manufacturing process: as described for example 7

The in vitro release of lacosamide was measured according to USP (edition 24) method <711>, dissolution apparatus 2, in 900 mL of 0.1N HCl at 75 rpm and is given in the following table.

| Time | Released total amount of active ingredient [%] | |
|---|---|---|
| [min] | Granules | Film-coated granules |
| 5 | 42 | 1 |
| 10 | 87 | 3 |
| 15 | 98 | 7 |
| 20 | 99 | 10 |
| 25 | 100 | 14 |
| 30 | 100 | 17 |
| 60 | 99 | 34 |
| 90 | 99 | 48 |
| 120 | 99 | 60 |
| 150 | 99 | 68 |
| 180 | 99 | 76 |
| 240 | 98 | 87 |
| 300 | 98 | 95 |
| 360 | 98 | 100 |
| 480 | 98 | 106 |

Example 9

Granules with following composition were produced in the following way on a batch size of about 2-3 kg:

| Component | Quantity | Particle size[d] |
|---|---|---|
| a) Granules: | | $D_{10}$ = 142 µm |
| | | $D_{50}$ = 388 µm |
| | | $D_{90}$ = 778 µm |
| Lacosamide | 92.8 wt-% | |
| Surelease E-7-19030 from Colorcon company[a,b] | 7.2 wt-% | |
| Water, purified[c] | q.s. | |
| b) Coating: | | |
| Surelease E-7-19030 from Colorcon company[a,b] | 100.0 wt-% | |
| Water, purified[c] | q.s. | |
| c) Total (film coated granules): | | $D_{10}$ = 301 µm |
| | | $D_{50}$ = 608 µm |
| | | $D_{90}$ = 995 µm |
| Lacosamide | 71.9 wt-% | |
| Surelease E-7-19030 from Colorcon company[a,b] | 28.1 wt-% | |
| Water, purified[c] | q.s. | |

[a]Surelease E-7-19030 is an aqueous dispersion with a solid content of 25 wt-% consisting of ethylcellulose, dibutyl sebacat, oleic acid, ammonium hydroxide and colloidal anhydrous silica
[b]Water is evaporated during process and is not present in final product, 28.1 wt-% in the final product corresponds to 112.4 wt-% of 25 wt-% Surelease E-7-19030 dispersion
[c]Water is evaporated during process and is not present in final product, q.s. = quantum satis, as much as needed
[d]The particle size distribution was determined by a sieving test. The sieving test of the granules/powders was performed and analyzed according to 2.9.12 EP and 2.9.38 EP. $D_{10}$, $D_{50}$ and $D_{90}$, respectively, represent mass diameters correlating to 10%, 50% and 90%, respectively, of the mass of the investigated granules/powders 1) Manufacturing process: as described for example 7.

The in vitro release of lacosamide was measured according to USP (edition 24) method <711>, dissolution apparatus 2, in 900 mL of 0.1N HCl at 75 rpm and is given in the following table.

| Time | Released total amount of active ingredient [%] | |
|---|---|---|
| [min] | Granules | Film-coated granules |
| 5 | 42 | 0 |
| 10 | 87 | 2 |
| 15 | 98 | 3 |
| 20 | 99 | 5 |
| 25 | 100 | 6 |
| 30 | 100 | 8 |
| 60 | 99 | 16 |
| 90 | 99 | 23 |
| 120 | 99 | 30 |
| 150 | 99 | 36 |
| 180 | 99 | 41 |
| 240 | 98 | 50 |
| 300 | 98 | 57 |
| 360 | 98 | 65 |
| 480 | 98 | 76 |

Example 10

Granules with following composition were produced in the following way on a batch size of about 2-3 kg:

| Component | Quantity | Particle size[d] |
|---|---|---|
| a) Granules: | | $D_{10}$ = 142 µm |
| | | $D_{50}$ = 388 µm |
| | | $D_{90}$ = 778 µm |
| Lacosamide | 92.8 wt-% | |
| Surelease E-7-19030 from Colorcon company[a,b] | 7.2 wt-% | |
| Water, purified[c] | q.s. | |
| b) Coating: | | |
| Surelease E-7-19030 from Colorcon company[a,b] | 100.0 wt-% | |
| Water, purified[c] | q.s. | |
| c) Total (film coated granules): | | $D_{10}$ = 274 µm |
| | | $D_{50}$ = 552 µm |
| | | $D_{90}$ = 983 µm |
| Lacosamide | 68.1 wt-% | |
| Surelease E-7-19030 from Colorcon company[a,b] | 31.9 wt-% | |
| Water, purified[c] | q.s. | |

[a]Surelease E-7-19030 is an aqueous dispersion with a solid content of 25 wt-% consisting of ethylcellulose, dibutyl sebacat, oleic acid, ammonium hydroxide and colloidal anhydrous silica
[b]Water is evaporated during process and is not present in final product, 31.9 wt-% in the final product corresponds to 127.6 wt-% of 25 wt-% Surelease E-7-19030 dispersion
[c]Water is evaporated during process and is not present in final product, q.s. = quantum satis, as much as needed
[d]The particle size distribution was determined by a sieving test. The sieving test of the granules/powders was performed and analyzed according to 2.9.12 EP and 2.9.38 EP. $D_{10}$, $D_{50}$ and $D_{90}$, respectively, represent mass diameters correlating to 10%, 50% and 90%, respectively, of the mass of the investigated granules/powders 1) Manufacturing process: as described for example 7 except for step 9.

Step 9: After the target amount of binder solution was sprayed, the granules were dried in a fluid bed granulator until a product temperature of 45° C. was achieved. The dried granules were sieved.

The in vitro release of lacosamide was measured according to USP (edition 24) method <711>, dissolution apparatus 2, in 900 mL of 0.1N HCl at 75 rpm and is given in the following table.

| Time | Released total amount of active ingredient [%] | |
|---|---|---|
| [min] | Granules | Film-coated granules |
| 5 | 42 | 4 |
| 10 | 87 | 16 |

-continued

| Time [min] | Released total amount of active ingredient [%] | |
|---|---|---|
| | Granules | Film-coated granules |
| 15 | 98 | 22 |
| 20 | 99 | 24 |
| 25 | 100 | 26 |
| 30 | 100 | 28 |
| 60 | 99 | 33 |
| 90 | 99 | 37 |
| 120 | 99 | 41 |
| 150 | 99 | 44 |
| 180 | 99 | 47 |
| 240 | 98 | 52 |
| 300 | 98 | 56 |
| 360 | 98 | 60 |
| 480 | 98 | 67 |

Example 11

Granules with following composition were produced in the following way on a batch size of about 2 kg:

| Component | Quantity | Particle size[d] |
|---|---|---|
| a) Granules: | | $D_{10}$ = 142 µm |
| | | $D_{50}$ = 388 µm |
| | | $D_{90}$ = 778 µm |
| Lacosamide | 92.8 wt-% | |
| Surelease® E-7-19030 from Colorcon company[a,b] | 7.2 wt-% | |
| Water, purified[c] | q.s. | |
| b) Coating: | | |
| Surelease® E-7-19030 from Colorcon company[a,b] | 100.0 wt-% | |
| Water, purified[c] | q.s. | |
| c) Total (film coated granules): | | $D_{10}$ = 174 µm |
| | | $D_{50}$ = 441 µm |
| | | $D_{90}$ = 840 µm |
| Lacosamide | 80.2 wt-% | |
| Surelease® E-7-19030 from Colorcon company[a,b] | 19.8 wt-% | |
| Water, purified[c] | q.s. | |

[a]Surelease® E-7-19030 is an aqueous dispersion with a solid content of 25 wt-% consisting of ethylcellulose, dibutyl sebacat, oleic acid, ammonium hydroxide and colloidal anhydrous silica
[b]Water is evaporated during process and is not present in final product, 19.8 wt-% in the final product corresponds to 79.2 wt-% of 25 wt-% Surelease® E-7-19030 dispersion
[c]Water is evaporated during process and is not present in final product, q.s. = quantum satis, as much as needed
[d]The particle size distribution was determined by a sieving test. The sieving test of the granules/powders was performed and analyzed according to 2.9.12 EP and 2.9.38 EP. $D_{10}$, $D_{50}$ and $D_{90}$, respectively, represent mass diameters correlating to 10%, 50% and 90%, respectively, of the mass of the investigated granules/powders 1) The binder solution was prepared by diluting Surelease® E-7-19030 dispersion with purified water to concentration of 15 wt-%. The water and Surelease® E-7-19030 were mixed until a homogenous dispersion was formed.
2) Lacosamide was sieved and transferred into a high-shear granulator.
3) The binder solution was added to Lacosamide for about 1 minute under continuous stirring.
4) The mixture was granulated for about 2-3 minutes.
5) The wet granules were sieved and transferred into a tray dryer. The granules were dried for about 21 h with a temperature of about 45° C.
6) The dried granules were sieved, weighed and transferred to the fluid bed granulator.
7) The binder solution was prepared by diluting Surelease® E-7-19030 dispersion with purified water to concentration of 15 wt-%. The water and Surelease® E-7-19030 were mixed until a homogenous dispersion was formed and passed through 1 mm screen.
8) The spray granulation was performed with inlet air temperature of ranging 55° C. to 88° C. The product temperature was kept between 28° C. to 46° C. and the spray rate ranging from 3.8 g/min to 16.2 g/min.
9) After the target amount of binder solution was sprayed, and the granules were sieved.
10) One part of the granules was submitted to a "curing" step. This part of the granules was transferred into a tray dryer and the granules were dried for at least 24 h with a temperature of about 6° C.

The in vitro release of lacosamide was measured according to USP (edition 24) method <711>, dissolution apparatus 2, in 900 mL of 0.1N HCl at 75 rpm and is given in the following table.

| Time [min] | Released total amount of active ingredient [%] | | |
|---|---|---|---|
| | Granules | Film-coated granules (uncured) | Film-coated granules (cured) |
| 5 | 42 | 3 | 1 |
| 10 | 87 | 7 | 3 |
| 15 | 98 | 13 | 5 |
| 20 | 99 | 20 | 7 |
| 25 | 100 | 25 | 9 |
| 30 | 100 | 31 | 11 |
| 45 | 100 | 43 | 16 |
| 60 | 99 | 53 | 20 |
| 90 | 99 | 66 | 28 |
| 120 | 99 | 75 | 34 |
| 150 | 99 | 81 | 40 |
| 180 | 99 | 84 | 44 |
| 240 | 98 | 88 | 50 |
| 300 | 98 | 90 | 55 |
| 360 | 98 | 91 | 59 |
| 480 | 98 | 93 | 64 |

Example 12

Granules with following composition were produced in the following way on a batch size of about 4 kg:

| Component | Quantity | Particle size[d] |
|---|---|---|
| a) Granules: | | $D_{10}$ = 106 µm |
| | | $D_{50}$ = 378 µm |
| | | $D_{90}$ = 826 µm |
| Lacosamide | 92.8 wt-% | |
| Kollicoat® SR 30 D from BASF company[a,b] | 6.5 wt-% | |
| Polyethylene glycol | 0.7 wt-% | |
| Water, purified[c] | q.s. | |
| b) Coating: | | |
| Kollicoat® SR 30 D from BASF company[a,b] | 90.0 wt-% | |
| Polyethylene glycol | 10.0 wt-% | |
| Water, purified[c] | q.s. | |
| c) Total (film coated granules): | | $D_{10}$ = 546 µm |
| | | $D_{50}$ = 849 µm |
| | | $D_{90}$ = n.a.[e] µm |
| Lacosamide | 71.9 wt-% | |
| Kollicoat® SR 30 D from BASF company[a,b] | 25.6 wt-% | |

-continued

| Component | Quantity | Particle size[d] |
|---|---|---|
| Polyethylene glycol | 2.5 wt-% | |
| Water, purified[c] | q.s. | |

[a]Kollicoat□ SR 30 D is an aqueous dispersion with a solid content of 30 wt-% consisting of polyvinylacetate (27 wt-%), polyvinylpyrrolidone (2.7 wt-%) and sodium lauryl sulfate (0.3 wt-%)
[b]Water is evaporated during process and is not present in final product, 25.6 wt-% in the final product corresponds to 84.3 wt-% of 30 wt-% Kollicoat□ SR 30 D dispersion
[c]Water is evaporated during process and is not present in final product, q.s. = quantum satis, as much as needed
[d]The particle size distribution was determined by a sieving test. The sieving test of the granules/powders was performed and analyzed according to 2.9.12 EP and 2.9.38 EP. $D_{10}$, $D_{50}$ and $D_{90}$, respectively, represent mass diameters correlating to 10%, 50% and 90%, respectively, of the mass of the investigated granules/powders
[e]n.a. = not applicable 1) The binder solution was prepared by adding purified water and propylene glycol to Kollicoat® SR 30 D dispersion under continuous stirring until the solid content of the binder solution was 20 wt-%. The mixture was homogenized by continuous stirring for 35 min.
2) Lacosamide was weighed, sieved, and transferred into a high-shear granulator.
3) The binder solution was added to Lacosamide under continuous stirring.
4) The mixture was granulated.
5) The wet granules were sieved and transferred into a tray dryer. The granules were dried for about 22 h with a temperature of about 45° C.
6) The dried granules were sieved, weighed and transferred to the fluid bed granulator.
7) The binder solution was prepared by adding purified water and propylene glycol to Kollicoat® SR 30 D dispersion under continuous stirring until the solid content of the binder solution was 20 wt-%. The mixture was homogenized by continuous stirring for 15 min.
8) The spray granulation was performed with inlet air temperature of ranging 53° C. to 75° C. The product temperature was kept between 28° C. to 40° C. and the spray rate ranging from 3.6 g/min to 15.6 g/min.
9) After the target amount of binder solution was sprayed, the granules were sieved, transferred into a tray dryer and dried The in vitro release of lacosamide was measured according to USP (edition 24) method <711>, dissolution apparatus 2, in 900 mL of 0.1N HCl at 75 rpm and is given in the following table.

| Time | Released total amount of active ingredient [%] | |
|---|---|---|
| [min] | Granules | Film-coated granules |
| 5 | 67 | 9 |
| 10 | 92 | 14 |
| 15 | 96 | 20 |
| 20 | 98 | 23 |
| 25 | 98 | 26 |
| 30 | 98 | 28 |
| 45 | 98 | 34 |
| 60 | 98 | 38 |
| 90 | 98 | 45 |
| 120 | 98 | 51 |
| 150 | 98 | 55 |
| 180 | 98 | 59 |
| 240 | 98 | 65 |
| 300 | 98 | 70 |
| 360 | 97 | 75 |
| 480 | 97 | 81 |

Example 13

Granules with following composition were produced in the following way on a batch size of about 4 kg:

| Component | Quantity | Particle size[d] |
|---|---|---|
| a) Granules: | | $D_{10}$ = 106 μm |
| | | $D_{50}$ = 378 μm |
| | | $D_{90}$ = 826 μm |
| Lacosamide | 92.8 wt-% | |
| Kollicoat□ SR 30 D from BASF company[a,b] | 6.5 wt-% | |
| Polyethylene glycol | 0.7 wt-% | |
| Water, purified[c] | q.s. | |
| b) Coating: | | |
| Kollicoat□ SR 30 D from BASF company[a,b] | 90.0 wt-% | |
| Polyethylene glycol | 10.0 wt-% | |
| Water, purified[c] | q.s. | |
| c) Total (film coated granules): | | $D_{10}$ = 560 μm |
| | | $D_{50}$ = 946 μm |
| | | $D_{90}$ = n.a.[e] μm |
| Lacosamide | 68.5 wt-% | |
| Kollicoat□ SR 30 D from BASF company[a,b] | 28.6 wt-% | |
| Polyethylene glycol | 2.9 wt-% | |
| Water, purified[c] | q.s. | |

[a]Kollicoat□ SR 30 D is an aqueous dispersion with a solid content of 30 wt-% consisting of polyvinylacetate (27 wt-%), polyvinylpyrrolidone (2.7 wt-%) and sodium lauryl sulfate (0.3 wt-%)
[b]Water is evaporated during process and is not present in final product, 28.6 wt-% in the final product corresponds to 95.3 wt-% of 30 wt-% Kollicoat□ SR 30 D dispersion
[c]Water is evaporated during process and is not present in final product, q.s. = quantum satis, as much as needed
[d]The particle size distribution was determined by a sieving test. The sieving test of the granules/powders was performed and analyzed according to 2.9.12 EP and 2.9.38 EP. $D_{10}$, $D_{50}$ and $D_{90}$, respectively, represent mass diameters correlating to 10%, 50% and 90%, respectively, of the mass of the investigated granules/powders
[e]n.a. = not applicable 1) Manufacturing process: as described for example 12 except for step 9
   Step 9: After the target amount of binder solution was sprayed, the granules were dried in a fluid bed granulator until a product temperature of 45° C. was achieved. The dried granules were sieved.

The in vitro release of lacosamide was measured according to USP (edition 24) method <711>, dissolution apparatus 2, in 900 mL of 0.1N HCl at 75 rpm and is given in the following table.

| Time | Released total amount of active ingredient [%] | |
|---|---|---|
| [min] | Granules | Film-coated granules |
| 5 | 67 | 11 |
| 10 | 92 | 17 |
| 15 | 96 | 21 |
| 20 | 98 | 24 |
| 25 | 98 | 26 |
| 30 | 98 | 28 |

-continued

| Time | Released total amount of active ingredient [%] | |
|---|---|---|
| [min] | Granules | Film-coated granules |
| 45 | 98 | 33 |
| 60 | 98 | 36 |
| 90 | 98 | 41 |
| 120 | 98 | 46 |
| 150 | 98 | 49 |
| 180 | 98 | 52 |
| 240 | 98 | 57 |
| 300 | 98 | 62 |
| 360 | 97 | 66 |
| 480 | 97 | 71 |

Matrix Tablets

Example 14

Matrix tablets with following composition per tablet were produced in the following way on a batch size of about 1.4 kg:

| Component | Quantity |
|---|---|
| Lacosamide | 200.0 mg |
| Polyethyleneglycol (Polyox WSR 301 from DOW company) | 40.0 mg |
| Cellulose, microcrystalline (type 102) | 56.0 mg |
| Hydroxypropylcellulose (low substituted) | 50.0 mg |
| Hydroxypropylcellulose | 4.0 mg |
| Silicified microcrystalline cellulose$^a$ | 125.2 mg |
| Magnesium stearate | 4.8 mg |
| Water, purified$^b$ | q.s. (200 mg) |
| | 480.0 mg |

$^a$Silicified microcrystalline cellulose contains 98% cellulose, microcrystalline and 2% silica, colloidal anhydrous
$^b$Water is evaporated during process and is not present in final product; q.s. = quantum satis, as much as needed 1) The binder solution was prepared by dissolving hydroxypropylcellulose in purified water.
2) Lacosamide, microcrystalline cellulose and low-substituted hydroxypropylcellulose were weighed, passed through a 2 mm sieve, transferred into a high-shear granulator and mixed
3) The binder solution was added to the dry mixture for about 1 minute under continuous stirring.
4) The mixture was granulated
5) The wet granules were transferred into a fluid bed dryer. The granules were dried with an inlet air temperature of about 70° C.±5° C. and a product temperature of NMT 50° C. until the loss on drying (LOD) was NMT 3.0%.
6) The dried granules were sieved
7) Silicified microcrystalline cellulose and polyethyleneglycol were screened.
8) The granules and the two ingredients from the previous step were blended.
9) Magnesium stearate was sieved together with a part of the blend from the previous step.
10) This pre-mixture was combined with the residual blend and finally blended
11) The finished final blend was compressed to tablets (oblong tooling—16.4 mm×7.6 mm).

The in vitro release of lacosamide was measured according to USP (edition 24) method <711>, dissolution apparatus 2, in 900 mL of 0.1N HCl at 75 rpm and is given in the following table.

| Time [min] | Released total amount of active ingredient [%] |
|---|---|
| 10 | 12 |
| 20 | 18 |
| 30 | 23 |
| 60 | 33 |
| 90 | 41 |
| 120 | 48 |
| 240 | 75 |
| 480 | 99 |

Example 15

Matrix tablets with following composition per tablet were produced in the following way on a batch size of about 1.4 kg:

| Component | Quantity |
|---|---|
| Lacosamide | 200.0 mg |
| Hydroxypropymethylcellulose (Methocel K4M from DOW company) | 20.0 mg |
| Hydroxypropymethylcellulose (Methocel K100M from DOW company) | 20.0 mg |
| Cellulose, microcrystalline (type 102) | 56.0 mg |
| Hydroxypropylcellulose (low substituted) | 50.0 mg |
| Hydroxypropylcellulose | 4.0 mg |
| Silicified microcrystalline cellulose$^a$ | 125.2 mg |
| Magnesium stearate | 4.8 mg |
| Water, purified$^b$ | q.s. (200 mg) |
| | 480.0 mg |

$^a$Silicified microcrystalline cellulose contains 98% cellulose, microcrystalline and 2% silica, colloidal anhydrous
$^b$Water is evaporated during process and is not present in final product; q.s. = quantum satis, as much as needed 1) Manufacturing process: as described for example 14 except for step 7
2) Step 7: Exchange of "polyethyleneglycol" against "hydroxypropymethylcellulose"

The in vitro release of lacosamide was measured according to USP (edition 24) method <711>, dissolution apparatus 2, in 900 mL of 0.1N HCl at 75 rpm and is given in the following table.

| Time [min] | Released total amount of active ingredient [%] |
|---|---|
| 10 | 20 |
| 20 | 31 |
| 30 | 37 |
| 60 | 49 |
| 90 | 56 |
| 120 | 62 |
| 240 | 75 |
| 480 | 91 |

Example 16

Matrix tablets with following composition per tablet were produced in the following way on a batch size of about 1.4 kg:

| Component | Quantity |
| --- | --- |
| Lacosamide | 200.0 mg |
| Hydroxypropymethylcellulose (Methocel K100M from DOW company) | 40.0 mg |
| Cellulose, microcrystalline (type 102) | 56.0 mg |
| Hydroxypropylcellulose (low substituted) | 50.0 mg |
| Hydroxypropylcellulose | 4.0 mg |
| Silicified microcrystalline cellulose[a] | 125.2 mg |
| Magnesium stearate | 4.8 mg |
| Water, purified[b] | q.s. (200 mg) |
| | 480.0 mg |

[a]Silicified microcrystalline cellulose contains 98% cellulose, microcrystalline and 2% silica, colloidal anhydrous
[b]Water is evaporated during process and is not present in final product; q.s. = quantum satis, as much as needed 1) Manufacturing process: as described for example 14 except for step 7
2) Step 7: Exchange of "polyethyleneglycol" against "hydroxypropymethylcellulose"

The in vitro release of lacosamide was measured according to USP (edition 24) method <711>, dissolution apparatus 2, in 900 mL of 0.1N HCl at 75 rpm and is given in the following table.

| Time [min] | Released total amount of active ingredient [%] |
| --- | --- |
| 10 | 18 |
| 20 | 27 |
| 30 | 32 |
| 60 | 41 |
| 90 | 48 |
| 120 | 54 |
| 240 | 68 |
| 480 | 87 |

Example 17

Matrix tablets with following composition per tablet were produced in the following way on a batch size of about 2 kg:

| Component | Quantity |
| --- | --- |
| Lacosamide | 300.0 mg |
| Hydroxypropymethylcellulose (Methocel K100M from DOW company) | 60.0 mg |
| Cellulose, microcrystalline (type 102) | 84.0 mg |
| Hydroxypropylcellulose (low substituted) | 75.0 mg |
| Hydroxypropylcellulose | 6.0 mg |
| Silicified microcrystalline cellulose[a] | 187.8 mg |
| Magnesium stearate | 7.2 mg |
| Water, purified[b] | q.s. (300 mg) |
| | 720.0 mg |

[a]Silicified microcrystalline cellulose contains 98% cellulose, microcrystalline and 2% silica, colloidal anhydrous
[b]Water is evaporated during process and is not present in final product; q.s. = quantum satis, as much as needed 1) Manufacturing process: as described for example 14 except for step 7 and 11
2) Step 7: Exchange of "polyethyleneglycol" against "hydroxypropymethylcellulose"
3) Step 11: Exchange of tooling: an oblong tooling with following dimensions was used 18.7 mm×8.7 mm The in vitro release of lacosamide was measured according to USP (edition 24) method <711>, dissolution apparatus 2, in 900 mL of 0.1N HCl at 75 rpm and is given in the following table.

| Time [min] | Released total amount of active ingredient [%] |
| --- | --- |
| 10 | 16 |
| 20 | 22 |
| 30 | 25 |
| 60 | 33 |
| 90 | 39 |
| 120 | 43 |
| 240 | 57 |
| 480 | 74 |

Example 18

Matrix tablets with following composition per tablet were produced in the following way on a batch size of about 1 kg:

| Component | Quantity |
| --- | --- |
| Lacosamide | 200.0 mg |
| Polyethyleneglycol (Polyox WSR 301 from DOW company) | 60.0 mg |
| Cellulose, microcrystalline (type 102) | 56.0 mg |
| Hydroxypropylcellulose (low substituted) | 50.0 mg |
| Hydroxypropylcellulose | 4.0 mg |
| Silicified microcrystalline cellulose[a] | 125.2 mg |
| Magnesium stearate | 4.8 mg |
| Water, purified[b] | q.s. (200 mg) |
| | 500.0 mg |

[a]Silicified microcrystalline cellulose contains 98% cellulose, microcrystalline and 2% silica, colloidal anhydrous
[b]Water is evaporated during process and is not present in final product; q.s. = quantum satis, as much as needed Manufacturing process: see example 14

The in vitro release of lacosamide was measured according to USP (edition 24) method <711>, dissolution apparatus 2, in 900 mL of 0.1N HCl at 75 rpm and is given in the following table.

| Time [min] | Released total amount of active ingredient [%] |
| --- | --- |
| 10 | 8 |
| 20 | 13 |
| 30 | 17 |
| 60 | 25 |
| 90 | 32 |
| 120 | 38 |
| 240 | 57 |
| 480 | 89 |

Example 19

Formulation a of Human PK Study of Example 2

Matrix tablets with following composition per tablet were produced in the following way on a batch size of about 2 kg:

| Component | Quantity |
|---|---|
| Lacosamide | 200.0 mg |
| Hydroxypropymethylcellulose (Methocel K15M CR from DOW company) | 50.0 mg |
| Cellulose, microcrystalline (type 102) | 56.0 mg |
| Hydroxypropylcellulose (low substituted) | 50.0 mg |
| Hydroxypropylcellulose | 4.0 mg |
| Silicified microcrystalline cellulose[a] | 135.0 mg |
| Magnesium stearate | 5.0 mg |
| Water, purified[b] | q.s. (200 mg) |
| | 500.0 mg |

[a]Silicified microcrystalline cellulose contains 98% cellulose, microcrystalline and 2% silica, colloidal anhydrous
[b]Water is evaporated during process and is not present in final product; q.s. = quantum satis, as much as needed 1) The clear binder solution was prepared by dissolving hydroxypropylcellulose in purified water.
2) Lacosamide, microcrystalline cellulose and low-substituted hydroxypropylcellulose were sieved, transferred into a high-shear granulator and mixed for about 5 minutes
3) The binder solution was added to the dry mixture under continuous stirring
4) The mixture was granulated
5) The wet granules were sieved and transferred into a fluid bed dryer. The granules were dried with an inlet air temperature of about 70° C.±5° C. and a product temperature of NMT 52° C. until the loss on drying (LOD) was NMT 3.0%.
6) The dried granules were sieved, weighed and transferred to a planetary mixer.
7) Silicified microcrystalline cellulose and hydroxypymethylcellulose were screened.
8) The granules and the two ingredients from the previous step were blended.
9) Magnesium stearate was sieved together with a part of the blend from the previous step.
10) This pre-mixture was combined with the residual blend and finally blended
11) The finished final blend was compressed to tablets (oblong tooling—15.2 mm×8.6 mm).

The in vitro release of lacosamide was measured according to USP (edition 24) method <711>, dissolution apparatus 2, in 900 mL of 0.1N HCl at 50 rpm or 75 rpm and is given in the following table.

| Time | Released total amount of active ingredient [%] | |
|---|---|---|
| [min] | 50 rpm[a] | 75 rpm[a] |
| 15 | 11 | 22 |
| 30 | — | 29 |
| 45 | 21 | 34 |
| 60 | 25 | 38 |
| 120 | 36 | 49 |
| 240 | 51 | 65 |
| 480 | 71 | 85 |
| 600 | — | 91 |
| 720 | 84 | 96 |

[a]Paddle speed during dissolution testing, for IV/IV correlation data at 50 rpm was used

Example 20

Formulation B of Human PK Study of Example 2

Matrix tablets with following composition per tablet were produced in the following way on a batch size of about 2 kg:

| Component | Quantity |
|---|---|
| Lacosamide | 200.0 mg |
| Hydroxypropymethylcellulose (Methocel K15M CR from DOW company) | 100.0 mg |
| Cellulose, microcrystalline (type 102) | 56.0 mg |
| Hydroxypropylcellulose (low substituted) | 50.0 mg |
| Hydroxypropylcellulose | 4.0 mg |
| Silicified microcrystalline cellulose[a] | 85.0 mg |
| Magnesium stearate | 5.0 mg |
| Water, purified[b] | q.s. (200 mg) |
| | 500.0 mg |

[a]Silicified microcrystalline cellulose contains 98% cellulose, microcrystalline and 2% silica, colloidal anhydrous
[b]Water is evaporated during process and is not present in final product; q.s. = quantum satis, as much as needed Manufacturing process: see example 19

The in vitro release of lacosamide was measured according to USP (edition 24) method <711>, dissolution apparatus 2, in 900 mL of 0.1N HCl at 50 rpm or 75 rpm and is given in the following table.

| Time | Released total amount of active ingredient [%] | |
|---|---|---|
| [min] | 50 rpm[a] | 75 rpm[a] |
| 15 | 6 | 9 |
| 30 | — | 13 |
| 45 | 12 | 17 |
| 60 | 15 | 21 |
| 120 | 24 | 31 |
| 240 | 38 | 47 |
| 480 | 58 | 69 |
| 600 | — | 78 |
| 720 | 74 | 85 |

[a]Paddle speed during dissolution testing, for IV/IV correlation data at 50 rpm was used

Example 21

Matrix tablets with following composition per tablet were produced in the following way on a batch size of about 2 kg:

| Component | Quantity |
|---|---|
| Lacosamide | 200.0 mg |
| Hydroxypropymethylcellulose (Methocel K15M CR from DOW company) | 75.0 mg |
| Cellulose, microcrystalline (type 102) | 56.0 mg |
| Hydroxypropylcellulose (low substituted) | 50.0 mg |
| Hydroxypropylcellulose | 4.0 mg |
| Silicified microcrystalline cellulose[a] | 110.0 mg |
| Magnesium stearate | 5.0 mg |
| Water, purified[b] | q.s. (200 mg) |
| | 500.0 mg |

[a]Silicified microcrystalline cellulose contains 98% cellulose, microcrystalline and 2% silica, colloidal anhydrous
[b]Water is evaporated during process and is not present in final product; q.s. = quantum satis, as much as needed Manufacturing process: see example 19

The in vitro release of lacosamide was measured according to USP (edition 24) method <711>, dissolution apparatus 2, in 900 mL of 0.1N HCl at 75 rpm and is given in the following table.

| Time [min] | Released total amount of active ingredient [%] |
|---|---|
| 15 | 11 |
| 30 | 16 |
| 45 | 21 |
| 60 | 24 |
| 120 | 35 |
| 240 | 51 |
| 480 | 74 |
| 600 | 82 |
| 720 | 89 |

Example 22

Matrix tablets with following composition per tablet were produced in the following way on a batch size of about 2 kg:

| Component | Quantity |
|---|---|
| Lacosamide | 200.0 mg |
| Hydroxypropymethylcellulose (Methocel K4M CR from DOW company) | 100.0 mg |
| Cellulose, microcrystalline (type 102) | 56.0 mg |
| Hydroxypropylcellulose (low substituted) | 50.0 mg |
| Hydroxypropylcellulose | 4.0 mg |
| Silicified microcrystalline cellulose[a] | 85.0 mg |
| Magnesium stearate | 5.0 mg |
| Water, purified[b] | q.s. |
| | (200 mg) |
| | 500.0 mg |

[a]Silicified microcrystalline cellulose contains 98% cellulose, microcrystalline and 2% silica, colloidal anhydrous
[b]Water is evaporated during process and is not present in final product; q.s. = quantum satis, as much as needed Manufacturing process: see example 19

The in vitro release of lacosamide was measured according to USP (edition 32) method <711>, dissolution apparatus 2, in 900 mL of 0.1N HCl at 75 rpm and is given in the following table.

| Time [min] | Released total amount of active ingredient [%] |
|---|---|
| 15 | 11 |
| 45 | 19 |
| 60 | 22 |
| 120 | 33 |
| 240 | 48 |
| 480 | 69 |
| 720 | 83 |
| 900 | 91 |

Example 23

Matrix tablets with following composition per tablet were produced in the following way on a batch size of about 2 kg:

| Component | Quantity |
|---|---|
| Lacosamide | 200.0 mg |
| Hydroxypropymethylcellulose (Methocel K100M CR from DOW company) | 100.0 mg |
| Cellulose, microcrystalline (type 102) | 56.0 mg |
| Hydroxypropylcellulose (low substituted) | 50.0 mg |
| Hydroxypropylcellulose | 4.0 mg |
| Silicified microcrystalline cellulose[a] | 85.0 mg |
| Magnesium stearate | 5.0 mg |
| Water, purified[b] | q.s. |
| | (200 mg) |
| | 500.0 mg |

[a]Silicified microcrystalline cellulose contains 98% cellulose, microcrystalline and 2% silica, colloidal anhydrous
[b]Water is evaporated during process and is not present in final product; q.s. = quantum satis, as much as needed Manufacturing process: see example 19

The in vitro release of lacosamide was measured according to USP (edition 24) method <711>, dissolution apparatus 2, in 900 mL of 0.1N HCl at 75 rpm and is given in the following table.

| Time [min] | Released total amount of active ingredient [%] |
|---|---|
| 15 | 9 |
| 45 | 17 |
| 60 | 20 |
| 120 | 29 |
| 240 | 43 |
| 480 | 62 |
| 720 | 76 |
| 900 | 85 |

Example 24

Matrix tablets with following composition per tablet were produced in the following way on a batch size of about 2 kg:

| Component | Quantity |
|---|---|
| Lacosamide | 200.0 mg |
| Hydroxypropymethylcellulose (Methocel K100M DC from DOW company) | 100.0 mg |
| Cellulose, microcrystalline (type 102) | 56.0 mg |
| Hydroxypropylcellulose (low substituted) | 50.0 mg |
| Hydroxypropylcellulose | 4.0 mg |
| Silicified microcrystalline cellulose[a] | 85.0 mg |
| Magnesium stearate | 5.0 mg |
| Water, purified[b] | q.s. |
| | (200 mg) |
| | 500.0 mg |

[a]Silicified microcrystalline cellulose contains 98% cellulose, microcrystalline and 2% silica, colloidal anhydrous
[b]Water is evaporated during process and is not present in final product; q.s. = quantum satis, as much as needed Manufacturing process: see example 19

The in vitro release of lacosamide was measured according to USP (edition 24) method <711>, dissolution apparatus 2, in 900 mL of 0.1N HCl at 75 rpm and is given in the following table.

| Time [min] | Released total amount of active ingredient [%] |
|---|---|
| 15 | 13 |
| 45 | 21 |
| 60 | 25 |
| 120 | 34 |
| 240 | 47 |
| 480 | 65 |
| 720 | 78 |
| 900 | 86 |

Example 25

Matrix tablets with following composition per tablet were produced in the following way on a batch size of about 40 g:

| Component | Quantity |
|---|---|
| Lacosamide | 156.4 mg |
| Surelease® E-7-19030 from Colorcon company[a, b] | 12.2 mg |
| Magnesium stearate | 1.4 mg |
| Water, purified[c] | q.s. (32.5 mg) |
| | 170.0 mg |

[a]Surelease® E-7-19030 is an aqueous dispersion with a solid content of 25 wt-% consisting of ethylcellulose, dibutyl sebacat, oleic acid, ammonium hydroxide and colloidal anhydrous silica
[b]Water is evaporated during process and is not present in final product, 12.2 mg corresponds to 48.8 mg 25 wt-% Surelease® E-7-19030 dispersion
[c]Water is evaporated during process and is not present in final product, q.s. = quantum satis, as much as needed 1) The binder solution was prepared by diluting Surelease® dispersion with purified water to concentration of 15 wt-%.
2) Lacosamide was sieved and transferred into a high-shear granulator.
3) The binder solution was added to Lacosamide
4) The mixture was granulated.
5) The wet granules were sieved and transferred into a tray dryer. The granules were dried and sieved
6) The granule and sieved magnesium stearate were blended
7) The finished final blend was compressed to tablets (oblong tooling—10.4 mm×5.6 mm).

The in vitro release of lacosamide was measured according to USP (edition 24) method <711>, dissolution apparatus 2, in 900 mL of 0.1N HCl at 75 rpm and is given in the following table.

| Time [min] | Released total amount of active ingredient [%] |
|---|---|
| 5 | 8 |
| 10 | 14 |
| 15 | 19 |
| 20 | 23 |
| 25 | 26 |
| 30 | 29 |
| 45 | 37 |
| 60 | 44 |
| 90 | 55 |
| 120 | 64 |
| 150 | 72 |
| 180 | 78 |
| 240 | 88 |
| 300 | 97 |

-continued

| Time [min] | Released total amount of active ingredient [%] |
|---|---|
| 360 | 101 |
| 480 | 103 |

Example 26

Matrix tablets with following composition per tablet were produced in the following way on a batch size of about 50 g:

| Component | Quantity |
|---|---|
| Lacosamide | 150.7 mg |
| Surelease® E-7-19030 from Colorcon company[a, b] | 19.6 mg |
| Magnesium stearate | 1.7 mg |
| | 172.0 mg |

[a]Surelease® E-7-19030 is an aqueous dispersion with a solid content of 25 wt-% consisting of ethylcellulose, dibutyl sebacat, oleic acid, ammonium hydroxide and colloidal anhydrous silica
[b]Water is evaporated during process and is not present in final product, 19.6 mg corresponds to 78.4 mg 25 wt-% Surelease® E-7-19030 dispersion 1) The binder solution was prepared by homogenization of 25 wt-% Surelease® dispersion.
2) Lacosamide was sieved and transferred into a high-shear granulator
3) The binder solution was added to Lacosamide under continuous stirring
4) The mixture was granulated
5) The wet granules were sieved and transferred into a tray dryer. The granules were dried and sieved
6) The granule and sieved magnesium stearate were blended
7) The finished final blend was compressed to tablets (oblong tooling—10.4 mm×5.6 mm).

The in vitro release of lacosamide was measured according to USP (edition 24) method <711>, dissolution apparatus 2, in 900 mL of 0.1N HCl at 75 rpm and is given in the following table.

| Time [min] | Released total amount of active ingredient [%] |
|---|---|
| 5 | 8 |
| 10 | 14 |
| 15 | 18 |
| 20 | 22 |
| 25 | 25 |
| 30 | 28 |
| 45 | 34 |
| 60 | 40 |
| 90 | 50 |
| 120 | 57 |
| 150 | 64 |
| 180 | 70 |
| 240 | 80 |
| 300 | 87 |
| 360 | 93 |
| 480 | 100 |

Example 27

Matrix tablets with following composition per tablet were produced in the following way on a batch size of about 10 g:

| Component | Quantity |
| --- | --- |
| Lacosamide | 133.6 mg |
| Surelease® E-7-19030 from Colorcon company[a, b] | 35.7 mg |
| Magnesium stearate | 1.7 mg |
| Water, purified[c] | q.s. (95.2 mg) |
| | 171.0 mg |

[a]Surelease® E-7-19030 is an aqueous dispersion with a solid content of 25 wt-% consisting of ethylcellulose, dibutyl sebacat, oleic acid, ammonium hydroxide and colloidal anhydrous silica
[b]Water is evaporated during process and is not present in final product, 35.7 mg corresponds to 142.8 mg 25 wt-% Surelease® E-7-19030 dispersion
[c]Water is evaporated during process and is not present in final product, q.s. = quantum satis, as much as needed 1) The binder solution was prepared by diluting Surelease® dispersion with purified water to concentration of 15 wt-%.
2) Lacosamide was sieved and transferred into a high-shear granulator.
3) The binder solution was added to Lacosamide under continuous stirring
4) The mixture was granulated
5) The wet granules were sieved and transferred into a tray dryer. The granules were dried for about 16 h with a temperature of about 45° C.
6) The dried granules were sieved
7) The granule and sieved magnesium stearate were blended in a mixing container
8) The finished final blend was compressed to tablets (oblong tooling—10.4 mm×5.6 mm, convex radius 5.0 mm).

The in vitro release of lacosamide was measured according to USP (edition 24) method <711>, dissolution apparatus 2, in 900 mL of 0.1N HCl at 75 rpm and is given in the following table.

| Time [min] | Released total amount of active ingredient [%] |
| --- | --- |
| 5 | 7 |
| 10 | 11 |
| 15 | 14 |
| 20 | 17 |
| 25 | 19 |
| 30 | 22 |
| 45 | 27 |
| 60 | 32 |
| 90 | 40 |
| 120 | 47 |
| 150 | 54 |
| 180 | 59 |
| 240 | 68 |
| 300 | 75 |
| 360 | 81 |
| 480 | 90 |

Example 28

Matrix tablets with following composition per tablet were produced in the following way on a batch size of about 40 g:

| Component | Quantity |
| --- | --- |
| Lacosamide | 100.6 mg |
| Surelease® E-7-19030 from Colorcon company[a, b] | 13.6 mg |
| MicroceLac® 100[c] | 57.6 mg |
| Magnesium stearate | 1.7 mg |
| | 173.5 mg |

[a]Surelease® E-7-19030 is an aqueous dispersion with a solid content of 25 wt-% consisting of ethylcellulose, dibutyl sebacat, oleic acid, ammonium hydroxide and colloidal anhydrous silica
[b]Water is evaporated during process and is not present in final product, 13.6 mg corresponds to 54.4 mg 25 wt-% Surelease® E-7-19030 dispersion
[c]MicroceLac® 100 is a spray dried mixture of 75 wt-% lactose monohydrate and 25 wt-% microcrystalline cellulose from Meggle company 1) Steps 1-5 analog to example 27
   i. MicroceLac® 100 was sieved (1 mm) and transferred to the mixing container.
   ii. The granules and MicroceLac® 100 were blended in a mixing container
   iii. The granules, MicroceLac® 100 and sieved magnesium stearate were blended in a mixing container
   iv. The finished final blend was compressed to tablets (oblong tooling—10.4 mm×5.6 mm).

The in vitro release of lacosamide was measured according to USP (edition 24) method <711>, dissolution apparatus 2, in 900 mL of 0.1N HCl at 75 rpm and is given in the following table.

| Time [min] | Released total amount of active ingredient [%] |
| --- | --- |
| 5 | 8 |
| 10 | 13 |
| 15 | 17 |
| 20 | 20 |
| 25 | 23 |
| 30 | 26 |
| 45 | 33 |
| 60 | 39 |
| 90 | 50 |
| 120 | 59 |
| 150 | 67 |
| 180 | 73 |
| 240 | 82 |
| 300 | 90 |
| 360 | 95 |
| 480 | 99 |

Example 29

Matrix tablets with following composition per tablet were produced in the following way on a batch size of about 10 g:

| Component | Quantity |
| --- | --- |
| Lacosamide | 138.0 mg |
| Kollicoat® SR 30 D from BASF company[a, b] | 27.5 mg |
| Propylene glycol | 2.8 mg |
| Magnesium stearate | 1.7 mg |
| | 170.0 mg |

[a]Kollicoat® SR 30 D is an aqueous dispersion with a solid content of 30 wt-% consisting of polyvinylacetate (27 wt-%), polyvinylpyrrolidone (2.7 wt-%) and sodium lauryl sulfate (0.3 wt-%)
[b]Water is evaporated during process and is not present in final product, 27.5 mg corresponds to 91.7 mg 30 wt-% Kollicoat® SR 30 D dispersion 1) Example 29 was prepared analogues to Example 27

The in vitro release of lacosamide was measured according to USP (edition 24) method <711>, dissolution apparatus 2, in 900 mL of 0.1N HCl at 75 rpm and is given in the following table.

| Time [min] | Released total amount of active ingredient [%] |
| --- | --- |
| 5 | 5 |
| 10 | 9 |
| 15 | 12 |
| 20 | 14 |
| 25 | 16 |
| 30 | 18 |
| 45 | 22 |
| 60 | 26 |
| 90 | 31 |
| 120 | 36 |
| 150 | 40 |
| 180 | 44 |
| 240 | 49 |
| 300 | 54 |
| 360 | 59 |
| 480 | 66 |

Example 30

Matrix tablets with following composition per tablet were produced in the following way on a batch size of about 40 g:

| Component | Quantity |
| --- | --- |
| Lacosamide | 98.8 mg |
| Kollicoat® SR30 D from BASF company[a, b] | 19.7 mg |
| Propylene glycol | 2.0 mg |
| MicroceLac® 100[c] | 47.7 mg |
| Magnesium stearate | 1.7 mg |
|  | 169.9 mg |

[a]Kollicoat® SR 30 D is an aqueous dispersion with a solid content of 30 wt-% consisting of polyvinylacetate (27 wt-%), polyvinylpyrrolidone (2.7 wt-%) and sodium lauryl sulfate (0.3 wt-%)
[b]Water is evaporated during process and is not present in final product, 19.7 mg corresponds to 65.7 mg 30 wt-% Kollicoat® SR 30 D dispersion
[c]MicroceLac® 100 is a spray dried mixture of 75 wt-% lactose monohydrate and 25 wt-% microcrystalline cellulose from Meggle company 1) The binder solution was prepared by adding propylene glycol to Kollicoat® SR 30 D dispersion under continuous stirring, the mixture was homogenized by continuous stirring for 15 min.
2) Lacosamide was sieved and transferred into a high-shear granulator.
3) The binder solution was added to Lacosamide under continuous stirring
4) The mixture was granulated for 1-2 min at a speed of 500 rpm plus chopper set to 2000 rpm.
5) The wet granules were sieved and transferred into a tray dryer. The granules were dried for about 18 h with a temperature of about 40° C.
6) The dried granules were sieved and transferred to a mixing container.
7) The granules, sieved MicroceLac® 100 and sieved magnesium stearate were blended in a mixing container.
8) The finished final blend was compressed to tablets (oblong tooling—10.4 mm×5.6 mm).

The in vitro release of lacosamide was measured according to USP (edition 24) method <711>, dissolution apparatus 2, in 900 mL of 0.1N HCl at 75 rpm and is given in the following table.

| Time [min] | Released total amount of active ingredient [%] |
| --- | --- |
| 5 | 6 |
| 10 | 10 |
| 15 | 13 |
| 20 | 16 |
| 25 | 19 |
| 30 | 21 |
| 45 | 26 |
| 60 | 31 |
| 90 | 39 |
| 120 | 47 |
| 150 | 54 |
| 180 | 61 |
| 240 | 71 |
| 300 | 79 |
| 360 | 85 |
| 480 | 95 |

Example 31

Matrix tablets with following composition per tablet were produced in the following way on a batch size of about 10 g:

| Component | Quantity |
| --- | --- |
| Lacosamide | 140.4 mg |
| Eudragit® RS 30 D from EVONIK Röhm GmbH company[a, b] | 24.9 mg |
| Triethylcitrate | 5.0 mg |
| Magnesium stearate | 1.7 mg |
|  | 172.0 mg |

[a]Eudragit® RS 30 D is an aqueous dispersion with a solid content of 30.35 wt-% consisting of ammonio methacrylate copolymer, type B (30.0 wt-%), sorbic acid (0.25 wt-%) and sodium hydroxide (0.1 wt-%)
[b]Water is evaporated during process and is not present in final product, 35.7 mg corresponds to 82.0 mg 30.35 wt-% Eudragit® RS 30 D dispersion 1) The binder solution was prepared by adding triethylcitrate to Eudragit® RS 30 D dispersion under continuous stirring, the mixture was homogenized by continuous stirring for 15 min.
2) Steps 2 to 7 are analoguous to example 27
3) The finished final blend was transferred to a tablet press (Kilian RLS 12) and compressed to tablets (oblong tooling—10.4 mm×5.6 mm).

The in vitro release of lacosamide was measured according to USP (edition 24) method <711>, dissolution apparatus 2, in 900 mL of 0.1N HCl at 75 rpm and is given in the following table.

| Time [min] | Released total amount of active ingredient [%] |
| --- | --- |
| 5 | 7 |
| 10 | 11 |
| 15 | 14 |
| 20 | 16 |
| 25 | 18 |
| 30 | 20 |
| 45 | 25 |
| 60 | 29 |
| 90 | 36 |

-continued

| Time [min] | Released total amount of active ingredient [%] |
|---|---|
| 120 | 41 |
| 150 | 45 |
| 180 | 49 |
| 240 | 56 |
| 300 | 61 |
| 360 | 67 |
| 480 | 74 |

Example 32

Matrix tablets with following composition per tablet were produced in the following way on a batch size of about 40 g:

| Component | Quantity |
|---|---|
| Lacosamide | 100.3 mg |
| Eudragit® RS 30 D from EVONIK Rohm GmbH company[a, b] | 17.8 mg |
| Triethylcitrate | 3.6 mg |
| MicroceLac® 100[c] | 48.7 mg |
| Magnesium stearate | 1.7 mg |
| | 172.1 mg |

[a]Eudragit® RS 30 D is an aqueous dispersion with a solid content of 30.35 wt-% consisting of ammonio methacrylate copolymer, type B (30.0 wt-%), sorbic acid (0.25 wt-%) and sodium hydroxide (0.1 wt-%)
[b]Water is evaporated during process and is not present in final product, 17.8 mg corresponds to 58.6 mg 30.35 wt-% Eudragit® RS 30 D dispersion
[c]MicroceLac® 100 is a spray dried mixture of 75 wt-% lactose monohydrate and 25 wt-% microcrystalline cellulose from Meggle company 1) The binder solution was prepared by adding triethylcitrate to Eudragit® RS 30 D dispersion under continuous stirring
2) Steps 2-8 were analoguous to example 30

The in vitro release of lacosamide was measured according to USP (edition 24) method <711>, dissolution apparatus 2, in 900 mL of 0.1N HCl at 75 rpm and is given in the following table.

| Time [min] | Released total amount of active ingredient [%] |
|---|---|
| 5 | 6 |
| 10 | 11 |
| 15 | 14 |
| 20 | 17 |
| 25 | 20 |
| 30 | 22 |
| 45 | 28 |
| 60 | 34 |
| 90 | 43 |
| 120 | 51 |
| 150 | 58 |
| 180 | 63 |
| 240 | 72 |
| 300 | 78 |
| 360 | 84 |
| 480 | 91 |

Example 33 (Xanthan—2.5%)

Matrix tablets with following composition per tablet were produced in the following way on a batch size of about 1 kg:

| Component | Quantity |
|---|---|
| Lacosamide | 743.8 mg |
| Xanthan gum (Xanthan Gummi from C.E. Roeper GmbH company) | 21.3 mg |
| Cellulose, microcrystalline (type 102) | 76.5 mg |
| Silica, colloidal anhydrous | 4.2 mg |
| Magnesium stearate | 4.2 mg |
| | 850.0 mg |

1) Before processing lacosamide was deagglomerated in a centrifugal mill with a ring sieve size of 2 mm and a rotational speed of 6000 rpm.
2) Lacosamide, microcrystalline cellulose and xanthan gum were transferred into laboratory scale blender and mixed at 27+/−2 rpm for 20 min.
3) Magnesium stearate was added to the blend from the previous step.
4) The mixing process was continued at 9+/−2 rpm for 3 min.
5) The powdered blends were compacted in a roller compactor equipped with two smooth rolls. The gap between the rolls was kept constant at 3 mm. Rim rolls were used as sealing system. Roll speed was set on 1 rpm and a specific compaction force of 9 kN/cm was applied. The obtained ribbons were directly granulated with a star granulator using a 1 mm sieve.
6) The roll compacted granules were transferred to a tablet press (IMA Pressima) and compressed to tablets (oblong tooling—19.0 mm×9.0 mm).

The in vitro release of lacosamide was measured according to USP (edition 24) method <711>, dissolution apparatus 2, in 900 mL of 0.1N HCl at 75 rpm and is given in the following table.

| Time [min] | Released total amount of active ingredient [%] |
|---|---|
| 12 | 6 |
| 24 | 10 |
| 36 | 14 |
| 48 | 18 |
| 60 | 22 |
| 96 | 33 |
| 120 | 40 |
| 180 | 55 |
| 240 | 69 |
| 300 | 81 |
| 360 | 88 |
| 420 | 95 |
| 480 | 98 |
| 540 | 99 |
| 600 | 98 |
| 660 | 99 |
| 720 | 100 |

Example 34

Xanthan—5%

Matrix tablets with following composition per tablet were produced in the following way on a batch size of about 1 kg:

| Component | Quantity [mg] | | |
|---|---|---|---|
| | 425 mg vs. 500 mg | 722.6 mg vs. 850 mg | 850 mg vs. 1000 mg |
| Lacosamide | 425.0 | 722.6 | 850.0 |
| Xanthan (Xanthan Gummi from C.E. Roeper GmbH company) | 25.0 | 42.5 | 50.0 |
| Cellulose, microcrystalline (type 102) | 45.0 | 76.5 | 90.0 |
| Silica, colloidal anhydrous | 2.5 | 4.2 | 5.0 |
| Magnesium stearate | 2.5 | 4.2 | 5.0 |
| | 500.0 | 850.0 | 1000.0 |

1) Manufacturing process: see example 33 except for step 6
2) Step 6: Following toolings were used for tablet manufacturing:
   500 mg tablets: a) round tooling: —13.0 mm and
     b) oblong tooling—16.0 mm×7.5 mm
   850 mg tablets: oblong tooling—19.0 mm×9.0 mm
   1000 mg tablets: oblong tooling—19.0 mm×10.2 mm The in vitro release of lacosamide was measured according to USP (edition 24) method <711>, dissolution apparatus 2, in 900 mL of 0.1N HCl at 75 rpm and is given in the following table.

| Time [min] | Released total amount of active ingredient [%] | | | |
|---|---|---|---|---|
| | 425 mg vs. 500 mg | | 722.6 mg vs. 850 mg | 850 mg vs. 1000 mg |
| | (round) | (oblong) | (oblong) | (oblong) |
| 12 | 4 | 3 | 4 | 3 |
| 24 | 7 | 7 | 7 | 6 |
| 36 | 10 | 10 | 9 | 8 |
| 48 | 13 | 13 | 12 | 10 |
| 60 | 14 | 16 | 14 | 11 |
| 96 | 21 | 22 | 20 | 16 |
| 120 | 25 | 26 | 24 | 18 |
| 180 | 35 | 38 | 33 | 26 |
| 240 | 45 | 50 | 42 | 33 |
| 300 | 54 | 59 | 51 | 40 |
| 360 | 62 | 69 | 59 | 48 |
| 420 | 70 | 77 | 66 | 54 |
| 480 | 76 | 85 | 73 | 61 |
| 540 | 83 | 92 | 79 | 68 |
| 600 | 89 | 96 | 85 | 73 |
| 660 | 95 | 99 | 90 | 79 |
| 720 | 98 | 101 | 95 | 84 |

Example 35 Xanthan—10%

Matrix tablets with following composition per tablet were produced in the following way on a batch size of about 1 kg:

| Component | Quantity [mg] | | | |
|---|---|---|---|---|
| | 52 mg vs. 65 mg | 400 mg vs. 500 mg | 680.1 mg vs. 850 mg | 800 mg vs. 1000 mg |
| Lacosamide | 52.0 | 400.0 | 680.1 | 800.0 |
| Xanthan (Xanthan Gummi from C.E. Roeper GmbH company) | 6.5 | 50.0 | 85.0 | 100.0 |
| Cellulose, microcrystalline (type 102) | 5.9 | 45.0 | 76.5 | 90.0 |
| Silica, colloidal anhydrous | 0.3 | 2.5 | 4.2 | 5.0 |
| Magnesium stearate | 0.3 | 2.5 | 4.2 | 5.0 |
| | 65.0 | 500.0 | 850.0 | 1000.0 |

1) Manufacturing process: see example 33 except for step 6
2) Step 6: Following toolings were used for tablet manufacturing:
   65 mg tablets: round tooling—□5.0 mm
   500 mg tablets: a) round tooling: □13.0 mm and
     b) oblong tooling—16.0 mm×7.5 mm
   850 mg tablets: oblong tooling—19.0 mm×9.0 mm
   1000 mg tablets: oblong tooling—19.0 mm×10.2 mm The in vitro release of lacosamide was measured according to USP (edition 24) method <711>, dissolution apparatus 2, in 900 mL of 0.1N HCl at 75 rpm and is given in the following table.

| Time [min] | Released total amount of active ingredient [%] | | | |
|---|---|---|---|---|
| | 52 mg vs. 65 mg | 400 mg vs. 500 mg | 680.1 mg vs. 850 mg | 800 mg vs. 1000 mg |
| | (round) | (round) | (oblong) | (oblong) |
| 12 | 18 | 2 | 3 | 2 |
| 24 | 31 | 5 | 5 | 5 |
| 36 | 42 | 7 | 8 | 7 | 6 |
| 48 | 48 | 9 | 10 | 9 | 8 |
| 60 | 54 | 11 | 12 | 10 | 9 |
| 96 | 70 | 16 | 17 | 13 | 12 |
| 120 | 77 | 19 | 20 | 16 | 15 |
| 180 | 90 | 26 | 27 | 21 | 19 |
| 240 | 96 | 33 | 33 | 25 | 23 |
| 300 | 99 | 38 | 39 | 29 | 27 |
| 360 | 100 | 44 | 45 | 34 | 30 |
| 420 | 99 | 50 | 49 | 37 | 34 |
| 480 | 99 | 55 | 54 | 41 | 37 |
| 540 | 99 | 62 | 60 | 44 | 40 |
| 600 | 100 | 66 | 65 | 48 | 43 |
| 660 | 100 | 71 | 71 | 51 | 46 |
| 720 | 101 | 75 | 75 | 54 | 48 |

Example 36

Matrix Tablet Based on IR Granules

Matrix tablets with following composition per tablet were produced in the following way on a batch size of about 2 kg:

| Component | Quantity |
|---|---|
| Tablet core: | |
| Lacosamide | 300.0 mg |
| Hydroxypropylmethylcellulose (Methocel ® K15M CR from Dow company) | 75.0 mg |

-continued

| | |
|---|---|
| Cellulose, microcrystalline (type 102) | 84.0 mg |
| Hydroxypropylcellulose (low substituted) | 75.0 mg |
| Hydroxypropylcellulose | 6.0 mg |
| Silicified microcrystalline cellulose[a] | 202.5 mg |
| Magnesium stearate | 7.5 mg |
| Water, purified[b] | q.s. |
| | 750.0 mg |

| | Film coating: | | |
|---|---|---|---|
| | 2% | 3% | 5% |
| Opadry ® Y-1-7000 white[c] | 15.0 mg | 22.5 mg | 37.5 mg |
| Water, purified[b] | | | q.s. |
| Total (film coated tablet) | 765.0 mg | 772.5 mg | 787.5 mg |

[a]Silicified microcrystalline cellulose contains 98% cellulose, microcrystalline and 2% silica, colloidal anhydrous
[b]Water is evaporated during process and is not present in final product; q.s. = quantum satis, as much as needed
[c]Opadry Y-1-700 white is a non-functional coating system based on hydroxypropymethylcellulose from Colorcon company 1) The binder solution was prepared by dissolving hydroxypropylcellulose in purified water.
2) Lacosamide, microcrystalline cellulose and low-substituted hydroxypropylcellulose were transferred into a high-shear granulator and mixed.
3) The binder solution was added to the dry mixture over under continuous stirring
4) The mixture was granulated.
5) The wet granulate was sieved and transferred into a fluid bed dryer. The granulate was dried with an inlet air temperature of about 70° C. and a product temperature of about 30-50° C. until the water content was NMT 5.0%.
6) The dried granulate was sieved and transferred to a planetary mixer.
7) The granulate, silicified microcrystalline cellulose and hydroxypropymethylcellulose were blended for 20 min.
8) Magnesium stearate was added to preblend from the previous step and blended
9) The finished final blend was compressed to tablets (oblong—18.5 mm×8.0 mm
10) After tabletting tablet cores were coated in a pan coating machine The in-vitro release of lacosamide was measured according to USP (edition 24) method <711>, dissolution apparatus 2, in 900 mL of 0.1N HCl at 50 rpm and is given in the following table.

| Time | Released total amount of active ingredient [%] | | | |
|---|---|---|---|---|
| [min] | Core | 2% | 3% | 5% |
| 15 | 11 | 10 | 8 | 8 |
| 45 | 20 | 19 | 16 | 15 |
| 60 | 24 | 22 | 19 | 18 |
| 120 | 34 | 33 | 29 | 28 |
| 240 | 47 | 48 | 43 | 42 |
| 480 | 66 | 67 | 62 | 62 |
| 720 | 80 | 81 | 76 | 76 |

Examples 37 to 48x Relate to Matrix Tablets Manufactured by Dry Granulation & Direct Compression Example 37

Matrix tablets with following composition per tablet were produced in the following way on a batch size of about 0.5 kg

| Component | Quantity |
|---|---|
| Lacosamide | 25.00 mg |
| Hydroxypropylmethylcellulose (Methocel ® K100M from DOW company) | 12.50 mg |
| Cellulose microcrystalline (type 102) | 25.00 mg |
| Colloidal anhydrous silica | 0.03 mg |
| | 62.53 mg |

1) Lacosamide and colloidal anhydrous silica were mixed and sieved
2) Cellulose microcrystalline (type 102) was added to the pre-mix of lacosamide and colloidal anhydrous silica.
3) The mixture was blended and compacted on a tablet press.
4) The tablets were broken down to granules by passing through a 0.8 mm sieve.
5) Hydroxypropymethylcellulose was added to the granules.
6) The granules and the hydroxypropymethylcellulose were blended
7) The final blend was compressed to tablets (round—Ø5.0 mm).

The in-vitro release of lacosamide was measured according to USP (edition 24) method <711>, dissolution apparatus 2, in 900 mL of 0.1N HCl at 50 rpm and 75 rpm and is given in the following table.

| Time | Released total amount of active ingredient [%] | |
|---|---|---|
| [min] | 50 rpm | 75 rpm |
| 0 | 0 | 0 |
| 15 | 14 | |
| 45 | 29 | |
| 60 | 34 | 33 |
| 120 | 50 | 50 |
| 240 | 73 | 74 |
| 480 | 95 | 97 |
| 720 | 98 | 100 |

Example 38

Matrix tablets with following composition per tablet were produced in the following way on a batch size of about 1.0 kg:

| Component | Quantity |
|---|---|
| Lacosamide | 600.00 mg |
| Hydroxypropylmethylcellulose (Methocel ® K100M from DOW company) | 18.0 mg |
| Cellulose microcrystalline (type 102) | 300.0 mg |

-continued

| Component | Quantity |
|---|---|
| Colloidal anhydrous silica | 5.0 mg |
| Magnesium stearate | 94.0 mg |
| | 1017.0 mg |

1) Lacosamide, colloidal anhydrous silica, cellulose microcrystalline (type 102) and hydroxypropylmethylcellulose were sieved
2) The mixture was blended
3) Magnesium stearate was added to the blend from the previous step and blended
4) The mixture was compacted and the ribbons were broken down to granules by passing through a 1.0 mm sieve.
5) The granules were compressed to tablets (oblong—18.5 mm×8.6 mm).

The in-vitro release of lacosamide was measured according to USP (edition 24) method <711>, dissolution apparatus 2, in 900 mL of 0.1N HCl at 50 rpm and 75 rpm and is given in the following table.

| Time | Released total amount of active ingredient [%] | |
|---|---|---|
| [min] | 50 rpm | 75 rpm |
| 0 | 0 | 0 |
| 15 | 6 | 6 |
| 45 | 12 | 12 |
| 60 | 14 | 15 |
| 120 | 22 | 22 |
| 240 | 33 | 34 |
| 480 | 47 | 49 |
| 720 | 56 | 57 |

Example 39

Matrix tablets with following composition per tablet were produced in the following way on a batch size of about 1.0 kg:

| Component | Quantity |
|---|---|
| Lacosamide | 600.00 mg |
| Hydroxypropylmethylcellulose (Methocel ® K100M from DOW company) | 30.0 mg |
| Cellulose microcrystalline (type 102) | 300.0 mg |
| Colloidal anhydrous silica | 5.0 mg |
| Magnesium stearate | 94.0 mg |
| | 1029.0 mg |

1) Manufacturing process: see example 38
2) Step 5: Following tooling was used for tablet manufacturing: oblong—19.0 mm×10.2 mm The in-vitro release of lacosamide was measured according to USP (edition 24) method <711>, dissolution apparatus 2, in 900 mL of 0.1N HCl at 50 rpm and 75 rpm and is given in the following table.

| Time | Released total amount of active ingredient [%] | |
|---|---|---|
| [min] | 50 rpm | 75 rpm |
| 0 | 0 | 0 |
| 15 | 6 | 6 |
| 45 | 13 | 14 |
| 60 | 16 | 17 |
| 120 | 26 | 27 |
| 240 | 39 | 41 |
| 480 | 54 | 55 |
| 720 | 63 | 64 |

Example 40

Matrix tablets with following composition per tablet were produced in the following way on a batch size of about 0.5 kg:

| Component | Quantity |
|---|---|
| Lacosamide | 300.00 mg |
| Kollidon ® SR from BASF company | 180.0 mg |
| Cellulose microcrystalline (type 102) | 119.4 mg |
| Colloidal anhydrous silica | 0.6 mg |
| Magnesium stearate | 3.0 mg |
| | 603.0 mg | a Kollidon ® SR is an physical mixture of 80% polyvinyl acetate, 19% polyvinyl pyrrolidone, 0.8% sodium lauryl sulfate and 0.2% colloidal anhydrous silica 1) Lacosamide and colloidal anhydrous silica were mixed and sieved
2) Cellulose microcrystalline (type 102) was added to the pre-mix of lacosamide and colloidal anhydrous silica.
3) The mixture was blended, compacted and the ribbons were broken down to granules by passing through a 1.0 mm sieve.
4) Kollidon® SR was added to the granules; the granules and the Kollidon® SR were blended
5) Magnesium stearate was added to the blend from the previous step and then this was mixture blended
6) The final blend was compressed to tablets (oblong—16.3 mm×7.6 mm).

The in-vitro release of lacosamide was measured according to USP (edition 24) method <711>, dissolution apparatus 2, in 900 mL of 0.1N HCl at 50 rpm and 75 rpm and is given in the following table.

| Time | Released total amount of active ingredient [%] | |
|---|---|---|
| [min] | 50 rpm | 75 rpm |
| 0 | 0 | 0 |
| 15 | 11 | 11 |
| 45 | 19 | 20 |
| 60 | 22 | 23 |
| 120 | 33 | 34 |
| 240 | 47 | 49 |
| 480 | 67 | 70 |
| 720 | 80 | 84 |

Example 41

Matrix tablets with following composition per tablet were produced in the following way on a batch size of about 0.5 kg:

| Component | Quantity |
|---|---|
| Lacosamide | 300.00 mg |
| Hydroxypropylcellulose (Klucel ® EF from Ashland Aqualon company) | 90.0 mg |
| Cellulose microcrystalline (type 102) | 150.0 mg |
| Colloidal anhydrous silica | 0.6 mg |
| Magnesium stearate | 3.0 mg |
| | 543.5 mg |

1) Lacosamide, colloidal anhydrous silica, cellulose microcrystalline (type 102) and hydroxypropylcellulose were sieved and blended.
2) Magnesium stearate was added to the blend from the previous step and then blended
3) The mixture was compacted and the ribbons were broken down to granules by passing through a 1.0 mm sieve.
4) The granules were compressed to tablets (oblong—16.3 mm×7.6 mm).

The in-vitro release of lacosamide was measured according to USP (edition 24) method <711>, dissolution apparatus 2, in 900 mL of 0.1N HCl at 50 rpm and 75 rpm and is given in the following table.

| Time | Released total amount of active ingredient [%] | |
|---|---|---|
| [min] | 50 rpm | 75 rpm |
| 0 | 0 | 0 |
| 15 | 10 | 12 |
| 45 | 19 | 28 |
| 60 | 23 | 35 |
| 120 | 36 | 56 |
| 240 | 54 | 83 |
| 480 | 89 | 101 |
| 720 | 100 | 100 |

Example 42

Matrix tablets with following composition per tablet were produced in the following way on a batch size of about 0.5 kg:

| Component | Quantity |
|---|---|
| Lacosamide | 25.00 mg |
| Hydroxypropymethylcellulose (Methocel ® K100M from DOW company) | 12.50 mg |
| Colloidal anhydrous silica | 0.05 mg |
| | 37.55 mg |

11) Manufacturing process: see example 37

12) Step 7: Following tooling was used for tablet manufacturing: round—Ø4.0 mm

The in-vitro release of lacosamide was measured according to USP (edition 24) method <711>, dissolution apparatus 2, in 900 mL of 0.1N HCl at 50 rpm and 75 rpm and is given in the following table.

| Time | Released total amount of active ingredient [%] | |
|---|---|---|
| [min] | 50 rpm | 75 rpm |
| 0 | 0 | 0 |
| 15 | 13 | nd |
| 45 | 25 | nd |
| 60 | 30 | 29 |
| 120 | 46 | 46 |
| 240 | 71 | 71 |
| 480 | 98 | 96 |
| 720 | 101 | 99 |

Example 43

Matrix tablets with following composition per tablet were produced in the following way on a batch size of about 0.5 kg:

| Component | Quantity |
|---|---|
| Lacosamide | 50.0 mg |
| Hydroxypropymethylcellulose (Benecel ® K1500LV-PH from Ashland Aqualon company) | 10.0 mg |
| Silicified microcrystalline cellulose [a] | 39.0 mg |
| Magnesium stearate | 1.0 mg |
| | 100.0 mg |

[a] Silicified microcrystalline cellulose contains 98% cellulose, microcrystalline and 2% silica, colloidal anhydrous 1) Lacosamide and silicified microcrystalline cellulose were blended
2) Hydroxypropymethylcellulose was added to the pre-mix of lacosamide and silicified microcrystalline cellulose and then blended
3) Magnesium stearate was added to the blend from the previous step and then this blended
4) The mixture was compacted and the ribbons were broken down to granules by passing through a 1.0 mm sieve.
5) The granules were compressed to tablets (round—Ø6.5 mm).

The in-vitro release of lacosamide was measured according to USP (edition 24) method <711>, dissolution apparatus 2, in 900 mL of 0.1N HCl at 50 rpm and 75 rpm and is given in the following table.

| Time [min] | Released total amount of active ingredient [%] | |
|---|---|---|
| | 50 rpm | 75 rpm |
| 0 | 0 | 0 |
| 15 | 18 | 18 |
| 45 | 37 | 35 |
| 60 | 45 | 43 |
| 120 | 68 | 63 |
| 240 | 94 | 83 |
| 480 | 101 | 97 |
| 720 | 101 | 100 |

Example 44

Matrix tablets with following composition per tablet were produced in the following way on a batch size of about 0.5 kg:

| Component | Quantity |
|---|---|
| Lacosamide | 50.0 mg |
| Hydroxypropymethylcellulose (Benecel ® K750 LV-PH from Ashland Aqualon company) | 10.0 mg |
| Silicified microcrystalline cellulose [a] | 39.0 mg |
| Magnesium stearate | 1.0 mg |
| | 100.0 mg |

[a] Silicified microcrystalline cellulose contains 98% cellulose, microcrystalline and 2% silica, colloidal anhydrous 1) Manufacturing process: see example 43

The in-vitro release of lacosamide was measured according to USP (edition 24) method <711>, dissolution apparatus 2, in 900 mL of 0.1N HCl at 50 rpm and 75 rpm and is given in the following table.

| Time [min] | Released total amount of active ingredient [%] | |
|---|---|---|
| | 50 rpm | 75 rpm |
| 0 | 0 | 0 |
| 15 | 16 | 16 |
| 45 | 34 | 35 |
| 60 | 41 | 43 |
| 120 | 65 | 69 |
| 240 | 93 | 96 |
| 480 | 100 | 99 |
| 720 | 100 | 99 |

Example 45

Matrix tablets with following composition per tablet were produced in the following way on a batch size of about 1.0 kg:

| Component | Quantity |
|---|---|
| Lacosamide | 300.0 mg |
| Hydroxypropymethylcellulose (Benecel ® K750 LV-PH from Ashland Aqualon company) | 90.0 mg |
| Silicified microcrystalline cellulose [a] | 304.0 mg |
| Magnesium stearate | 6.0 mg |
| | 700.0 mg |

[a] Silicified microcrystalline cellulose contains 98% cellulose, microcrystalline and 2% silica, colloidal anhydrous 1) Lacosamide, hydroxypropymethylcellulose and silicified microcrystalline cellulose were blended.

2) Magnesium stearate was added to the mixture.

3) The mixture was mixed and then compacted.

4) The ribbons were broken down to granules by passing through a 1.0 mm sieve.

5) The granules were compressed to tablets (oblong tooling—18.5 mm×8.0 mm).

The in-vitro release of lacosamide was measured according to USP (edition 24) method <711>, dissolution apparatus 2, in 900 mL of 0.1N HCl at 50 rpm and 75 rpm and is given in the following table.

| Time [min] | Released total amount of active ingredient [%] | |
|---|---|---|
| | 50 rpm | 75 rpm |
| 0 | 0 | 0 |
| 15 | 14 | 15 |
| 45 | 24 | 25 |
| 60 | 27 | 29 |
| 120 | 39 | 43 |
| 240 | 59 | 66 |
| 480 | 86 | 94 |
| 720 | 98 | 100 |

Example 46

Matrix tablets with following composition per tablet were produced in the following way on a batch size of about 1.0 kg:

| Component | Quantity |
|---|---|
| Lacosamide | 300.0 mg |
| Hydroxypropymethylcellulose (Benecel ® K750 LV-PH from Ashland Aqualon company) | 60.0 mg |
| Silicified microcrystalline cellulose [a] | 334.0 mg |
| Magnesium stearate | 6.0 mg |
| | 700.0 mg |

[a] Silicified microcrystalline cellulose contains 98% cellulose, microcrystalline and 2% silica, colloidal anhydrous 1) Manufacturing process: see example 44

The in-vitro release of lacosamide was measured according to USP (edition 24) method <711>, dissolution apparatus 2, in 900 mL of 0.1N HCl at 50 rpm and 75 rpm and is given in the following table.

| Time | Released total amount of active ingredient [%] | |
|---|---|---|
| [min] | 50 rpm | 75 rpm |
| 0 | 0 | 0 |
| 15 | 26 | 32 |
| 45 | 44 | 48 |
| 60 | 50 | 53 |
| 120 | 65 | 67 |
| 240 | 83 | 85 |
| 480 | 97 | 99 |
| 720 | 99 | 100 |

Example 47

Matrix tablets with following composition per tablet were produced in the following way on a batch size of about 0.5 kg:

| Component | Quantity |
|---|---|
| Lacosamide | 300.0 mg |
| Pregelatinized starch (Swelstar ® MX-1 from Asahi KASEI company) | 60.0 mg |
| Cellulose, microcrystalline (type 102) | 150.0 mg |
| Colloidal anhydrous silica | 3.0 mg |
| Magnesium stearate | 0.5 mg |
| | 513.5 mg |

1) Lacosamide, cellulose microcrystalline (type 102), pregelatinized starch and colloidal anhydrous silica were mixed and sieved
2) The mixture was blended for 10 min at speed 1 in a blender and then compacted on a roller compactor
3) The ribbons were broken down to granules by passing through a 0.8 mm sieve.
4) The granules were transferred to a tablet press and compressed to tablets (oblong—16.3 mm×7.6 mm).

The in-vitro release of lacosamide was measured according to USP (edition 24) method <711>, dissolution apparatus 2, in 900 mL of 0.1N HCl at 50 rpm and 75 rpm and is given in the following table.

| Time | Released total amount of active ingredient [%] | |
|---|---|---|
| [min] | 50 rpm | 75 rpm |
| 0 | 0 | 0 |
| 15 | 10 | 10 |
| 45 | 18 | 18 |
| 60 | 21 | 21 |
| 120 | 31 | 31 |
| 240 | 55 | 57 |
| 480 | 81 | 85 |
| 720 | 92 | 97 |

Example 48

Matrix tablets with following composition per tablet were produced in the following way on a batch size of about 0.5 kg:

| Component | Quantity |
|---|---|
| Lacosamide | 50.0 mg |
| Glyceryl dibehenate (Compritol ® 888 ATO from Gattefossé company) | 48.0 mg |
| Lactose spray dried | 94.0 mg |
| Cellulose, microcrystalline (type 102) | 47.0 mg |
| Magnesium stearate | 1.0 mg |
| | 240.0 mg |

1) Lacosamide, microcrystalline cellulose and lactose spray dried were blended
2) Glyceryl dibehenate was added to the pre-mix and blended
3) Magnesium stearate was added to the mixture and blended
4) The final blend was compressed to tablets (round—Ø8.0 mm).

The in-vitro release of lacosamide was measured according to USP (edition 24) method <711>, dissolution apparatus 2, in 900 mL of 0.1N HCl at 50 rpm and 75 rpm and is given in the following table.

| Time | Released total amount of active ingredient [%] | |
|---|---|---|
| [min] | 50 rpm | 75 rpm |
| 0 | 0 | 0 |
| 60 | 29 | 29 |
| 120 | 41 | 41 |
| 240 | 58 | 57 |
| 480 | 76 | 75 |
| 720 | 87 | 87 |

Example 49

Melt-Embedding

Capsules with following composition per capsule were produced in the following way on a batch size of about 1.0 kg:

| Component | Quantity |
|---|---|
| Lacosamide | 50.0 mg |
| Glyceryl palmitostearate (Precirol ® ATO 5 from Gattefossé company) | 9.0 mg |
| | 59.0 mg |

1) Lacosamide and glyceryl palmitostearate were blended.
2) The blend was heated to 60° C. and mixed until a homogenous and uniform dispersion of Lacosamide in glyceryl palmitostearate was obtained.
3) Capsules were filled with the hot lacosamide—glyceryl palmitostearate dispersion
4) The filled capsules were allowed to cool down to room temperature and were closed subsequently.

The in-vitro release of lacosamide was measured according to USP (edition 24) method <711>, dissolution apparatus 2, in 900 mL of 0.1N HCl at 50 rpm and is given in the following table.

| Time [min] | Released total amount of active ingredient [%] 50 rpm |
|---|---|
| 0 | 0 |
| 15 | 12 |
| 45 | 29 |
| 60 | 34 |
| 120 | 50 |
| 240 | 93 |
| 480 | 100 |
| 720 | 101 |

Example 50

Matrix tablets with following composition per tablet were produced in the following way on a batch size of about 1.0 kg:

| Component | Quantity |
|---|---|
| Lacosamide | 5.0 mg |
| Hydroxypropylmethylcellulose (Benecel ® K750 LV-PH from Ashland Aqualon company) | 3.0 mg |
| Silicified microcrystalline cellulose [a] | 6.9 mg |
| Magnesium stearate | 0.1 mg |
| | 15.0 mg |

[a] Silicified microcrystalline cellulose contains 98% cellulose, microcrystalline and 2% silica, colloidal anhydrous 1) Lacosamide, hydroxypropylmethylcellulose and silicified microcrystalline cellulose were blended
2) Magnesium stearate was added to the mixture.
3) The mixture was mixed and then compacted.
4) The ribbons were broken down to granules by passing through a 1.0 mm sieve.
5) The granules were compressed to tablets (round—Ø2.5 mm).
6) Capsules were filled with tablets in order to have a dose of 50 mg per capsule.

The in-vitro release of lacosamide was measured according to USP (edition 24) method <711>, dissolution apparatus 2, in 900 mL of 0.1N HCl at 50 rpm and 75 rpm and is given in the following table.

The in-vitro release of lacosamide was measured according to USP (edition 24) method <711>, dissolution apparatus 2, in 900 mL of 0.1N HCl at 50 rpm and 75 rpm and is given in the following table.

| Time [min] | Released total amount of active ingredient [%] 50 rpm | 75 rpm |
|---|---|---|
| 0 | 0 | 0 |
| 15 | 16 | 14 |
| 45 | 37 | 35 |
| 60 | 45 | 44 |
| 120 | 65 | 67 |
| 240 | 72 | 72 |
| 480 | 71 | 72 |
| 720 | 71 | 71 |

Examples 51 to 52 Relate to Tablets with Functional Coating

Example 51

Film-coated tablets with following composition per tablet were produced in the following way on a batch size of about 1.2 kg:

| Component | Quantity | |
|---|---|---|
| Tablet core: | | |
| Lacosamide | 50.0 mg | |
| Cellulose, microcrystalline (type 101) | 14.0 mg | |
| Povidone (type K30) | 5.0 mg | |
| Silicified microcrystalline cellulose [a] | 47.3 mg | |
| Magnesium stearate | 1.0 mg | |
| Water, purified [b] | q.s. (200 mg) | |
| | 117.3 mg | |
| Film coating: | 2% | 4% |
| Eudragit ® NE 40 D from EVONIK Röhm GmbH company [c, d] | 1.1 mg | 2.2 mg |
| Talc | 1.1 mg | 2.3 mg |
| Colloidal anhydrous silica | 0.1 mg | 0.2 mg |
| Water, purified [b] | q.s. | q.s. |
| | 2.3 mg | 4.7 mg |
| Total (film coated tablet): | 119.6 mg | 122.0 mg |

[a] Silicified microcrystalline cellulose contains 98% cellulose, microcrystalline and 2% silica, colloidal anhydrous
[b] Water is evaporated during process and is not present in final product; q.s. = quantum satis, as much as needed
[c] Eudragit® NE 40 D is an aqueous dispersion with a solid content of 40.0 wt-% consisting of neutral ethyl acrylate/metyl methacrylate copolymer (2:1) (38.0 wt-%) and nonoxynol 100 (2.0 wt-%).
[d] Water is evaporated during process and is not present in final product, 1.1 mg, 1.6 mg and 2.2 mg corresponds to 2.8 mg, 4.0 mg and 5.5 mg 40 wt-% Eudragit® NE 40 D dispersion 1) The binder solution was prepared by dissolving povidone in purified water.
2) Lacosamide, microcrystalline cellulose and silicified microcrystalline cellulose were transferred into a high-shear granulator and mixed 3) The binder solution was added to the dry mixture under continuous stirring.
4) The mixture was granulated.
5) The wet granulate was transferred into a tray dryer and dried at 40° C. for 16 h.
6) The dried granulate was sieved and transferred to the high-shear granulator.
7) Magnesium stearate and the granules from the previous step were blended
8) The final blend was compressed to tablets (round—Ø5.0 mm).
9) The coating dispersion was prepared by dispersing talc in purified water. Eudragit® NE40D and colloidal anhydrous silica were added and mixed until a homogenous dispersion was obtained.
10) The tablets were coated in a pan coating system with the coating suspension until the target weight was reached.

The in-vitro release of lacosamide was measured according to USP (edition 24) method <711>, dissolution apparatus 2, in 900 mL of 0.1N HCl at 50 rpm and 75 rpm and is given in the following table.

| Time | Released total amount of active ingredient [%] | | | |
|---|---|---|---|---|
| | 2% | | 4% | |
| [min] | 50 rpm | 75 rpm | 50 rpm | 75 rpm |
| 0 | 0 | 0 | 0 | 0 |
| 15 | 0 | 0 | 0 | 0 |
| 45 | 7 | 15 | 4 | 8 |
| 60 | 14 | 24 | 8 | 15 |
| 120 | 39 | 53 | 23 | 38 |
| 240 | 68 | 78 | 46 | 65 |
| 480 | 89 | 92 | 68 | 86 |
| 720 | 93 | 94 | 79 | 93 |

Example 54

Film-coated tablets with following composition per tablet were produced in the following way on a batch size of about 1.2 kg:

| Component | Quantity | |
|---|---|---|
| Tablet core: | | |
| Lacosamide | 50.0 mg | |
| Hydroxypropylcellulose | 1.3 mg | |
| Silicified microcrystalline cellulose [a] | 42.0 mg | |
| Magnesium stearate | 0.5 mg | |
| Water, purified [b] | q.s. (55 mg) | |
| | 93.8 mg | |
| Film coating: | 2% | 3% |
| Kollicoat ® SR 30 D from BASF company [c, d] | 1.7 mg | 2.5 mg |
| Propylene glycol | 0.2 mg | 0.3 mg |
| Water, purified [b] | q.s. | q.s. |
| | 1.9 mg | 2.8 mg |
| Total (film coated tablet): | 95.7 mg | 96.6 mg |

[a] Silicified microcrystalline cellulose contains 98% cellulose, microcrystalline and 2% silica, colloidal anhydrous
[b] Water is evaporated during process and is not present in final product; q.s. = quantum satis, as much as needed
[c] Kollicoat ® SR 30 D is an aqueous dispersion with a solid content of 30 wt-% consisting of polyvinylacetate (27 wt-%), polyvinylpyrrolidone (2.7 wt-%) and sodium lauryl sulfate (0.3 wt-%)
[d] Water is evaporated during process and is not present in final product, 1.7 mg and 2.5 mg, respectively, corresponds to 5.7 mg and 8.3 mg, respectively, of 30 wt-% Kollicoat ® SR 30 D dispersion 1) The binder solution was prepared by dissolving hydroxypropylcellulose in purified water.
2) Lacosamide, microcrystalline cellulose and silicified microcrystalline cellulose were transferred into a high-shear granulator and mixed
3) The binder solution was added to the dry mixture under continuous stirring.
4) The mixture was granulated.
5) The wet granulate was transferred into a tray dryer and dried at 40° C. for 16 h. The dried granulate was sieved and transferred to the high-shear granulator.
6) Magnesium stearate and the granules from the previous step were blended
7) The final blend was compressed to tablets (round—Ø5.0 mm).
8) The coating dispersion was prepared by dispersing Kollicoat® SR30D and propylene glycol in purified water and the mixture was stirred until a homogenous dispersion was obtained.
9) The tablets were coated in a pan coating system with the coating suspension until the target weight was reached.

The in-vitro release of lacosamide was measured according to USP (edition 24) method <711>, dissolution apparatus 2, in 900 mL of 0.1N HCl at 50 rpm and 75 rpm and is given in the following table.

| Time | Released total amount of active ingredient [%] | | | |
|---|---|---|---|---|
| | 2% | | 3% | |
| [min] | 50 rpm | 75 rpm | 50 rpm | 75 rpm |
| 0 | 0 | 0 | 0 | 0 |
| 15 | 3 | 3 | 1 | 1 |
| 45 | 7 | 7 | 3 | 5 |
| 60 | 11 | 9 | 4 | 7 |
| 120 | 34 | 36 | 8 | 22 |
| 240 | 69 | 69 | 38 | 51 |
| 480 | 94 | 91 | 69 | 78 |
| 720 | 100 | 97 | 85 | 92 |

Example 53

Production of Lacosamide Polymorph Form (I)

Crude lacosamide was suspended in ethyl acetate (10 volumes), heated to reflux, seeded with form (I) of lacosamide and slowly cooled down to room temperature to afford substantially optically pure lacosamide in crystalline form (I).

Example 54

The Pharmacokinetic (PK)-pharmacodynamic (PD) Modeling of Seizure Frequency in Subjects with Partial-onset Seizures.

Introduction and Objectives

This report describes the objectives, methods, assumptions, and results of the pharmacokinetic (PK)-pharmacodynamic (PD) modelling of seizure frequency in subjects with partial-onset seizures with or without secondary generalization who receive adjunctive treatment with adjunctive lacosamide (LCM, also referred to as SPM 927 and formerly referred to as harkoseride).

Objectives of the PK-PD analysis were to evaluate and describe the correlation between the LCM plasma concentration over time (PK parameter) and the reduction of daily seizures over time (PD parameter) based on the pooled data from the previous clinical human trials.

The results of this PK-PD modelling should provide supportive information about the therapeutic LCM dose range.

PK-PD Modeling Results

The evaluation of PK-PD modeling was done based on the $E_{max}$ model.

$E_{max}$ PK-PD Model

The following Table 8 summarizes the PK-PD modeling results using the $E_{max}$ model.

TABLE 8

PK-PD results of $E_{max}$ model (N = 615 subjects)

| Parameter | Arithmetic mean (SD) | Median | Range | 1st, 3rd quantile |
|---|---|---|---|---|
| AUC50[a] [μg/mL*h] | 35.9 (185.6) | 1.05 | 0-3998 | 0, 27.27 |
| $E_{max}$ [%] | 71.0 (30.0) | 77.0 | 0.06-100 | 47, 7, 100 |

[a]AUC50 = AUC needed to achieve half of the maximum effect

Data source: Appendix 9 (Part 2)

The arithmetic mean of AUC50 was determined to be 35.9 μg/mL*h, with a high variability (Range: 0-3998 μg/mL*h).

The FIG. 7 illustrates the correlation between the predicted and measured change of the seizure frequency for all the data included in the PK-PD modeling using the $E_{max}$ model.

Summary for $E_{max}$ PK-PD Model

The maximum of the effect by administration of LCM ($E_{max}$) was estimated to be 71% reduction of the seizure frequency. The mean AUC50 (ie, AUC at steady-state to achieve half of the maximum decrease in partial seizure frequency) was estimated to be 35.9 μg/mL*h. This AUC corresponds to an AUC that is obtained in individuals by administration of a dose of about 110 mg LCM bid in a typical subject with a volume of distribution ($V_d$) of 50 L and a $k_e$ of 0.06 h$^{-1}$ (corresponding to a terminal half-life of approximately 12 hours).

To achieve a decrease of the daily number of seizures by 46% corresponding to 65% of the maximum effect, an AUC of 67 μg/mL*h (corresponding to a mean dose of 200 mg LCM bid in a typical subject) is needed, whereas an AUC of 100 μg/mL*h (corresponding to a mean dose of 300 mg LCM bid in a typical subject) is needed to have a decrease of the daily number of partial seizures of 52% corresponding to 74% of the maximum effect.

The achievable PD effect (decrease of the daily number of seizures in %) in relation to the AUC needed for this effect, and the corresponding doses (to achieve those AUCs) are summarized in the following Table 9:

TABLE 9

Achievable decrease of the daily number of seizures (%) in relation to $AUC_{\square,ss}$ and daily lacosamide dose (based on results of $E_{max}$ model)[a]

| Decrease of daily number of seizures, E(AUC) % of base line | Decrease of daily number of seizures, E(AUC) % of $E_{max}$ | Corresponding $AUC_{\square, ss}$ | Daily dose to achieve corresponding $AUC_{\square, ss}$[b] |
|---|---|---|---|
| 22.5 | 31.7 | 16.7 μg/mL*h | 50 mg bid |
| 34.2 | 48.1 | 33.3 μg/mL*h | 100 mg bid |
| 35.1 | 50 | 35.9 μg/mL*h | 110 mg bid |
| 41.3 | 58.2 | 50 μg/mL*h | 150 mg bid |
| 46.1 | 65.0 | 66.7 μg/mL*h | 200 mg bid |
| 49.6 | 69.9 | 83.3 μg/mL*h | 250 mg bid |
| 52.2 | 73.6 | 100 μg/mL*h | 300 mg bid | bid = twice daily;
[a]calculated based on the results of the $E_{max}$ model according to equation given under 2.5.5.2;
E(AUC) = Decrease of daily number of seizures in % as function of AUC,
[b]Lacosamide daily dose needed in a subject with a $V_d$ (volume of distribution) of 50 L and a $k_e$ (rate constant of elimination) of 0.06 h$^{-1}$; approximation of dose was done based on the equation Dose = $AUC_{\square,ss}/V_d*k_e$ The FIG. 8 illustrates the achievable decrease of the daily number of seizures in percent of the maximum effect and as percent of the base line frequency in relation to the dose.

Discussion

In the present report, the linear regression of the cumulative daily number of seizures for each visit during the Baseline, Titration, and Maintenance Phase was shown to be an appropriate method to characterize the mean daily number of seizures. The slope of the linear regression is equal to the mean daily number of seizures.

In a first step, the validity of the developed equations for approximation of $AUC_{\square,ss}$, the PK parameter of interest in the current PK-PD evaluation, was shown.

Based on the relative difference of the individual slopes during Titration and Maintenance Phase vs Baseline slope and the approximated $AUC_{T,ss,m}$, the PK-PD evaluation was performed using a linear model, the $E_{max}$ model, and the $E_{max}$ 100 model. All 3 models resulted in model parameter results with very high variability. Finally, the $E_{max}$ model had the lowest weighted sum of squares and was therefore selected as the most appropriate PK-PD model to describe the data. As a result of the $E_{max}$ model, the mean of the parameter AUC50 was estimated to be 35.9 μg/mL*h and the mean maximum effect ($E_{max}$) was estimated to be a reduction by 71% of the base line frequency of seizures. The AUC50 is defined as the $AUC_{\square,ss}$ that is needed in individuals to achieve 50% of the maximum effect (decrease in seizure frequency). This $AUC_{\square,ss}$ corresponds to an AUC that is obtained in individuals by administration of a dose of approximately 110 mg LCM bid in a typical subject with a volume of distribution of 50 L and a $k_e$ of 0.06 h$^{-1}$ (corresponding to a terminal half-life of approximately 12 hours).

Based on the current results of the $E_{max}$ model, it can be predicted that an $AUC_{\square,ss}$ of 67 μg/mL*h (corresponding to a mean dose of 200 mg LCM bid in a typical subject) is needed to have a decrease of the daily number of seizures of 46% corresponding to a decrease of 65% of the maximum effect, whereas an $AUC_{\square,ss}$ of 100 μg/mL*h (corresponding to a mean dose of 300 mg LCM bid in a typical subject) is needed to have a decrease of the daily number of seizures of 52% corresponding to a decrease of 74% of the maximum effect. These results support the therapeutic range of LCM doses (200-600 mg/day) that have been shown to be effective for reducing partial seizure frequency.

The high variability in the PD parameter should be considered when interpreting the current PK-PD modeling results. There is a wide distribution of the daily number of seizures in the trial population; for example, some patients have 0.1 seizures per day and some have more than 20 seizures per day. Based on this, a wide range of parameter values for AUC50 and $E_{max}$ was not unexpected.

The Example suggests that
All tested PK-PD models (linear model, $E_{max}$ model, $E_{max}$ 100 model) resulted in model parameter results with very high variability. The $E_{max}$ model showed the lowest weighted sum of squares and was therefore identified as the most appropriate PK-PD model to describe the relation between AUC and seizure frequency change.

As a result of the $E_{max}$ model, the AUC50 (ie, $AUC_{\square,ss}$ to achieve 35% decrease in partial seizure frequency corresponding to a decrease of 50% of the maximum effect) was estimated to be 35.9 µg/mL*h. This $AUC_{\square,ss}$ corresponds to an $AUC_{\square,ss}$ that is obtained in individuals by administration of a dose of about 110 mg LCM bid in a typical subject with a volume of distribution of 50 L and a $k_e$ of 0.06 h$^{-1}$ (corresponding to a terminal half-life of approximately 12 hours).

Based on the current results of the $E_{max}$ model, it can be predicted that an $AUC_{\square,ss}$ of 67 µg/mL*h (corresponding to a mean dose of 200 mg bid in a typical subject) is needed to have a decrease of the daily number of seizures of 46% corresponding to a decrease of 65% of the maximum effect, whereas an $AUC_{\square,ss}$ of 100 µg/mL*h (corresponding to a mean dose of 300 mg LCM bid in a typical subject) is needed to have a decrease of the daily number of partial seizures of 52% corresponding to a decrease of 74% of the maximum effect.

The current PK-PD results support the therapeutic range of LCM doses (200-600 mg/day) that have been shown to be effective as an adjunctive treatment for reducing partial seizure frequency.

Example 55

Simulation of Adverse Event Profile after Once Daily Administration of Lacosamide MR Formulation Based on the results of (a) a clinical trial ("trial 640") examining adverse events (AE) and PR interval increases after the administration of lacosamide immediate release formulation, and (b) a phase I pk trial after administration of an MR formulation of lacosamide (Example 2), the adverse events including PR interval effects following the administration of a 400 mg MR formulation, once daily, have been simulated as follows:

A. Basic Parameters used:
Population parameters using the combined PK analysis of two clinical trials (trial 640 and Example 2)
Simulation of a trial with 4 arms, 54 subjects per arm with 6 days of dosing
Placebo
200 mg MR QD
400 mg MR QD
200 mg IR BID (400 mg/day)
Absorption half life and bioavailability with inter-individual variabilities for the MR administration in the Phase I trial of Example 2 is used for the two MR treatment arms
Absorption half life with inter-individual variabilities for the IR administration in trial 640 and Example 2 is used for the IR treatment arm.
1 day pre-treatment, 6 days of dosing (no up-titration), 2 days of washout, concentrations at every hour B. Simulating AE and PR-interval profiles:
The simulated concentrations were used to simulate 100 new trials using the PR-interval and the AE PKPD final model
First calculate maximum change from baseline for each individual
Then calculate predicted mean maximum change across individuals for a treatment within a trial and examine the distribution of mean maximum change for the different simulated trials
Calculate the predicted incidence of first degree AV-block (PR-interval>209 msec) over all the simulated subjects
Calculate the predicted number of subjects with >10% increase from baseline over all the simulated subjects
Time profile of mean across trials of number of AEs or AE-incidence (%) per trial
Distribution across trials of number of patients per trial with an AE
Distribution across trials of total number of hours with an AE per trial C. Results of simulations:
(i) A slightly lower PR-interval increase is predicted for the 400 mg MR QD administration compared to 200 mg BID IR (6.4 vs 7.7 msec)
(ii) The predicted number of patients with more than 10% increase in PR interval is 50% higher in the BID IR treatment arm than the 400 mg QD MR arm (11.96 vs 8.11)
(iii) Differences in AE nausea profiles between 400 mg QD MR and 200 mg BID IR are less pronounced but are still present: difference in AE incidence is driven by higher IR peaks
(iv) Dizziness AE profile and dizziness summary measures result in a drop from peak incidences of 12% during 200 mg BID IR to 8% during 400 mg QD.

A minor part of the differences is explained by the difference in bioavailability but a major part of the effect is due to the difference in peak concentrations.

The following items form an illustrative, non limiting part of the invention:
1. A solid controlled release formulation of lacosamide for oral administration, the composition comprising lacosamide and an agent for retarding the release of the lacosamide, wherein
   (a) an amount of about 8.5 wt-% to about 41 wt-% of lacosamide relative to the total lacosamide content of the formulation is released within 1 h,
   (b) an amount of about 15 wt-% to about 64 wt-% of lacosamide relative to the total lacosamide content of the formulation is released within 2 h, and/or
   (c) an amount of about 28 wt-% to about 88 wt-% of lacosamide relative to the total lacosamide content of the formulation is released within 4 h,
   when the in-vitro release of lacosamide is measured according to USP (edition 24) method <711>, dissolution apparatus 2, in 900 mL of 0.1N HCl at 75 rpm.
2. The formulation according to item 1,
   (a) wherein an amount of about 9.5 wt-% to about 26 wt-% of lacosamide relative to the total lacosamide content of the formulation is released within 1 h,
   (b) an amount of about 18 wt-% to about 45 wt-% of lacosamide relative to the total lacosamide content of the formulation is released within 2 h, and/or
   (c) wherein an amount of about 33 wt-% to about 70 wt-% of lacosamide relative to the total lacosamide content of the formulation is released within 4 h.

3. The formulation according to item 1 or 2, wherein lacosamide is present in an amount of 20 to 95 wt-%, in an amount of 30 to 50 wt %, or in an amount of 50 to 95 wt %.
4. The formulation according to any one of the preceding items, wherein a single dose comprises from about 50 mg to about 1000 mg lacosamide, preferably from about 200 mg to about 800 mg lacosamide, more preferably from about 300 mg to about 600 mg lacosamide.
5. The formulation according to any one of the preceding items for once daily administration, in particular at a dosing interval of 24 h.
6. A solid controlled release formulation of lacosamide for oral once daily administration, the composition comprising lacosamide and an agent for retarding the release of the lacosamide, wherein said controlled release formulation releases lacosamide in an amount to provide an in-vivo rate constant of lacosamide absorption ka of about 0.1/h to about 0.5/h
7. The formulation according to any one of the preceding items, providing an in-vivo rate constant of lacosamide absorption ka of about 0.1/h to about 0.3/h.
8. The formulation according to item 7, wherein lacosamide is released from the formulation with a constant rate of dissolution $k_{diss}$ of about 0.1/h to about 0.3/h when the in-vitro release of lacosamide is measured according to USP (edition 24) method <711>, dissolution apparatus 2, in 900 mL of 0.1N HCl at 50 rpm.
9. The formulation according to item 8 wherein the constant rate of dissolution $k_{diss}$ of about 0.1/h to about 0.2/h.
10. The formulation according to any one of the preceding items, wherein the time after administration to reach the maximum lacosamide plasma concentration at steady state after repeated once daily administration Tmax,ss is between about 4 h and 10 h, preferably between about 5 h and 9 h.
11. The formulation according to any one of the preceding items, wherein the composition is formulated to provide a steady state peak to trough fluctuation (PTF) of less than 70%, wherein the PTF is (Cmax,ss-Cmin,ss)/AUC/tau, with Cmax,ss being the maximal plasma concentration of lacosamide at steady state, and Cmin,ss being the minimal plasma concentration of lacosamide at steady state after oral administration, and AUCt,ss being the area under the curve for the dosing interval tau in the steady state, and the dosing interval tau being 24 h.
12. The formulation according to item 10, wherein the PTF is less than about 55%, or less than about 45%.
13. The formulation according to any one of the preceding items wherein in the steady-state after repeated once daily administration Cmax, ss, norm is in the range of 0.016 µg/mL/mg and 0.0215 µg/mL/mg, and Cmin, ss, norm is in the range 0.01 µg/mL/mg to 0.014 µg/mL/mg in patients with an average distribution volume of 50 L
14. The formulation according to any one of the preceding items for use in the prevention, alleviation, and/or treatment of a disease of the central nervous system.
15. The formulation according to item 14, wherein the disease is selected from pain, epilepsy, disorders associated with epileptic seizures, essential tremor, bipolar disorder, schizophrenia, obsessive compulsive disorders, dyskinesia, or hyperexcitability disorders.
16. The formulation according to item 15, wherein the disease is selected from epilepsy, disorders associated with epileptic seizures, essential tremor, and bipolar disorder.
17. The formulation according to any one of the preceding items for use in epileptic seizure prevention and/or the treatment of epilepsy.
18. The formulation for use according to any one of the preceding items, wherein the incidence of side effects is reduced compared to an immediate release formulation comprising the same amount of lacosamide and releasing more than 80% of lacosamide within 30 minutes when measured according to USP (edition 24), method <711>, dissolution apparatus 2, in 900 mL of 0.1N HCl at 75 rpm.
19. The formulation for use according to any one of the preceding items, wherein the seizure frequency is reduced compared to the seizure frequency achieved by the administration of an immediate release formulation comprising the same amount of lacosamide, and releasing more than 80% of lacosamide within 30 minutes when measured according to USP (edition 24), method <711>, dissolution apparatus 2, in 900 mL of 0.1N HCl at 75 rpm.
20. The formulation according to any one of the preceding items for use in epileptic seizure prevention and/or treatment of epilepsy by oral administration once a day at a dosing interval tau of about 24 h.
21. The formulation according to any one of the preceding items, wherein a single dose of the formulation comprises at least about 400 mg lacosamide.
22. The formulation according to any one of the preceding items in the form of a solid oral dosage, preferably selected from tablets with functional coating, tablets with non functional coating, capsules, mini tablets, pellets and granules.
23. The formulation according to any one of the preceding items in the form of a solid oral dosage selected from matrix tablets, functionally coated tablets and coated granules.
24. The formulation according to any one of the preceding items comprising lacosamide as active ingredient and at least one retardation agent which delays the in-vitro release of lacosamide from said formulation compared to a lacosamide immediate release formulation.
25. The formulation according to item 24, comprising a lacosamide-containing matrix which comprises at least one matrix retardation agent.
26. The formulation according to item 25, wherein the at least one matrix retardation agent is a hydrophilic polymer material having a viscosity of 2,000 mPas to 200,000 mPas in a 2 wt-% aqueous solution at 20° C., preferably a viscosity of 10,000 mPas to 150,000 mPas in a 2 wt-% aqueous solution at 20° C.
27. The formulation according to item 26, wherein the at least one hydrophilic polymer is selected from the group of gums, cellulose derivatives, cellulose ethers, cellulose esters, materials derived from proteins, poly saccharides, starch, starch derivatives, vinyl acetate derivatives, vinyl pyrrolidone derivatives, polyethylene glycols, and preferably selected from the group of poloxamers, hydroxyethylcellulose, hydroxypropylcellulose, methylcellulose, hydroxypropylmethylcellulose, polyvinyl pyrrolidone, polyvinyl alcohols, modified starch, pregelatinized starch, hydroxypropyl starch, sodium hyaluronate, alginic acid, alginate salts, carrageenan, chitosan, guar gum, pectin, and xanthan gum.

28. The formulation according to item 25, wherein the at least one matrix retardation agent is selected from non-polymer material having a melting point greater than 37° C., preferably a melting point ranging from 40° C. to 100° C.

29. The formulation according to item 28, wherein the at least one matrix retardation agent is hydrophobic, and is preferably selected from the group of fats, lipids, waxes, fatty alcohols, fatty acids, fatty alcohol ethers, and fatty acid esters.

30. The formulation of item 29 wherein said matrix retardation agent is, selected from the group consisting of C8-C30 monohydric alcohols, monoglycerides, diglycerides, triglycerides, glycerine esters, hydrogenated castor oil, glyceryl behenate, hydrogenated soybean oil, lauroyl macrogolglycerides, stearyl macrogolglycerides, glyceryl palmitostearate, cethyl palmitate, glycerol esters of fatty acids and cetyl alcohol.

31. The formulation according to item 25, wherein the at least one matrix retardation agent is an inert polymer selected from the group consisting of acrylic resins, cellulose derivatives, vinyl acetate derivatives, and non-water soluble polyesters.

32. The formulation of item 31 wherein the at least one retardation agent is selected from the group consisting of polyvinyl acetate, ethylcellulose, hydroxypropylmethylcellulose acetate phthalate, hydroxypropylmethylcellulose acetate succinate, shellac, polymethacrylic acid derivatives, methacrylic acid copolymer type A, methacrylic acid copolymer type B, methacrylic acid copolymer type C, ammonio methacrylate copolymer type A, ammonio methacrylate copolymer type B, neutral ethyl methyl methacrylate copolymer and basic butylated methacrylate copolymer.

33. The formulation according to any one of the preceding items, wherein the formulation comprises at least one matrix retardation agent in a total amount of at least about 2.5 wt-%, preferably at least about 5 wt-%, more preferably at least about 10 wt-% relative to the total weight of the formulation.

34. The formulation according to item 33, wherein the matrix retardation agent is selected from the group of hydroxypropylmethylcelluloses, polyethylene glycols, ethylcelluloses, triglycerides, glyceryl behenate, polyvinyl acetates, methacrylic acid copolymer type B and neutral methacrylic acid in a total amount of 10 wt-% to 30 wt-% relative to the total weight of the formulation.

35. A solid controlled release formulation of lacosamide for oral administration, wherein the formulation comprises
(a) lacosamide in an amount of 20 to 95 wt-%,
(b) at least one matrix retardation agent in a total amount of 5 to 80 wt-%, and, optionally
(c) one or more excipients in a total amount of up to 75 wt-%, and selected from the group of fillers, diluents, binders, lubricant, glidants, pharmaceutically acceptable processing aid agents, and/or flow modifiers, and/or
(d) a non-functional film coat in an amount of up to 30 wt-%.

36. The formulation according to item 35, wherein the formulation is a tablet and comprises lacosamide in an amount of 70 to 95 wt-%, a matrix retardation agent in an amount of 5 to 30 wt-%, a filler and/or diluent in an amount of 0 to 25 wt-%, a binder in an amount of 0 to 15 wt-%, a lubricant, glidant and/or flow modifier in an amount of 0 to 10 wt-%, and a non-functional film coat in an amount of 0 to 10 wt-%, all amounts relative to the total weight of the formulation.

37. The formulation according to any one of items 1 to 34, wherein the formulation is a tablet and comprises lacosamide in an amount of 1 to 80 wt-%, a matrix retardation agent in an amount of 5 to 80 wt-%, a filler and/or diluent in an amount of 0 to 80 wt-%, a binder in an amount of 0 to 80 wt-%, a lubricant, glidant and/or flow modifier in an amount of 0 to 80 wt-%, and a non-functional film coat in an amount of 0 to 30 wt-%, all amounts relative to the total weight of the formulation.

38. The formulation to according to item 37 comprising lacosamide in an amount of 30 to 60 wt-%, a matrix retardation agent in an amount of 5 to 30 wt-%, a filler in an amount of 20 to 55 wt-%, a binder in an amount of 10 to 50 wt-%, a lubricant, glidant and/or flow modifier in an amount of 0 to 20 wt-%, and a non-functional film coat in an amount of 0 to 5 wt-% all amounts relative to the total weight of the formulation.

39. A solid controlled release formulation of lacosamide for oral administration, wherein the formulation comprises
(a) a lacosamide-containing matrix, and
(b) at least one release controlling layer surrounding said lacosamide-containing matrix, the at least one release controlling layer comprising a release controlling agent.

40. The formulation according to item 39, wherein the lacosamide-containing matrix comprises at least one excipient.

41. The formulation according to item 39 or 40, wherein the lacosamide-containing matrix (a) is
(i) an immediate release matrix, or
(ii) a modified release matrix comprising at least one release controlling agent.

42. The formulation according to item 41, wherein the release controlling agent in (ii) is selected from matrix retardation agents as defined in any one of the items 26 to 34.

43. The formulation according to any one of items 39 to 42, wherein the release controlling layer comprises at least one polymer which is selected from the group consisting of acrylic resins, cellulose derivatives, vinyl acetate derivatives, and preferably selected from polyvinyl pyrrolidone, polyvinyl acetate, ethylcellulose, hydroxypropylmethylcellulose acetate phthalate, hydroxypropylcellulose, hydroxypropylmethylcellulose acetate succinate, shellac, methacrylic acid copolymer type A, methacrylic acid copolymer type B, methacrylic acid copolymer type C, ammonio methacrylate copolymer type A, ammonio methacrylate copolymer type B, neutral ethyl methyl methacrylate copolymer, and basic butylated methacrylate copolymer.

44. The formulation according to any one of items 39 to 43, wherein the release controlling layer is present in an amount of 1 to 60 wt-%, preferably in an amount of 5 to 45 wt %, and more preferably in an amount of 5 to 35 wt-% relative to the total weight of the formulation.

45. The formulation according to any one of items 39-42, wherein the release controlling layer comprises a polymer that is selected from the group of ethylcelluloses, polyvinyl acetates, methacrylic acid copolymer type B and neutral ethyl acrylate methyl methacrylate copolymer in a total amount of 5 to 35 wt-% relative to the total weight of the formulation.

46. The formulation according to item 45, wherein the release controlling layer contains at least one additional excipient selected from the group of co-binders, pore formers, anti-sticking agents, antifoam agents, flavouring agents, pigments, dyes, and processing aid agents, like plasticizers, emulsifier or stabilizer.

47. The formulation according to any one of items 39 to 46, wherein an intermediate layer is located between the lacosamide-containing matrix and the release controlling layer.

48. The formulation according to any one of items 39 to 47, wherein the release controlling layer is coated with a final outer layer.

49. The formulation according to any one of items 39 to 48, comprising lacosamide in an amount of 1 to 95 wt-%, a filler and/or diluent in an amount of 0 to 80 wt-%, a binder in an amount of 0 to 80 wt-%, and a controlled release layer in an amount of 1 to 60 wt-%.

50. The formulation according to item 49, comprising lacosamide in an amount of 50 to 95 wt-%, a filler and/or diluent in an amount of 0 to 30 wt-%, a binder in an amount of 0 to 15 wt-%, and a controlled release layer in an amount of 5 to 35 wt-%.

51. The formulation according to item 48 that is compressed to a multiple unit dose tablet or multiple unit dose film-coated tablet by adding a filler and/or diluent in an amount of 20 to 80 wt-%, a binder in an amount of 0 to 80 wt-%, a lubricant, glidant and/or flow modifier in an amount of 0 to 80 wt-%, and a non-functional film coat in an amount of 0 to 30 wt-%.

52. The formulation according to any one of the preceding items, wherein said formulation is in the form of a single unit dosage.

53. The formulation according to any one of the items 1-50, wherein said formulation is a multiple unit dosage comprising pellets, minitablets, or granules, which are optionally packed into sachets or capsules, or are compressed to multiple unit tablets.

54. The formulation according to item 53 wherein the maximum size of the single particles, pellets, minitablets or granules is not more than 3 mm, and more preferably 0.1 to 2.5 mm.

55. The formulation according to any one of the preceding items, wherein the in vitro-release of lacosamide is pH independent.

56. A method of manufacturing a solid formulation comprising a lacosamide controlled release matrix, wherein the method comprises the following steps:
   (a) mixing suitable amounts of lacosamide, a matrix retardation agent, and optionally a binder, preferably in an aqueous solvent,
   (b) granulating the mixture produced in step (a), preferably by wet granulation,
   (c) adding the remaining matrix excipients and mixing with the granules produced in step (b),
   (d) pressing the blend produced in step (c) to tablets, and
   (e) optionally applying a coating to the tablets obtained in step (d).

57. A method for the prevention, alleviation, and/or treatment of a disease of the central nervous system comprising administration of a formulation of anyone of items 1 to 55.

58. The method of item 57, wherein the disease is selected from pain, epilepsy, disorders associated with epileptic seizures, essential tremor, bipolar disorder, schizophrenia, obsessive compulsive disorders, dyskinesia, or hyperexcitability disorders.

59. The method of item 57, wherein the disease is selected from epilepsy, disorders associated with epileptic seizures, essential tremor, and bipolar disorder.

60. The method of item 57 for epileptic seizure prevention and/or the treatment of epilepsy.

61. The method of item 57 wherein the incidence of side effects is reduced compared to an immediate release formulation comprising the same amount of lacosamide and releasing more than 80% of lacosamide within 30 minutes when measured according to USP (edition 24), method <711>, dissolution apparatus 2, in 900 mL of 0.1N HCl at 75 rpm.

62. The method of item 60 wherein the seizure frequency is reduced compared to the seizure frequency achieved by the administration of an immediate release formulation comprising the same amount of lacosamide, and releasing more than 80% of lacosamide within 30 minutes when measured according to USP (edition 24), method <711>, dissolution apparatus 2, in 900 mL of 0.1N HCl at 75 rpm.

63. The method of item 60 for epileptic seizure prevention and/or treatment of epilepsy by oral administration once daily.

The invention claimed is:

1. A solid controlled release formulation for oral administration of lacosamide, the formulation comprising lacosamide and a lacosamide release controlling agent, wherein the solid controlled release formulation is configured such that
   a. an amount of about 8.5 wt % to about 41 wt % of lacosamide relative to the total lacosamide content of the formulation is released within 1 h,
   b. an amount of about 15 wt % to about 64 wt % of lacosamide relative to the total lacosamide content of the formulation is released within 2 h, and
   c. an amount of about 28 wt % to about 88 wt % of lacosamide relative to the total lacosamide content of the formulation is released within 4 h,
   when the in-vitro release of lacosamide is measured according to USP (edition 24) method <711>, dissolution apparatus 2, in 900 mL of 0.1N HCl at 75 rpm, wherein lacosamide is present in an amount of 20 to 95 wt % relative to the total weight of the formulation and the lacosamide release controlling agent is present in a lacosamide-containing matrix in an amount from 10 wt % to 50 wt %.

2. The formulation according to claim 1, wherein a single dose comprises about 100 mg to about 600 mg lacosamide.

3. The formulation according to claim 1 for once daily administration at a dosing interval of about 24 h.

4. The formulation according to claim 1, wherein said formulation is configured to provide an in vitro dissolution rate measured according to USP (edition 24) method <711>, dissolution apparatus 2, in 900 mL of 0.1N HCl at 75 rpm, which meets at least four of the following dissolution rates:
   a. within one hour about 11 to about 26 wt %,
   b. within two hours about 21 to about 45 wt %,
   c. within four hours about 38 to about 70 wt %,
   d. within six hours about 52 to about 83 wt %,
   e. within eight hours about 64 to about 91 wt %,
   f. within 10 hours at least about 72 wt %,
   g. within 18 hours at least about 90 wt %.

5. The formulation according to claim 1, wherein the time after administration to reach the maximum lacosamide plasma concentration at steady state after repeated once daily administration $T_{max}$,ss is between about 5 h and 9 h.

6. A solid pharmaceutical composition for once daily oral administration of lacosamide according to claim 1, said solid formulation
(1) comprising
   (a) about 100 to 800 mg of lacosamide, and
   (b) at least one lacosamide release controlling agent, being present
      (b1) in the matrix of said solid composition in an amount of 10 to 50 wt %, relative to the total weight of the formulation and
      (b2) in the coating of said solid composition in an amount of 5 to about 35 wt % relative to the total weight of the formulation, and
   (c) one or more further therapeutically acceptable excipients, and
(2) configured to deliver
   (2.1) the in-vitro dissolution profile according to claim 1, and/or
   (2.2) after once daily administration to animals, a pharmacokinetic profile comprising the following features:
      (a) a $C_{max}$,ss,norm of 0.016 to 0.023 µg lacosamide/ml plasma/mg lacosamide administered per dose in patients with an average distribution volume of 50 L, and
      (b) a time point $T_{max}$, ss for reaching the maximum plasma concentration of lacosamide after drug administration in steady state of between 4 and 10 hours, and
      (c) a dose-normalized AUC in the steady state (AUC, ss, norm) of between about 0.34 to about 0.42 µg/ml/mg lacosamide per dose in patients with an average distribution volume of 50 L, and
      (d) a peak-trough fluctuation (PTF) which is below 55%, and
      (e) a dose normalized minimum steady state plasma levels $C_{min}$,ss,norm of between 0.0095 and 0.015 µg lacosamide/ml plasma/mg lacosamide per dosage unit in patients with an average distribution volume of 50 liters, and
      (f) a ka value of absorption of between 0.1/h to about 0.3/h.

7. The formulation according to claim 1, least one matrix retardation agent wherein the lacosamide release controlling comprises at least one matrix retardation agent.

8. The formulation according to claim 7, wherein the matrix comprises the matrix retardation agent in an amount of 15 to 40 wt % relative to the total weight of the formulation.

9. The formulation according to claim 7, wherein the at least one matrix retardation agent is selected from the group of poloxamers, hydroxyethylcellulose, hydroxypropylcellulose, methylcellulose, hydroxypropylmethylcellulose, polyvinyl pyrrolidone, polyvinyl alcohols, modified starch, pregelatinized starch, hydroxypropyl starch, sodium hyaluronate, alginic acid, alginate salts, carrageenan, chitosan, guar gum, pectin, and xanthan gum.

10. The formulation according to claim 9, wherein the matrix retardation agent is a hydrophilic polymer selected from the group consisting of
   a. hydroxyethyl cellulose, hydroxypropylcellulose (HPC), methylcellulose, and hydroxypropylmethylcellulose (HPMC), each having a viscosity of 2,000 mPas to 200,000 mPas in a 2 wt % aqueous solution at 20° C. when measured using Ubbelohde capillary viscosity, and
   b. polyethylene glycol having a viscosity given as a 1% solution in water at 25° C. of between about 1,000 and 50,000 mPas.

11. The formulation according to claim 9, wherein the matrix retardation agent is a HPMC having a viscosity of between about 500 and 5000 mPas in a 2 wt % aqueous solution at 20° C. in a 2 wt % aqueous solution at 20° C. when measured using Ubbelohde capillary viscosity.

12. The formulation according to claim 1, wherein the formulation comprises
   a. one or more excipients in a total amount of up to 75 %, and selected from the group of fillers, diluents, binders, lubricant, glidants, pharmaceutically acceptable processing aid agents, and/or flow modifiers, and
   b. a non-functional film coat in an amount of up to 30 wt %,
all amounts relative to the total weight of the formulation.

13. The formulation according to claim 1 comprising
   a. lacosamide in an amount of 30 to 60 wt %,
   b. the lacosamide release controlling agent in an amount of 10 to 30 wt %,
   c. a filler in an amount of 20 to 55 wt %,
   d. a binder in an amount of 10 to 50 wt %,
   e. a lubricant, glidant and/or flow modifier in an amount of 0 to 20 wt %,
   f. and a non-functional film coat in an amount of 0 to 5 wt %
all amounts relative to the total weight of the formulation.

14. The formulation according to claim 1, said formulation
(1) comprising
   (a) 100 mg, 200 mg, 300 mg or 400 mg lacosamide, and
   (b) at least one excipient being a lacosamide release controlling agent and being present in the matrix of said solid composition in an amount of about 10 to 30 wt % relative to the total weight of the formulation, and
   (c) one or more further therapeutically acceptable excipients, which may comprise one or more of the group comprising fillers/diluents, binders, and lubricants, glidants in a total amount of between about 25 and 70 wt %, relative to the total weight of the formulation, and
(2) said formulation
   (2.1) configured to deliver
      (2.1.1.)
         (a) an amount of about 8.5 wt % to about 41 wt % of lacosamide relative to the total lacosamide content of the formulation within 1 h,
         (b) an amount of about 17 wt % to about 64 wt % of lacosamide relative to the total lacosamide content of the formulation within 2 h, and
         (c) an amount of about 30 wt % to about 88 wt % of lacosamide relative to the total lacosamide content of the formulation within 4 h,
      when the in-vitro release of lacosamide is measured according to USP (edition 24) method <711>, dissolution apparatus 2, in 900 mL of 0.1N HCl at 50 rpm , and/or
      (2.1.2)
         (a) an amount of about 8.5 wt % to about 50 wt % of lacosamide relative to the total lacosamide content of the formulation within 1 h, (b) an amount of about 15 wt % to about 70 wt % of lacosamide relative to the total lacosamide content of the formulation within 2 h, and (c) an amount of about 28 wt % to about 90 wt % of lacosamide relative to the total lacosamide content of the formulation within 4 h, when the in-vitro release of lacosamide is measured according to USP (edition 24) method <711>, dissolution apparatus 2, in 900 mL of 0.1N HCl at 75 rpm, and said formulation (2.2) after once daily administration to animals comprises a pharmacokinetic profile comprising the following pharmacokinetic features:

(a) a time point $T_{max}$, ss for reaching the maximum plasma concentration of lacosamide after drug administration in steady state of between 4 and 10 hours, and (b) a time point $T_{max}$ for reaching the maximum plasma concentration of lacosamide after single dose administration of 7 hours or more, and (c) a peak-trough fluctuation (PTF) is below 50%, and (d) a ka value of absorption of between about 0.1/h to about 0.3/h.

15. The formulation according to claim 9, wherein the matrix retardation agent is a hydroxypropylmethylcellulose in a total amount of 10 to 30 wt % relative to the total weight of the formulation.

16. The formulation according to claim 7, wherein the at least one matrix retardation agent is (a) hydrophobic, and is selected from the group of fats, lipids, waxes, fatty alcohols, fatty acids, fatty alcohol ethers, and fatty acid esters, or (b) an inert polymer selected from the group consisting of acrylic resins, cellulose derivatives, vinyl acetate derivatives, and non-water soluble polyesters.

17. The formulation according to claim 1, wherein the formulation further comprises at least one release controlling layer surrounding said lacosamide-containing matrix, the at least one release controlling layer comprising the lacosamide release controlling agent, wherein the lacosamide-containing matrix (i) is an immediate release matrix, or (ii) a modified release matrix comprising at least one lacosamide release controlling agent.

18. The formulation according to claim 1, wherein said formulation is in the form of a single unit dosage.

19. The formulation according to claim 1, wherein the in vitro-release of lacosamide is pH independent.

20. A method for the treatment of epilepsy comprising administering the formulation of claim 1 to a subject in need thereof.

21. The method of claim 20 for the treatment of partial onset seizures.

22. The method of claim 20, wherein incidence of side effects is reduced compared to an immediate release formulation comprising the same amount of lacosamide and releasing more than 80% of lacosamide within 30 minutes when measured according to USP (edition 24), method <711>, dissolution apparatus 2, in 900 mL of 0.1N HCl at 75 rpm.

23. The formulation according to claim 1, comprising (a) lacosamide in an amount of 20 to 60 wt %, (b) the lacosamide release controlling agent in an amount of 10 wt % to 50 wt %, wherein the lacosamide release controlling agent is hydroxypropylmethylcellulose (HPMC) having a viscosity of 5,000 mPas to 50,000 mPas in a 2 wt-% aqueous solution at 20° C. when measured using Ubbelohde capillary viscosity, and (c) at least one excipient selected from (c1) fillers, and/or diluents in an amount of about 10 to about 40 wt %, (c2) binders, in an amount of about 10 to about 40 wt %, (c3) lubricants, glidants, or flow modifiers, in an amount of 0.5 to 5 wt %, and (c4) a non-functional film coat, in an amount of 0 to 5 wt %.

24. The formulation according to claim 23 in form of a tablet having a size of at least about 8 mm.

25. The formulation according to claim 17, wherein the lacosamide release controlling agent is selected from the group consisting of polyvinyl pyrrolidone, polyvinyl acetate, ethylcellulose, hydroxypropylmethylcellulose, acetate phthalate, hydroxypropyl cellulose, hydroxypropylmethylcellulose, acetate succinate, shellac, methacrylic acid copolymer type A, methacrylic, acid copolymer type B, methacrylic acid copolymer type C, ammonio methacrylate copolymer type A, ammonio methacrylate copolymer type B, and basic butylated methacrylate copolymer.

26. The method of claim 20, wherein the incidence of dizziness is reduced compared to an immediate release formulation comprising the same amount of lacosamide and releasing more than 80% of lacosamide within 30 minutes when measured according to USP (edition 24), method <711>, dissolution apparatus 2, in 900 mL of 0.1N HCl at 75 rpm.

27. A solid controlled release formulation for oral administration of lacosamide, the formulation comprising lacosamide and a lacosamide release controlling agent, wherein the solid controlled release formulation is configured such that a. no more than about 41 wt % of lacosamide relative to the total lacosamide content of the formulation is released within 1 h, b. no more than about 64 wt % of lacosamide relative to the total lacosamide content of the formulation is released within 2 h, and c. no more than about 88 wt % of lacosamide relative to the total lacosamide content of the formulation is released within 4 h, when the in-vitro release of lacosamide is measured according to USP (edition 24) method <711>, dissolution apparatus 2, in 900 mL of 0.1N HCl at 75 rpm, wherein lacosamide is present in an amount of 20-95% relative to total weight of the formulation and the lacosamide release controlling agent is present in a lacosamide-containing matrix in an amount from 10 wt % to 50 wt %.

28. The formulation according to claim 1, wherein the lacosamide release controlling agent is present in the lacosamide-containing matrix in an amount from 10 wt % to 30 wt %.

* * * * *

UNITED STATES PATENT AND TRADEMARK OFFICE
CERTIFICATE OF CORRECTION

PATENT NO. : 10,149,818 B2
APPLICATION NO. : 13/990861
DATED : December 11, 2018
INVENTOR(S) : Cawello et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 170 days.

Signed and Sealed this
Tenth Day of December, 2019

Andrei Iancu
*Director of the United States Patent and Trademark Office*